(12) United States Patent
Kaufmann et al.

(10) Patent No.: US 8,232,256 B2
(45) Date of Patent: Jul. 31, 2012

(54) MEANS FOR INHIBITING THE EXPRESSION OF PROTEIN KINASE 3

(75) Inventors: Jorg Kaufmann, Berlin (DE); Oliver Keil, Glienicke (DE); Ansgar Santel, Berlin (DE)

(73) Assignee: Silence Therapeutics AG, Berlin (DE)

( * ) Notice: Subject to any disclaimer, the term of this patent is extended or adjusted under 35 U.S.C. 154(b) by 229 days.

(21) Appl. No.: 12/307,052

(22) PCT Filed: Jul. 20, 2007

(86) PCT No.: PCT/EP2007/006492
§ 371 (c)(1),
(2), (4) Date: Apr. 15, 2009

(87) PCT Pub. No.: WO2008/009477
PCT Pub. Date: Jan. 24, 2008

(65) Prior Publication Data
US 2009/0304678 A1  Dec. 10, 2009

(30) Foreign Application Priority Data
Jul. 21, 2006  (EP) .................................. 06015262

(51) Int. Cl.
C12N 15/11 (2006.01)
C12N 5/00 (2006.01)
C07H 21/02 (2006.01)
C07H 21/04 (2006.01)
C12Q 1/68 (2006.01)
C12P 19/34 (2006.01)

(52) U.S. Cl. ................ 514/44 A; 536/24.1; 536/24.5; 435/6.1; 435/91.1; 435/325; 435/375

(58) Field of Classification Search ................ 536/23.1, 536/24.3, 24.33, 24.5
See application file for complete search history.

(56) References Cited

U.S. PATENT DOCUMENTS

| | | | |
|---|---|---|---|
| 5,504,103 A | 4/1996 | Bonjouklian et al. |
| 5,777,153 A | 7/1998 | Lin et al. |
| 5,820,873 A | 10/1998 | Choi et al. |
| 6,133,032 A | 10/2000 | Monia et al. |

(Continued)

FOREIGN PATENT DOCUMENTS

AU  778474  12/2004

(Continued)

OTHER PUBLICATIONS

Leenders, F. et al. "PKN3 is required for malignant prostate cell growth downstream of activated PI 3-kinase" *The EMBO Journal*, 2004, pp. 3303-3313, vol. 23, No. 16, XP-002459350.

(Continued)

*Primary Examiner* — Terra Cotta Gibbs
(74) *Attorney, Agent, or Firm* — Saliwanchik, Lloyd & Eisenschenk

(57) ABSTRACT

The present invention is related to a nucleic acid molecule and uses thereof. The nucleic acid molecule comprises a double-stranded structure, whereby the double-stranded structure comprises a first strand and a second strand, whereby the first strand comprises a first stretch of contiguous nucleotides and said first stretch is at least partially complementary to a target nucleic acid, and whereby the second strand comprises a second stretch of contiguous nucleotides and said second stretch is at least partially complementary to the first stretch, whereby the first stretch comprises a nucleic acid sequence which is at least partially complementary to a nucleotide core sequence of the nucleic acid sequence according to SEQ ID NO:1 (NM_013355).

53 Claims, 16 Drawing Sheets

U.S. PATENT DOCUMENTS

| | | | |
|---|---|---|---|
| 6,150,345 A | 11/2000 | Chun et al. | |
| 6,358,523 B1 | 3/2002 | Safinya et al. | |
| 6,395,713 B1 | 5/2002 | Beigelman et al. | |
| 6,518,458 B1 | 2/2003 | Moinet et al. | |
| 6,586,410 B1 | 7/2003 | Wheeler et al. | |
| 6,605,713 B1 | 8/2003 | Furste et al. | |
| 7,015,040 B2 | 3/2006 | Wolff et al. | |
| 7,056,704 B2 | 6/2006 | Tuschl et al. | |
| 7,196,145 B2 | 3/2007 | Ignatious | |
| 7,635,770 B2 * | 12/2009 | Khvorova et al. | 536/24.5 |
| 7,713,943 B2 | 5/2010 | Klippel-Giese et al. | |
| 2003/0073640 A1 | 4/2003 | Beigelman et al. | |
| 2003/0135033 A1 | 7/2003 | Klippel-Giese et al. | |
| 2004/0106569 A1 | 6/2004 | Klippel-Giese et al. | |
| 2008/0274116 A1 | 11/2008 | Keil et al. | |
| 2008/0319180 A1 | 12/2008 | Khvorova et al. | |
| 2009/0304678 A1 | 12/2009 | Kaurmann et al. | |
| 2010/0062967 A1 | 3/2010 | Keil et al. | |
| 2011/0008320 A1 | 1/2011 | Klippel-Giese et al. | |

FOREIGN PATENT DOCUMENTS

| | | |
|---|---|---|
| EP | 0 846 680 | 6/1998 |
| EP | 1 064 944 | 1/2001 |
| EP | 1 393 742 | 3/2004 |
| WO | WO 91/19813 | 12/1991 |
| WO | WO 96/10392 | 4/1996 |
| WO | WO 97/03939 | 2/1997 |
| WO | WO 98/08856 | 3/1998 |
| WO | WO 98/44909 | 10/1998 |
| WO | WO 98/51285 | 11/1998 |
| WO | WO 99/04819 | 2/1999 |
| WO | WO 99/05094 | 2/1999 |
| WO | WO 00/44895 | 8/2000 |
| WO | WO 00/73469 | 12/2000 |
| WO | WO 01/05374 | 1/2001 |
| WO | WO 01/75164 | 10/2001 |
| WO | WO 01/80900 | 11/2001 |
| WO | WO 02/34236 | 5/2002 |
| WO | WO 2004/012680 | 2/2004 |
| WO | WO 2004/019973 | 3/2004 |
| WO | WO 2005/105152 | 11/2005 |
| WO | WO 2006/053646 | 5/2006 |
| WO | WO 2006/074546 | 7/2006 |
| WO | WO 2008/009477 | 1/2008 |

OTHER PUBLICATIONS

Leenders, F. et al. "PKN3 is required for malignant prostate cell growth downstream of activated phosphatidylinositol 3-kinase" *EMBO Journal, Supplementary Information Section*, 2004, pp. 1-23, XP-002459351.

Deaton, R. A. et al. "Transforming Growth Factor-β1-induced Expression of Smooth Muscle Marker Genes Involves Activation of PKN and p38 MAPK" *The Journal of Biological Chemistry*, Sep. 2, 2005, pp. 31172-31181, vol. 280, No. 35, XP-002459353.

Santel, A. et al. "RNA interference in the mouse vascular endothelium by systemic administration of siRNA-lipoplexes for cancer therapy" *Gene Therapy*, 2006, pp. 1360-1370, vol. 13, XP-002443322.

Santel, A. et al. "A novel siRNA-lipoplex technology for RNA interference in the mouse vascular endothelium" *Gene Therapy*, 2006, pp. 1222-1234, vol. 13, XP-002459352.

Lu, Y. et al. "The *Drosophila* Pkn protein kinase is a Rho/Rac effector target required for dorsal closure during embryogenesis" *Genes Dev.*, 1999, pp. 1168-1180, vol. 13.

Mukai, H. "The Structure and Function of PKN, a Protein Kinase Having a Catalytic Domain Homologous to That of PKC" *J. Biochem.*, 2003, pp. 17-27, vol. 133.

Su, C. et al. "PKN Activation via Transforming Growth Factor-β1 (TGF-β1) Receptor Signaling Delays $G_2$/M Phase Transition in Vascular Smooth Muscle Cells" *Cell Cycle*, Mar. 15, 2007, pp. 739-749, vol. 6, No. 6.

Metzger, E. et al. "A novel inducible transactivation domain in the androgen receptor: implications for PRK in prostate cancer" *The EMBO Journal*, 2003, pp. 270-280, vol. 22, No. 2.

Dong, L. Q. et al. "Phosphorylation of protein kinase N By phosphoinositide-dependent protein kinase-1 mediates insulin signals to the actin cytoskeleton" *PNAS*, May 9, 2000, pp. 5089-5094, vol. 97, No. 10.

Fischer, A. et al. "Impaired tight junction sealing and precocious involution in mammary glands of PKN1 transgenic mice" *Journal of Cell Science*, 2007, pp. 2272-2283, vol. 120.

Flynn, P. et al. "Rho GTPase Control of Protein Kinase C-related Protein Kinase Activation by 3-Phosphoinositide-dependent Protein Kinase" *The Journal of Biological Chemistry*, Apr. 14, 2000, pp. 11064-11070, vol. 275, No. 15.

Manning, G. et al. "The Protein Kinase Complement of the Human Genome" *Science*, 2002, pp. 1912-1934, vol. 298.

Aleku, M. et al. "Atu027, a Liposomal Small Interfering RNA Formulation Targeting Protein Kinase N3, Inhibits Cancer Progression" *Cancer Res.*, Dec. 1, 2008, pp. 9788-9798, vol. 68, No. 23.

Kaufmann, J. et al. "Identification of novel effectors of invasive cell growth downstream of phosphoinositide 3-kinase" *Biochemical Society Transactions*, 2004, pp. 355-359, vol. 32, Part 2.

Mukai, H. et al. "Purification and Kinase Assay of PKN" *Methods in Enzymology*, 2006, pp. 234-250, vol. 406.

Oishi, K. et al. "Identification and Characterization of PKNβ, a Novel Isoform of Protein Kinase PKN: Expression and Arachidonic Acid Dependency Are Different from Those of PKNα" *Biochemical and Biophysical Research Communications*, 1999, pp. 808-814, vol. 261.

Section "Kolorektale Adenome, Adenomkrankhelt, Polypen" *Thiemes Innere Medizin*, 1999, pp. 1-6.

Office Action dated Jan. 3, 2011 in U.S. Appl. No. 11/722,948, filed Jan. 11, 2008.

Byk, G. et al. "Genetic Chemistry: Tools for Gene Therapy Coming from Unexpected Directions" *Drug Development Research*, 2000, pp. 566-572, vol. 50, XP-009046314.

Roe, E. T. et al. "Fatty Acid Amides . . . 9,10-Oihydroxystearic Acids", *Journal of the American Cancer Society*, 1949, pp. 2215-2218, vol. 71, XP-002385161.

Bedenbaugh, A. O. et al. "Synthesis of aldehydes and . . . carboxylic acids via imines", *Journal of the American Cancer Society*, 1970, pp. 5774-5775, vol. 92, XP-002385162.

Zhang, J. et al. "Targeted Gene Silencing by Small Interfering RNA-Based Knock-Down Technology" *Current Pharmaceutical Biotechnology*, 2004, pp. 1-7, vol. 5.

Lewis, D. L. et al. "Efficient delivery of siRNA for inhibition of gene expression in postnatal mice" *Nature Genetics*, Sep. 2002, pp. 107-108; Web Note A (2 pages) and Web Note B (1 page).

Waters, J. S. et al. "Phase I Clinical and Pharmacokinetic Study of Bcl-2 Antisense Oligonucleotide Therapy in Patients with Non-Hodgkin's Lymphoma" *J. Clin. Oncol.*, May 2000, pp. 1812-1823, vol. 18, No. 9.

Chi, K. N. et al. "A Phase I Dose-finding Study of Combined Treatment with an Antisense Bcl-2 Oligonucleotide (Genasense) and Mitoxantrone in Patients with Metastatic Hormone-refractory Prostate Cancer" *Clinical Cancer Research*, Dec. 2001, pp. 3920-3927, vol. 7.

Nemunaitis, J. et al. "Phase I Evaluation of ISIS 3521, an Antisense Oligodeoxynucleotide to Protein Kinase C-Alpha, in Patients with Advanced Cancer" *Journal of Clinical Oncology*, Nov. 1999, pp. 3586-3595, vol. 17, No. 11.

Cunningham, C. et al. "A Phase I Trial of H-*ras* Antisense Oligonucleotide ISIS 2503 Administered as a Continuous Intravenous Infusion in Patients with Advanced Carcinoma" *Cancer*, 2001, pp. 1265-1271, vol. 92.

Ogris, M. et al. "Targeting tumors with non-viral gene delivery systems" *Drug Discovery Today*, Apr. 2002, pp. 479-485, vol. 7, No. 8.

Cunningham, C. et al. " a Phase I Trial of c-*Raf* Kinase Antisense Oligonucleotide ISIS 5132 Administered as a Continuous Intravenous Infusion in Patients with Advanced Cancer" *Clinical Cancer Research*, May 2000, pp. 1626-1631, vol. 6.

Yuen, A. R. et al. "Phase I Study of an Antisense Oligonucleotide to Protein Kinase C-α (ISIS 3521/CGP 64128A) in Patients with Cancer" *Clinical Cancer Research*, Nov. 1999, pp. 3357-3363, vol. 5.

Devroe, E. et al. "Retrovirus-delivered siRNA" *BMC Biotechnology*, 2002, pp. 1-5, vol. 2.

Yacyshyn, B.R. et al. "A Placebo-Controlled Trial of ICAM-1 Antisense Oligonucleotide in the Treatment of Crohn's Disease" *Gastroenterology*, 1998, pp. 1133-1142, vol. 114.

Jansen, B. et al. "Chemosensitisation of malignant melanoma by BCL2 antisense therapy" *The Lancet*, Nov. 18, 2000, pp. 1728-1733, vol. 326.

Lewis, et al. "Delivery of siRNA and siRNA Expression Constructs to Adult Mammals by Hydrodynamic Intravascular Injection" *Methods of Enzymology*, 2005, pp. 336-350, vol. 392.

Section "Kolorektale Adenome, Adenomkrankhelt, Polypen" *Thiemes Innere Medizin*, 1999, pp. 1-6.

Entry "lipoma" from Stedman's Medical Dictionary, The Williams & Wilkins Company, Baltimore, 1996, pp. 1-4.

Entry "Trichilemmom" from Zetkin, M. and Schaldach, H., Worterbuch der Medizin, Ullstein Mosby, Berlin, 1992, pp. 1-3.

Akhtar, S. et al. "The delivery of antisense therapeutics" *Advanced Drug Delivery Reviews*, 2000, pp. 3-21, vol. 44.

Opalinska, J.B. et al. "Nucleic-Acid Therapeutics: Basic Principles and Recent Applications" *Nature Reviews*, 2000, pp. 503-514, vol. 1.

Hoffman, R.M. "Orthotopic metastatic mouse models for anticancer drug discovery and evaluation: a bridge to the clinic" *Investigational New Drugs*, 1999, pp. 343-359, vol. 17.

Oishi, K. et. al. "Identification and Characterization of PKNβ, a Novel Isoform of Protein Kinase PKN: Expression and Arachidonic Acid Dependency Are Different from those of PKNα" *Biochemical and Biophysical Research Communications*, Aug. 11, 1999, pp. 808-814, vol. 261, Issue 3.

Katso, R. et al. "Cellular Function of Phosphoinositide 3-Kinases: Implications for Development, Immunity, Homeostasis, and Cancer" *Annu. Rev. Cell Dev. Biol.*, 2001, pp. 615-675, vol. 17.

Knuefermann, C. et al. "HER2/PI-3K/Akt activation leads to a multidrug resistance in human breast adenocarcinoma cells" *Oncogene*, 2003, pp. 3205-3212, vol. 22.

Okudela, K. et al. "K-ras Gene Mutation Enhances Motility of Immortalized Airway Cells and Lung Adenocarcinoma Cells via Akt Activation" *American Journal of Pathology*, Jan. 2004, pp. 91-100, vol. 164, No. 1.

Caplen, N. "RNAi as a gene therapy approach" *Expert Opin. Biol. Ther.*, 2003, pp. 575-586, vol. 3, No. 4.

Coburn, G. A. et al. "siRNAs: a new wave of RNA-based therapeutics" *Journal of Antimicrobial Chemotherapy*, Apr. 2003, pp. 753-756, vol. 51, No. 4.

Agami, R. "RNAi and related mechanisms and their potential use for therapy" *Current Opinion in Chemical Biology*, 2002, pp. 829-834, vol. 6.

Check, E. "RNA to the rescue?" *Nature*, Sep. 4, 2003, pp. 10-12, vol. 425.

Agrawal, S. et al. "Antisense therapeutics: is it as simple as complementary base recognition" *Molecular Medicine Today*, Feb. 2000, pp. 72-81, vol. 6.

Dykxhoorn, D. M. et al. "Running Interference: Prospects and Obstacles to Using Small Interfering RNAs as Small Molecule Drugs" *Annu. Rev. Biomed. Eng.*, 2006, pp. 377-402, vol. 8.

Jain, R. K. "Barriers to Drug Delivery in Solid Tumors" *Scientific American*, Jul. 1994, pp. 58-65, vol. 171, No. 1.

Gura, T. "Systems for Identifying New Drugs are Often Faulty" *Science*, Nov. 7, 1997, vol. 278, pp. 1041-1042.

MSNBC News Services, "Mixed results on new cancer drug" Nov. 9, 2000, pp. 1-4.

Crystal, R. G. "Transfer of Genes to Humans: Early Lessons and Obstacles to Success" *Science*, Oct. 20, 1995, pp. 404-409, vol. 270.

Izquierdo, M. "Short interfering RNAs as a tool for cancer gene therapy" *Cancer Gene Therapy*, 2005, pp. 217-227, vol. 12.

Shankar, P. et al. "The Prospect of Silencing Disease Using RNA Interfernece" *JAMA*, Mar. 16, 2005, pp. 1367-1373, vol. 293, No. 11.

Heidenreich, O. "Oncogene Suppression by Small Interfering RNAs" *Current Pharmaceutical Biotechnology*, 2004, pp. 349-354, vol. 5.

Caplen, N. J. et al. "Specific inhibition of gene expression by small double-stranded RNAs in invertebrate and vertebrate systems" *PNAS*, Aug. 14, 2001, pp. 9742-9747, vol. 98, No. 17.

Vickers, T. A. et al. "Efficient Reduction of Target RNAs by Small Interfering RNA and RNase H-dependent Antisense Agents" *Journal of Biological Chemistry*, Feb. 28, 2003, pp. 7108-7118, vol. 278, No. 9.

Di Cristofano, A. et al. "Pten is essential for embryonic development and tumour suppression" *Nature Genetics*, Aug. 19, 1998, pp. 348-355, vol. 19.

Klippel, A. et al. "Activation of Phosphatidylinositol 3-Kinase is Sufficient for Cell Cycle Entry and Promotes Cellular Changes Characteristic of Oncogenic Transformation" *Molecular and Cellular Biology*, Oct. 1998, pp. 5699-5711, vol. 18, No. 10.

Kobayashi, M. et al. "Dedifferentiation of adenocarcinomas by activation of phosphatidylinositol 3-kinase" *Proc. Natl. Acad. Sci. USA*, Apr. 1999, pp. 4874-4879, vol. 96.

Maruo, Y. et al. "ICAM-1 Expression and the Soluble ICAM-1 Level for Evaluating the Metastatic Potential of Gastric Cancer" *Int. J. Cancer*, 2002, pp. 486-490, vol. 100.

Petersen, O. W. et al. "Interaction with basement membrane serves to rapidly distinguish growth and differentiation pattern of normal and malignant human breast epithelial cells" *Proc. Natl. Acad. Sci. USA*, Oct. 1992, pp. 9064-9068, vol. 89, Cell Biology.

Roymans, D. et al. "Phosphatidylinositol 3-kinases in tumor progression" *Eur. J. Biochem.*, 2001, pp. 487-498, vol. 268.

Rudland, P. S. et al. "Prognostic Significance of the Metastasis-associated Protein Osteopontin in Human Breast Cancer" *Cancer Research*, Jun. 15, 2002, pp. 3417-3427, vol. 62.

Shibata, H. et al. "PKNβ interacts with the SH3 Domains of Graf and a Novel Graf Related Protein, Graf 2, Which are GTPase Activating Proteins for Rho Family" *J. Biochem.*, 2001, pp. 23-31, vol. 130.

Stein, R. C. et al. "PI3-kinase inhibition: a target for drug development?" *Molecular Medicine Today*, 2000, pp. 347-357, vol. 6.

Vlahost, C. J. et al. "A Specific Inhibitor of Phosphatidylinositol 3-Kinase, 2-(4-Morpholinyl)-8-phenyl-4H-1-benzopyran-4-one (LY294002)" *The Journal of Biological Chemistry*, Feb. 18, 1994, pp. 5241-5248, vol. 269, No. 7.

Yu, K et al. "mTOR, a novel target in breast cancer: the effect of CCI-779, an MTOR inhibitor, in preclinical models of breast cancer" *Endocrine-Related Cancer*, 2001, pp. 249-258, vol. 8.

Ali, I. U. "Gatekeeper for Endometrium: the PTEN Tumor Suppressor Gene" *Journal of the National Cancer Institute*, Jun. 7, 2000, pp. 861-863, vol. 92, No. 11.

Cantley, L. C. et al. "New insights into tumor suppression: PTEN suppresses tumor formation by restraining the phosphoinositide 3-kinase/AKT pathway", *Proc. Natl. Acad. Sci. USA*, Apr. 1999, pp. 4240-4245, vol. 96.

Sternberger, M. et al. "GeneBlocs Are Powerful Tools to Study and Delineate Signal Transduction Processes That Regulate Cell Growth and Transformation" *Antisense & Nucleic Acid Drug Development*, 2002, pp. 131-143, vol. 12.

Vazquez, F. et al. "The PTEN tumor suppressor protein: an antagonist of phosphoinositide 3-kinase signaling" *Biochimica et Biophysica Acta*, 2000, pp. M21-M35, vol. 1470.

Office Action dated Apr. 13, 2011 in U.S. Appl. No. 12/713,513, filed Feb. 26, 2010.

Petiot, A. et al. "Distinct Classes of Phosphatidylinositol 3'-Kinases are involved in Signaling Pathways that Control Macroautophagy in HT-29 Cells" *The Journal of Biological Chemistry*, Jan. 14, 2000, pp. 992-998, vol. 275, No. 2.

Office Action dated Nov. 6, 2006 in U.S. Appl. No. 10/640,274, filed Aug. 14, 2003.

Office Action dated Nov. 21, 2008 in U.S. Appl. No. 10/640,274, filed Aug. 14, 2003.

Office Action dated Jul. 21, 2009 in U.S. Appl. No. 10/640,274, filed Aug. 14, 2003.

Office Action dated Jul. 2, 2007 in U.S. Appl. No. 10/640,274, filed Aug. 14, 2003.

* cited by examiner

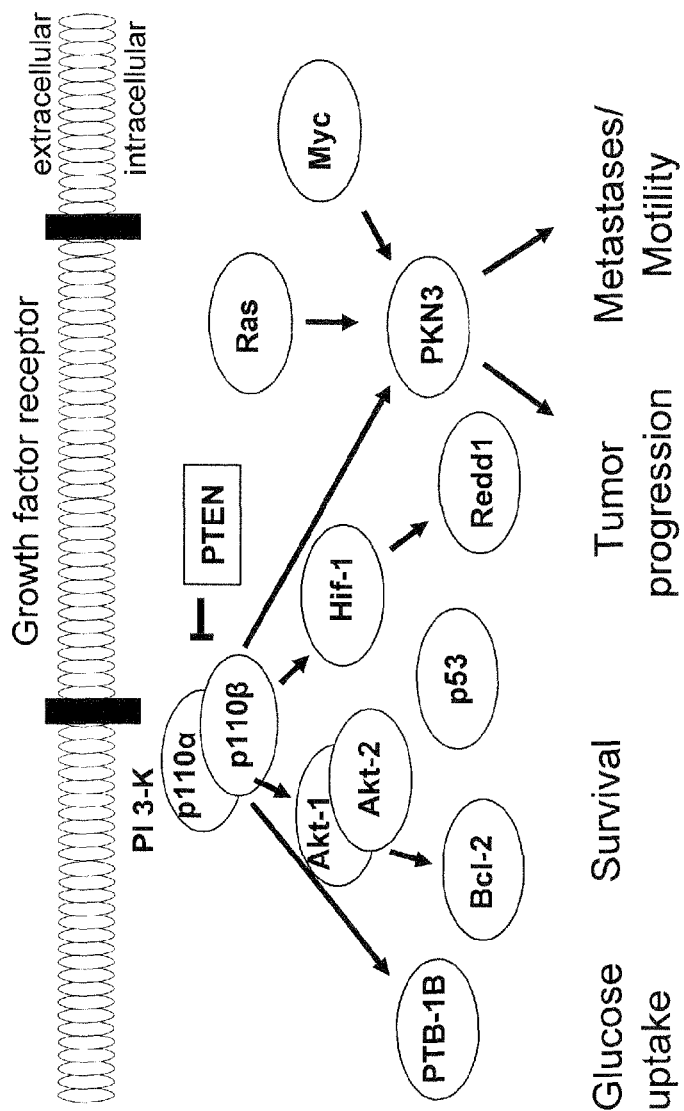

Fig 1. PKN3, novel S/T kinase belonging to the family of AGC-type kinases. PKN3 have been identified a novel effector mediating malignant growth downstream of activated PI3K. PKN3 is required for motility of cells and invasive prostate cell growth as assessed by 3-dimensional cell culture assays and in an orthotopic tumor model by inducible expression of short hairpin RNA molecules. PKN3 seems to be a gene target for inhibtion of motility of endothelial vells (tumor angiogenesis) and migration of tumor cells.

Leenders et al. 2004. PKN3 is required for malignant prostate cell growth downstream of activated PI 3-kinase. *EMBO J.* 23 (16): 3303-3313.

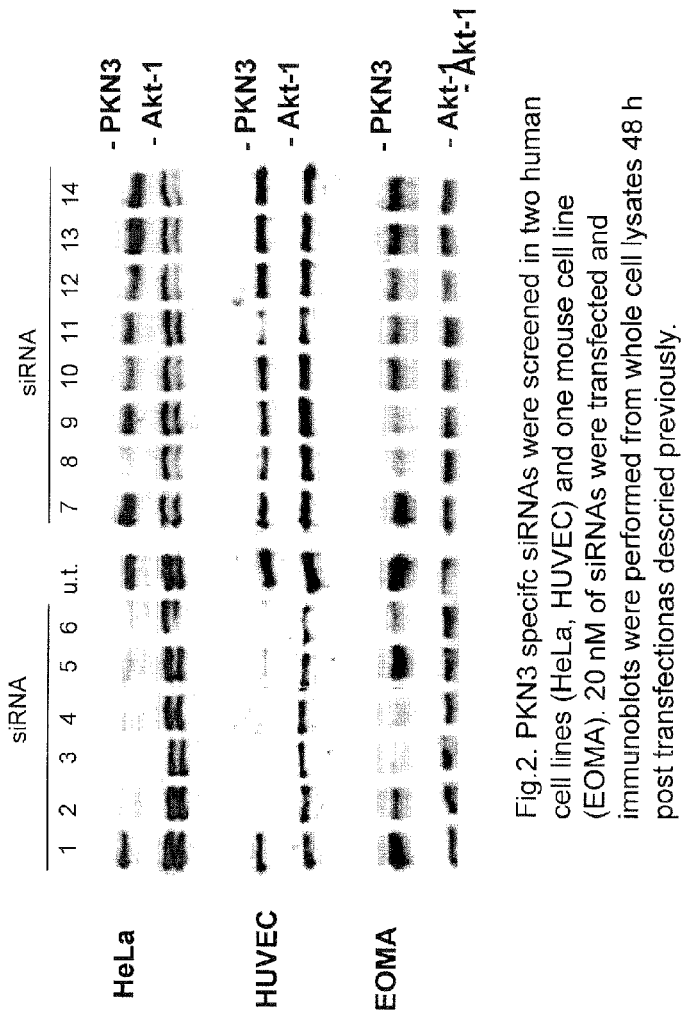

Fig.2. PKN3 specific siRNAs were screened in two human cell lines (HeLa, HUVEC) and one mouse cell line (EOMA). 20 nM of siRNAs were transfected and immunoblots were performed from whole cell lysates 48 h post transfection as descried previously.

| | |
|---|---|
| PKN3-hm-1s | agcugaagaucaaggaggg-P (SEQ ID NO:2) |
| PKN3-hm-1as | ccccuugaucuucagcu-P (SEQ ID NO:3) |
| PKN3-hm-2s | cuugaggacuuccuggaca-P (SEQ ID NO:4) |
| PKN3-hm-2as | uguccaggaaguccucaag-P (SEQ ID NO:5) |
| PKN3-hm-3s | uugaggacuuccuggacaa-P (SEQ ID NO:6) |
| PKN3-hm-3as | uuguccaggaaguccucaa-P (SEQ ID NO:7) |
| PKN3-hm-4s | aggacuuccuggacaaugc-P (SEQ ID NO:8) |
| PKN3-hm-4as | gcauugguccaggaaguccu-P (SEQ ID NO:9) |
| PKN3-hm-5s | ccuggacaaugccugucac-P (SEQ ID NO:10) |
| PKN3-hm-5as | gugacaggcauuguccagg-P (SEQ ID NO:11) |
| PKN3-hm-6s | gggacacuuugggaaguc-P (SEQ ID NO:12) |
| PKN3-hm-6as | gaccuucccaaaguguccc-P (SEQ ID NO:13) |
| PKN3-hm-7s | uuggaagguccucuggu-P (SEQ ID NO:14) |
| PKN3-hm-7as | accaggaggaccuucccaa-P (SEQ ID NO:15) |
| PKN3-hm-8s | cuccagccaugccugcuuu-P (SEQ ID NO:16) |
| PKN3-hm-8as | aaagcaggcauggcuggag-P (SEQ ID NO:17) |
| PKN3-hm-9s | auucagaagcuccuccaga-P (SEQ ID NO:18) |
| PKN3-hm-9as | ucuggaggagcuucugaau-P (SEQ ID NO:19) |
| PKN3-hm-10s | ucagaagcuccuccagaag-P (SEQ ID NO:20) |
| PKN3-hm-10as | cuucuggaggagcuucuga-P (SEQ ID NO:21) |
| PKN3-hm-11s | cagaagcuccuccagaagu-P (SEQ ID NO:22) |
| PKN3-hm-11as | acuucuggaggagcuucug-P (SEQ ID NO:23) |
| PKN3-hm-12s | ucuucaggaccaccaacug-P (SEQ ID NO:24) |
| PKN3-hm-12as | caguugguccugaaga-P (SEQ ID NO:25) |
| PKN3-hm-13s | cuucaggaccaccaaacugg-P (SEQ ID NO:26) |
| PKN3-hm-13as | ccaguugguccugaag-P (SEQ ID NO:27) |
| PKN3-hm-14s | ucaggaccaccaacugga-P (SEQ ID NO:28) |
| PKN3-hm-14as | ugccaguuggugguccuga-P (SEQ ID NO:29) |

Tab. 1: Sequence of PKN3 specific siRNAs used in the functional screen.

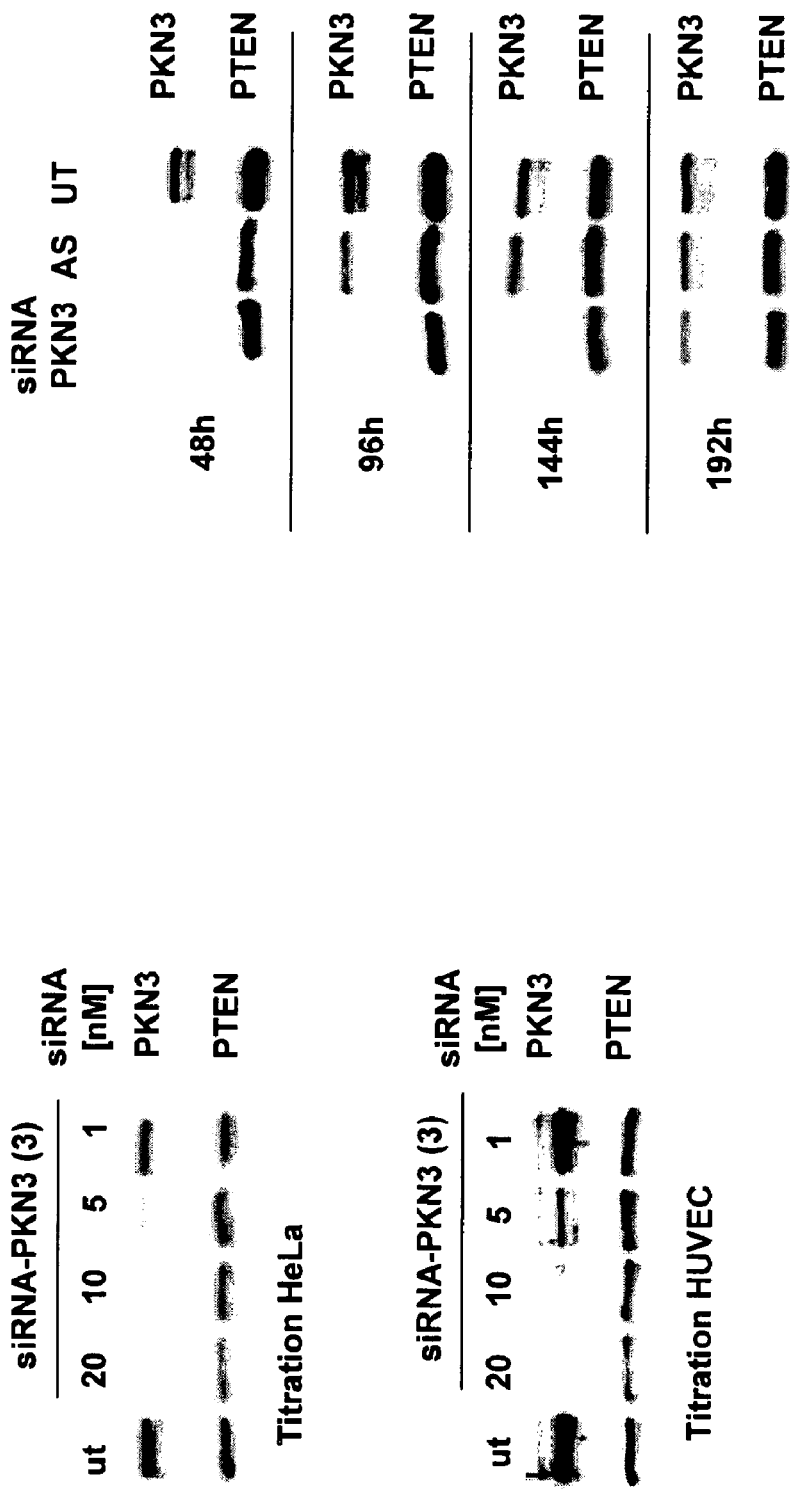

Fig.4. siRNA-PKN3 (3) and an PKN3 specific antisense molecule (GB control, PKN3 specific antisense molecule) was transfected into Hela cells and protein lysates were prepared at the indicated time points, siRNA-lipoplexe was removed after 24 h.

Fig.3. Determination of IC 50 of siRNA-PKN3 (3)-lipoplex after transfection in HeLa and HUVEC cells. Protein lysates were prepared 48h post transfection and immunoblots with PKN3 and PTEN specific antiblodies.

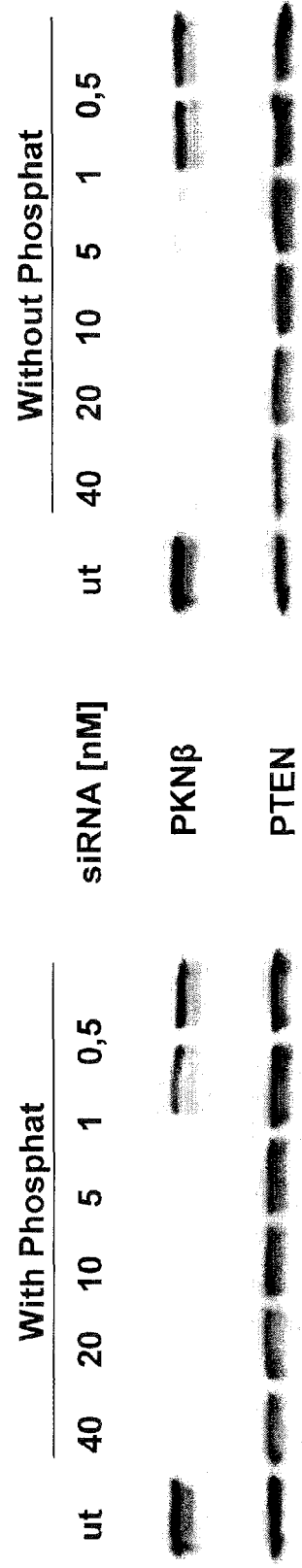
Fig.5. Comparison on efficacy of PKN3-siRNA-lipoplex with siRNA molecules with and without a 3'-P in HeLa cells. Different amounts of siRNA-PKN3 (3) was transfected as lipoplexes into HeLa cells and protein lysates were prepared 48 h post transfection. Immunoblot was analysed as described previously.

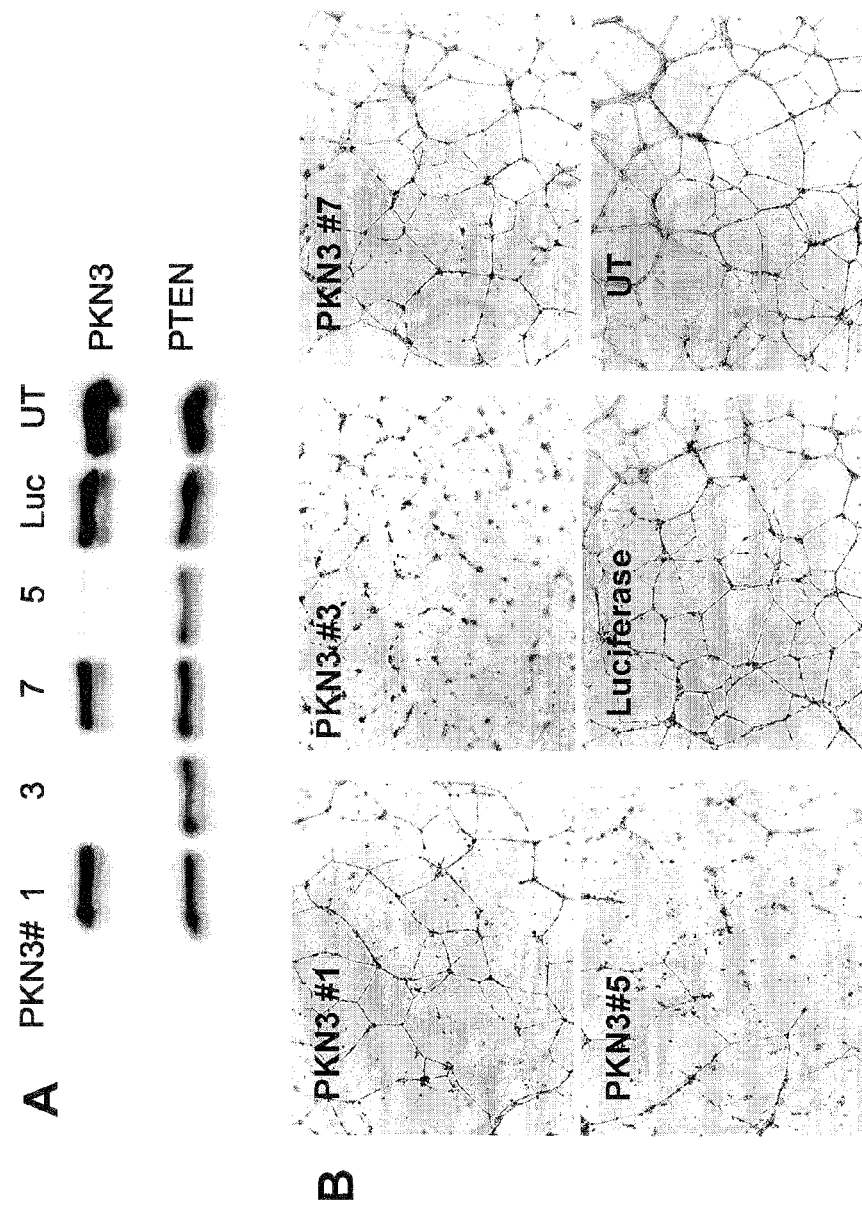

Fig. 6. Effect of loss-of-PKN3 function on HUVEC growth on extracellular matrix..HUVECs were transfected with four different siRNA-PKN3 lipoplexes (PKN3#1, PKN3#3, PKN3#7, PKN3#5 (see corresponding immunoblot in (a)) and with siRNALuc-lipoplex (20nM) and were kept growing to confluency within the first 48 hours of transfection. After 48 hours cells were trypsinized, replated with equal cell numbers (110.000 cellss) were plated on matigel containing 24 wells. Representative microscopic pictures were taken to monitor changes in HUVEC cell growth at 20 h post replating. In the case of the potent siRNA-PKN3-lipoplexes inhibition of growth was observed (lower panels).

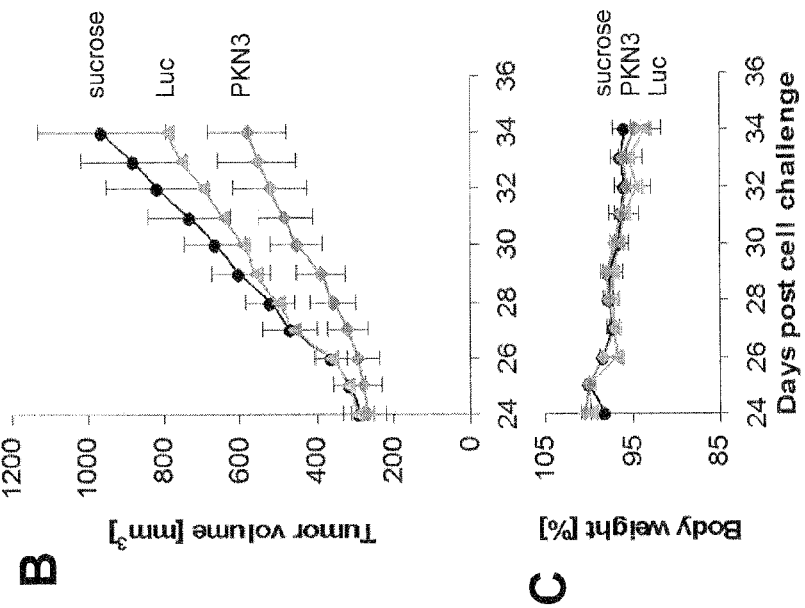

Fig. 7 Inhibition of subcutaneous s.c. PC-3 xenograft tumor growth by siRNA^PKN-3-lipoplex treatment. Growth of established PC-3 xenografts was significantly inhibited with siRNA^CD31-lipoplex (diamonds) in comparison to siRNA^Luc-lipoplex (triangles) treated as indicated (standard dose 1.88 mg/kg/day siRNA; 14.5 mg/kg/day lipid; arrow) or isotonic sucrose (solid spheres). Changes in body weights were monitored during the treatment as shown in the corresponding diagram below. Growth of established s.c. PC-3 tumors (seven mice per group) was significantly inhibited by siRNA^PKN3-lipoplex (diamonds) when compared to siRNALuc-lipoplexes (triangles) or isotonic sucrose (solid spheres). Data represent the means of daily tumor volume ± s.e.m.

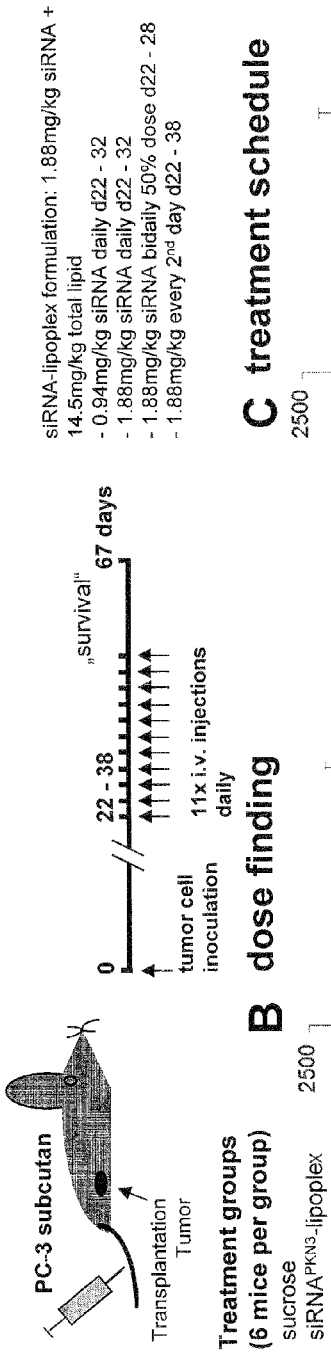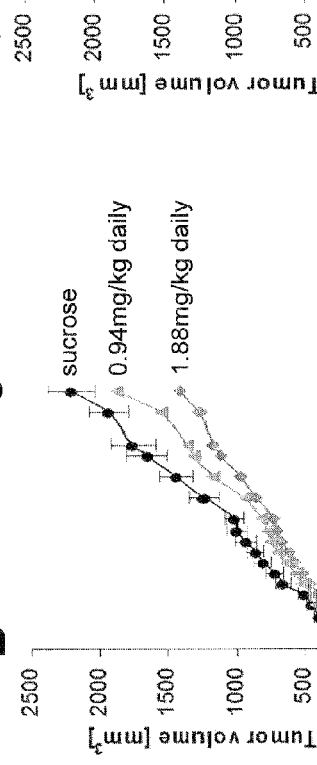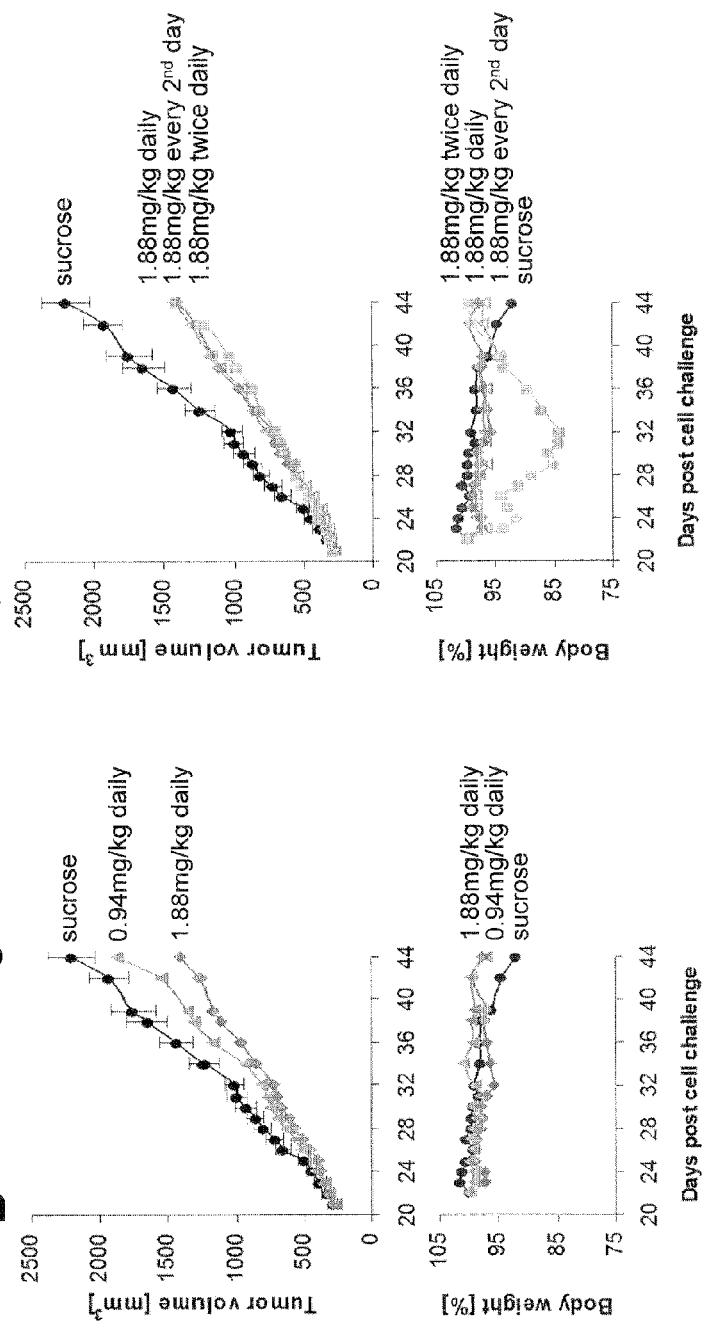
Fig. 8 Inhibition of subcutaneous PC-3 xenograft tumor growth by siRNAPKN3-3-lipoplex treatment. Different lipoplex doses (left panels) or different treatment schedules (right panel) were tested.

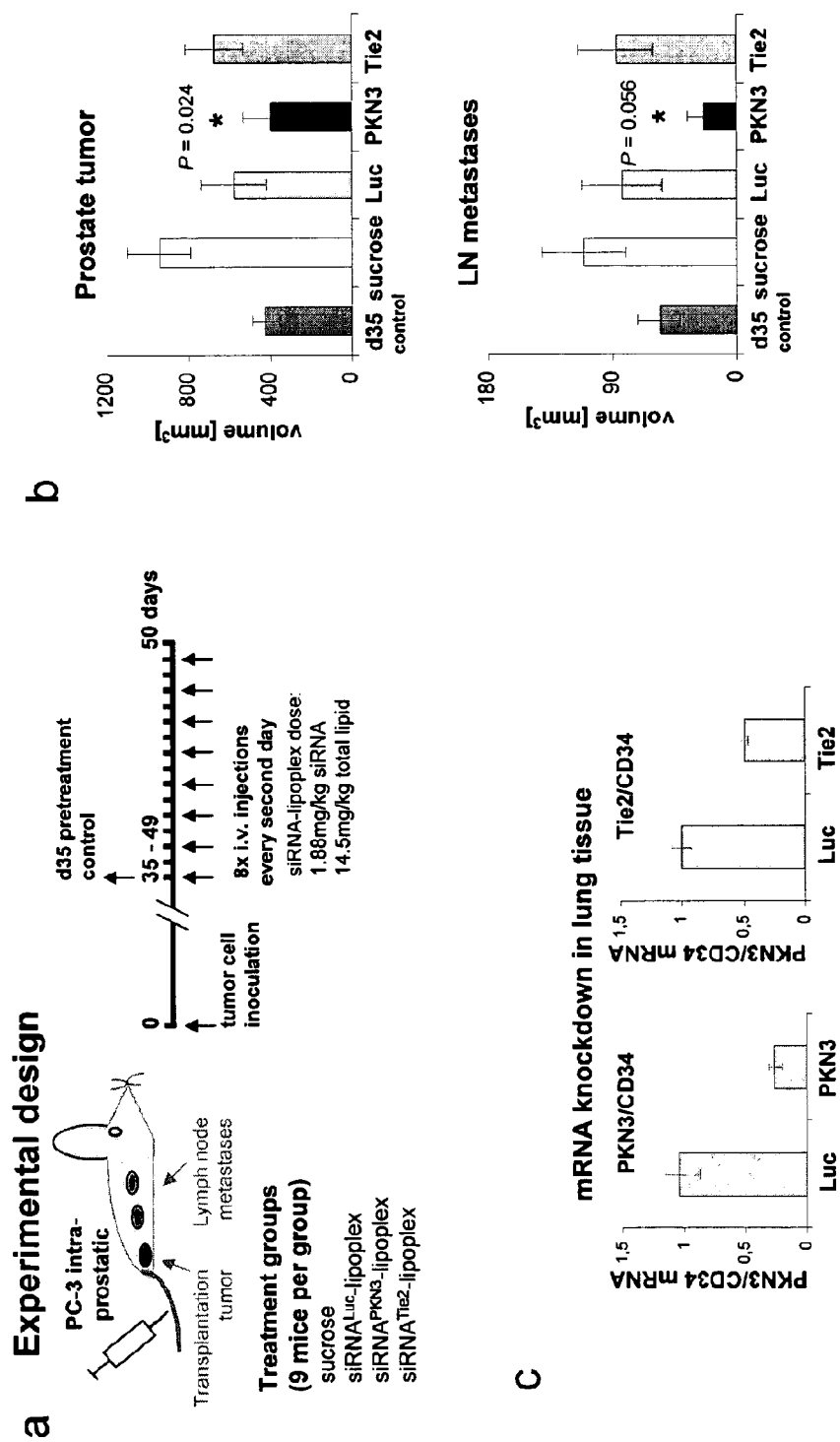

Fig. 9 Systemic treatment of mice with siRNA-PKN3-3-lipoplexes inhibits tumor growth in an orthotopic xenograft tumor model. (a) Experimental design to analyze the efficacy of siRNACD31-lipoplex treatment in an orthotopic PC-3 prostate tumor and lymph node metastasis model. (b) Inhibition of volume from prostate PC-3 tumor and lymph node metastases in mice after treatment with the indicated siRNA-lipoplexes or sucrose. The tumor and metastasis volumes before treatment start are indicated on the left (d35, control). Statistical significance is indicated by asterisk. (c) Reduction of PKN-3 and Tie2 mRNA levels in lung tissue from mice treated with corresponding siRNA-lipoplexes as revealed by quantitative TaqMan reverse transcription-polymerase chain reaction after. The relative averaged amount of Tie2 or PKN-3 mRNA levels in the lung normalized to CD34 mRNA is shown to demonstrate in vivo lipoplex mediated RNA interference in vivo..

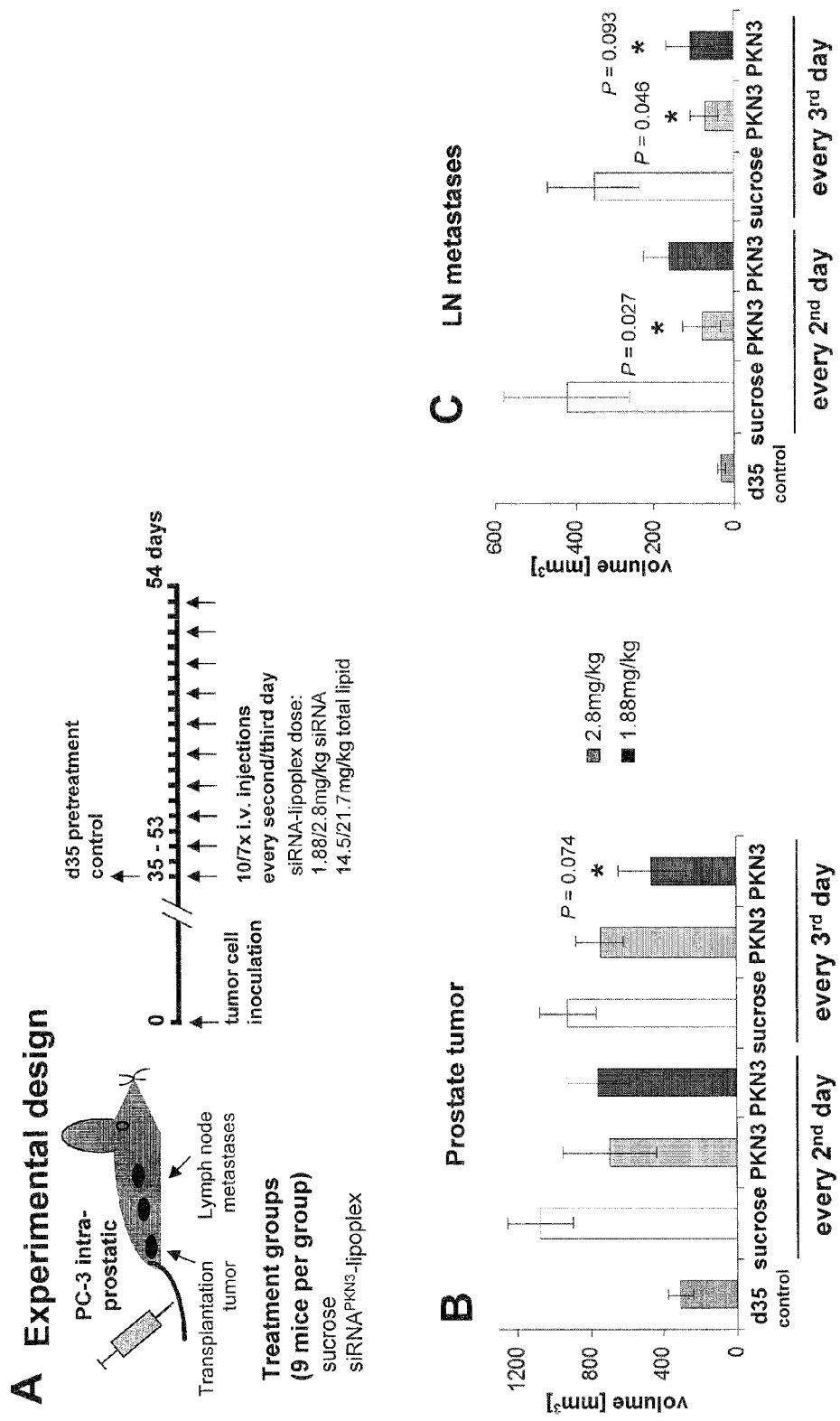
Fig. 10 Systemic treatment of mice with siRNA-PKN3-3-lipoplexes inhibits tumor growth in an orthotopic xenograft tumor model. Different treatment schedules are tested (every sevond versus every third day i.v. injection)

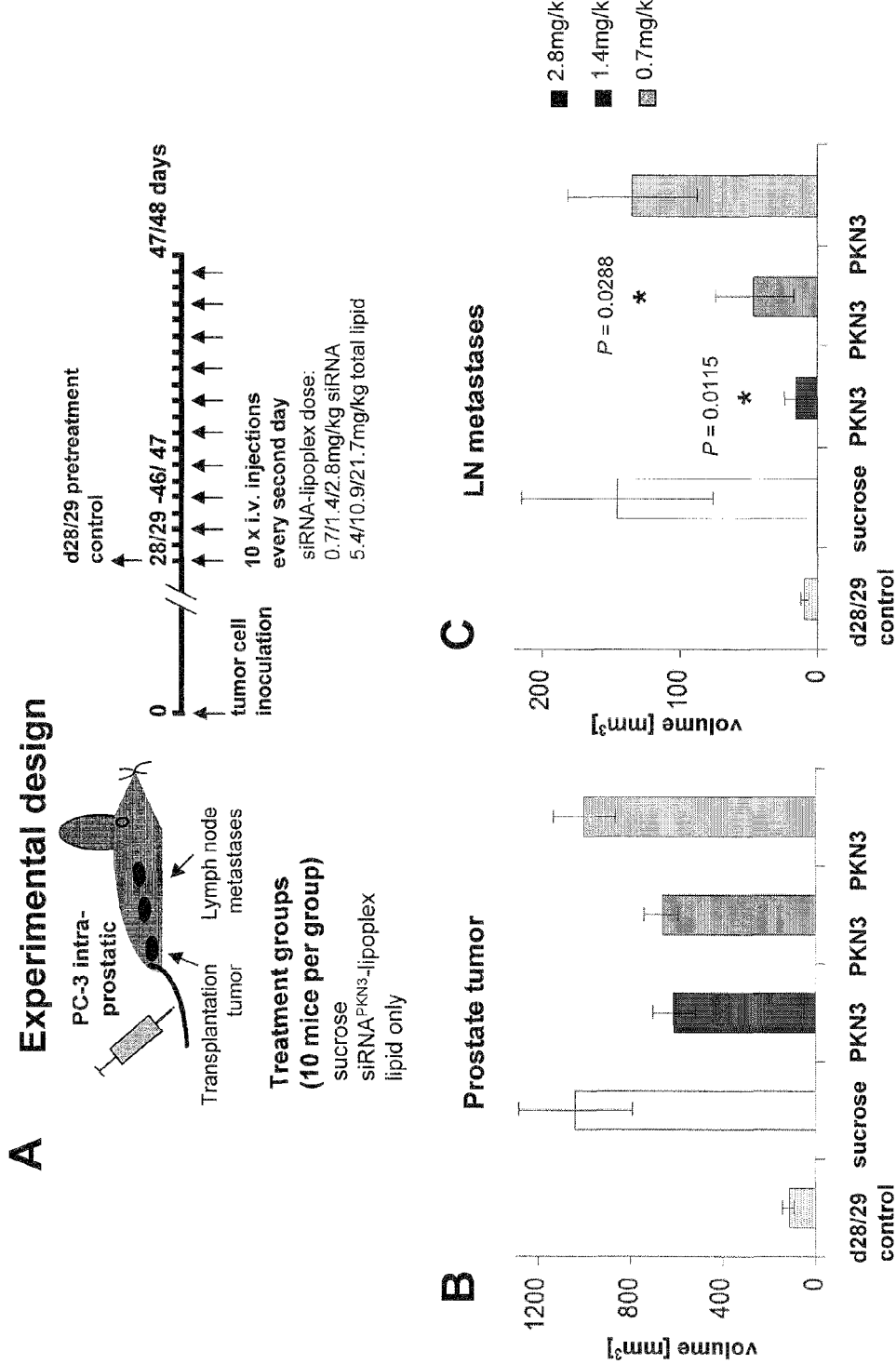
Fig. 11 Systemic treatment of mice with siRNA-PKN3-3lipoplexes inhibits tumor growth in an orthotopic xenograft tumor model. Different doses are tested (every sevond day i.v. injection).

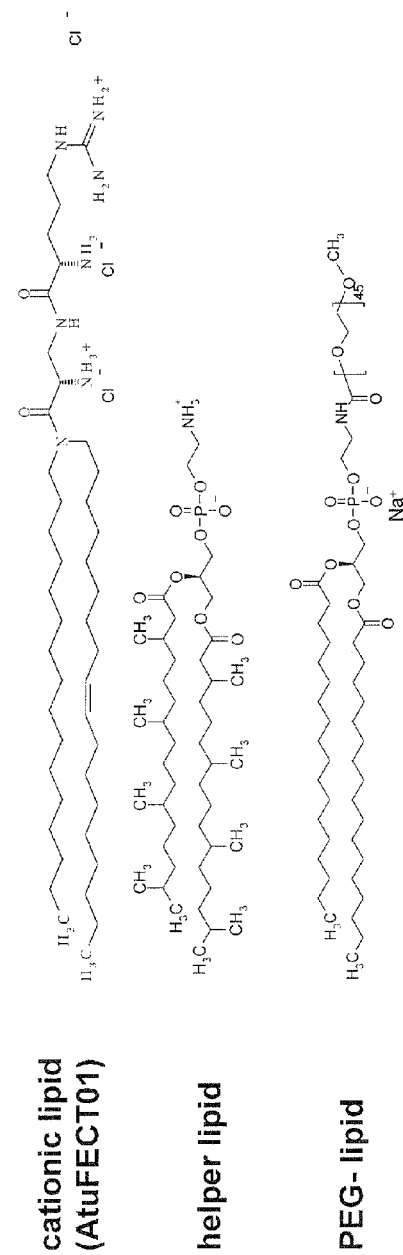
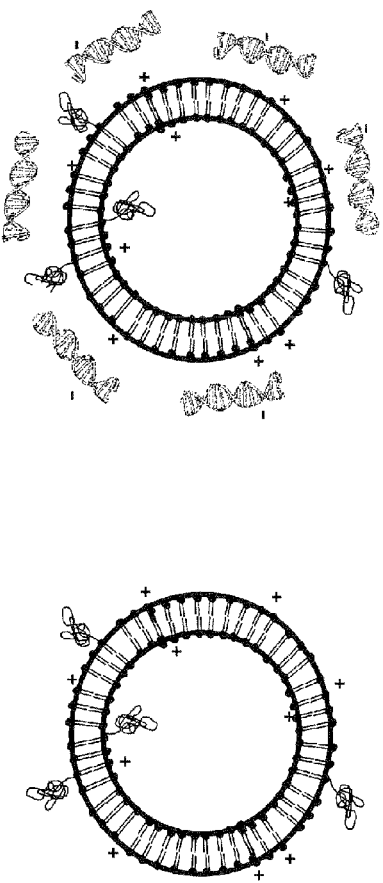
Fig. 12A
Fig. 12B PKN3 siRNA
PKN3-hm-3A 5'-uguccaggaaguccucaa-3' (SEQ ID NO:7)
PKN3-hm-3B 3'-aacagguccuucaggaguu-5' (SEQ ID NO:6)
bold=2'-O-methyl modification

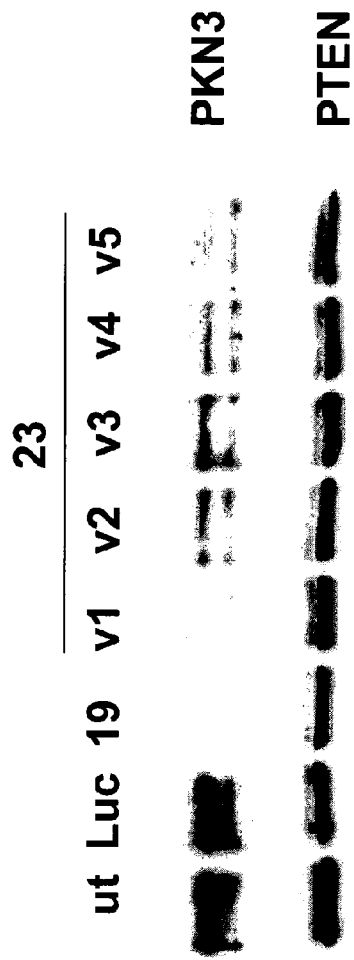
Fig. 13: Knock down efficacy of different siRNA$^{PKN3}$ molecule variations v1 to v5 of 23nt lenght in comparison to the 19mer. HeLaB cells were plated in 6 wells (40k), transfected 16h later with 20nM siRNA and lysed for protein extraction 48h after transfection. Western Blot of lysates probed with anti-PKN3 and anti-Pten (loading control).
ut = untreated, KO = control

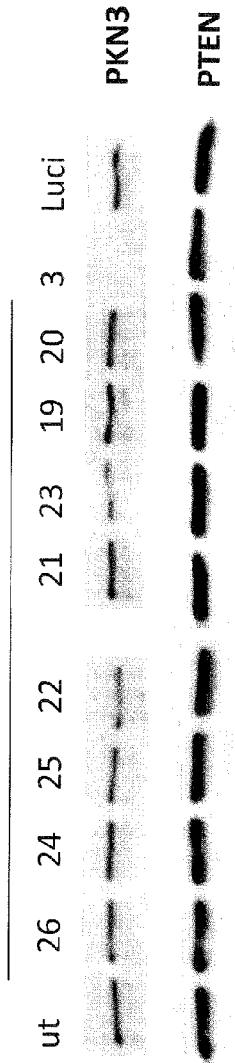
Fig. 14: Primary screen of PKN3-hmr-23-siRNA molecules in HUVEC cells. Cells were plated in 6 wells (40k), transfected 16h later with 20nM siRNA and 1μg/ml AtuFECT01 and lysed for protein extraction 72h after transfection. Western Blot of lysates probed with anti-PKN3 and anti-Pten (loading control).
ut = untreated; Luci = Luciferase siRNA; co 3 = PKN3-hm-3A/B23-v1

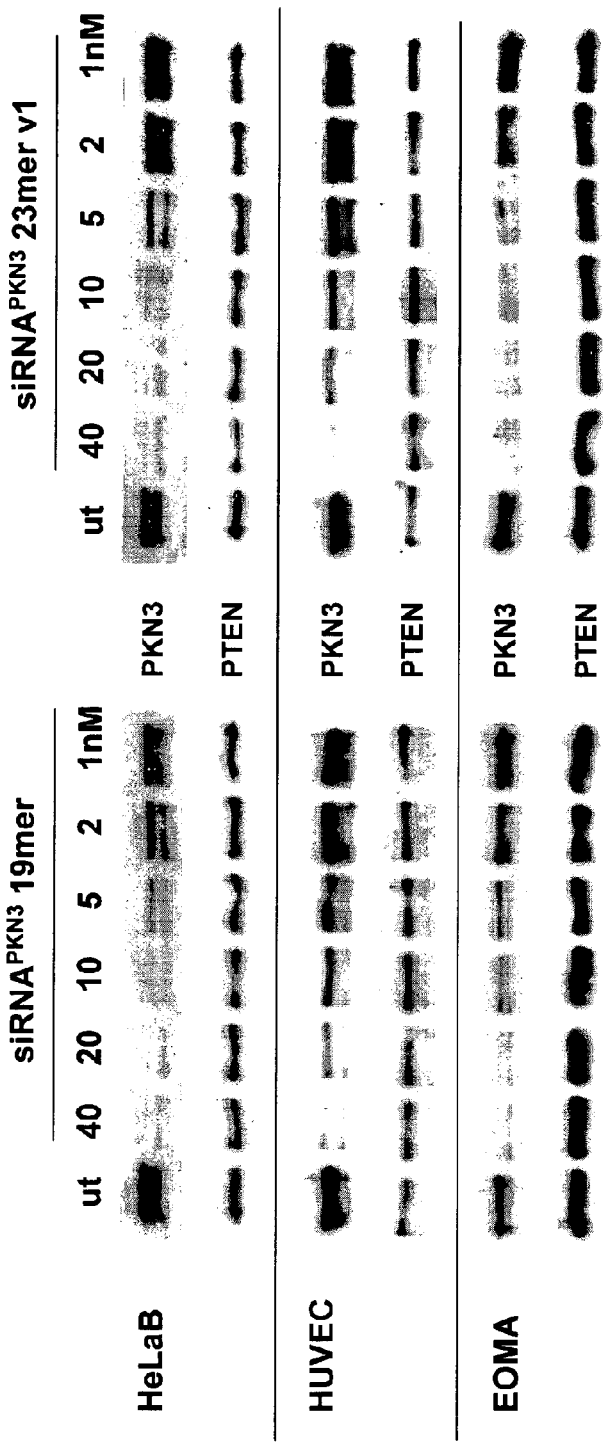
Fig. 15: Dose titration of siRNA$^{PKN3}$ 23mer variation v1 in comparison to the 19mer in different cell lines. Cells were plated in 6 wells (40k), transfected 16h later with indicated concentration of siRNA and lysed for protein extraction 48h after transfection. Western Blot of lysates probed with anti-PKN3 and anti-Pten (loading control).
ut = untreated

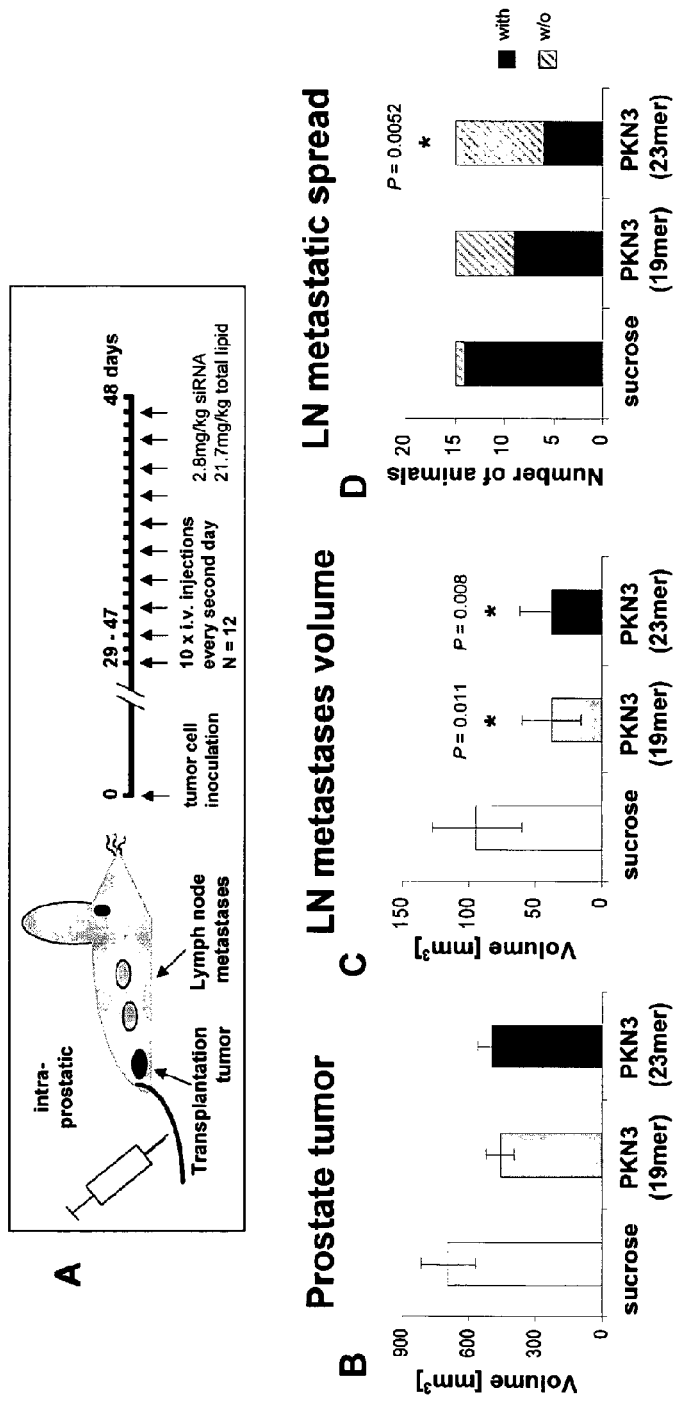
Fig. 16: Systemic treatment of mice with siRNA^PKN3-lipoplexes inhibits LN metastases growth in an orthotopic xenograft tumor model. 19mer and 23mer siRNA^PKN3 are tested and show the same efficacy in this prostate tumor model.

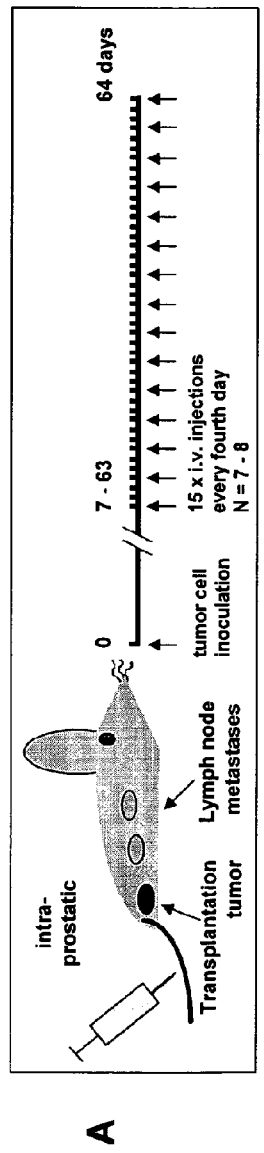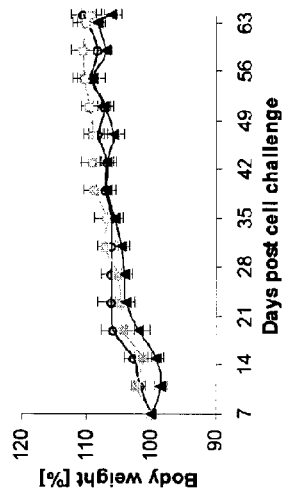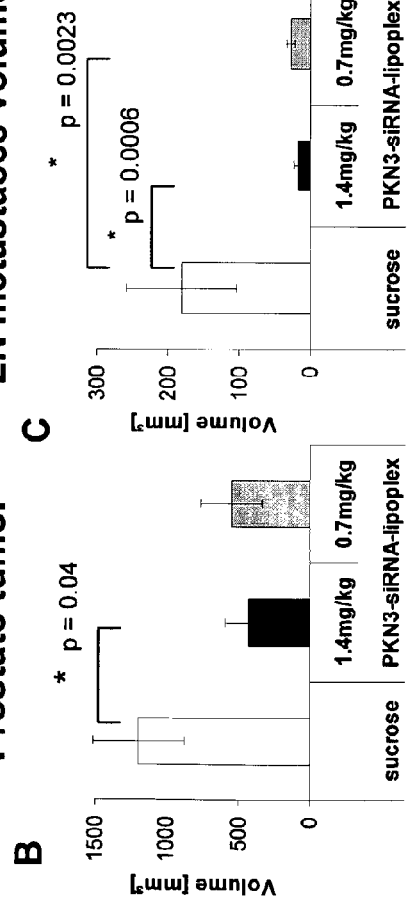
Fig. 17: Systemic treatment of mice with PKN3 AtuPLEX (Atu027) shows efficacy in an orthotopic xenograft tumor model. 23mer siRNA$^{PKN3}$-lipoplexes are tested in two different dosages (start at day 7, 15 bolus injections every fourth day)

```
                              SEQUENCE LISTING

<160> NUMBER OF SEQ ID NOS: 57

<210> SEQ ID NO 1
<211> LENGTH: 3385
<212> TYPE: DNA
<213> ORGANISM: Homo sapiens
<220> FEATURE:
<221> NAME/KEY: mRNA
<222> LOCATION: (1)..(3385)
<223> OTHER INFORMATION: Protein kinae 3

<400> SEQUENCE: 1
ggctcccgcg ggcgcgcggc ggggaaggcc agaggacctg ggcgcgggcg atgtgcctcc        60
tgagcgtcca aaccggggt gaggcgcggt cacgcccagc gggaaccgca ggcgccgaag       120
cccgggtact gggcccagaa tcccgcggaa ttttggatcc gagggaggcg ctgggcgcg       180 ggacctcggg cgtggggtcc cgggcgctgg atcggcgcgg acgggaggcg gcgctggtcc       240
cgcgggccag cgggtctcgg gaggggcgc ccgatcccgc gtctccggcg ccgcttcccg       300
ggaagtttca agtttgaaag tcctggcgga gggtctgcgg cttccgggac cggagtggct       360
gagaggaggg ccccaagcgg ccggagcggc gccatggagg aggggcgcc gcggcagcct       420 gggccgagcc agtggccccc agaggatgag aaggaggtga tccgccgggc catccagaaa       480
gagctgaaga tcaaggaggg ggtggagaac ctgcggcgcg tggccacaga ccgccgccac       540
ttgggccatg tgcagcagct gctgcggtcc tccaaccgcc gcctggagca gctgcatggc       600
gagctgcggg agctgcacgc ccgaatcctg ctgcccggcc ctgggcctgg cccagctgag       660
cctgtggcct caggaccccg gccgtgggca gagcagctca gggctcggca cctagaggct       720
ctccggaggc agctgcatgt ggagctgaag gtgaagcagg gggctgagaa catgacccac       780
acgtgcgcca gtggcacccc caaggagagg aagctcctgg cagctgccca gcagatgctg       840
cgggacagcc agctgaaggt ggccctgctg cggatgaaga tcagcagcct ggaggccagt       900
gggtccccgg agccagggcc tgagctgctg gcggaggagc tacagcatcg actgcacgtt       960
gaggcagctg tggctgaggg cgccaagaac gtggtgaaac tgcttagtag ccggagaaca      1020
caggaccgca aggcactggc tgaggcccag gcccagctac aggagtcctc tcagaaactg      1080
gacctcctgc gcctggcctt ggagcagctg ctggagcaac tgcctcctgc ccacccttg      1140 cgcagcagag tgacccgaga gttgcgggct gcggtgcctg gataccccca gccttcaggg      1200
acacctgtga agcccaccgc cctaacaggg acactgcagg tccgcctcct gggctgtgaa      1260
cagttgctga cagccgtgcc tgggcgctcc ccagcggccg cactggccag cagcccctcc      1320
gagggctggc ttcggaccaa ggccaagcac cagcgtggcc gaggcgagct tgccagcgag      1380
gtgctggctg tgctaaaggt ggacaaccgt gttgtgggc agacgggctg ggggcaggtg      1440
gccgaacagt cctgggacca gacctttgtc atcccactgg agcgagcccg tgagctggag      1500
attggggtac actggcggga ctggcggcag ctatgtggcg tggccttcct gagacttgag      1560
gacttcctgg acaatgcctg tcaccaactg tccctcagcc tggtaccgca gggactgctt      1620
tttgcccagg tgaccttctg cgatcctgtc attgagaggc ggccccggct gcagaggcag      1680
gaacgcatct tctctaaacg cagaggccag gacttcctga gggcttcgca gatgaacctc      1740 ggcatggcg cctgggggcg cctcgtcatg aacctgctgc ccccctgcag ctccccgagc      1800
acaatcagcc ccctaaagg atgccctcgg accccaacaa cactgcgaga ggcctctgac      1860
```

```
cctgccactc ccagtaattt cctgcccaag aagacccccct tgggtgaaga gatgacaccc      1920
ccacccaagc ccccacgcct ctacctcccc caggagccaa catccgagga gactccgcgc      1980
accaaacgtc cccatatgga gcctaggact cgacgtgggc catctccacc agcctccccc      2040
accaggaaac cccctcggct tcaggacttc cgctgcttag ctgtgctggg ccggggacac      2100
tttgggaagg tcctcctggt ccagttcaag gggacaggga aatactacgc catcaaagca      2160
ctgaagaagc aggaggtgct cagccgggac gagatagaga gcctgtactg cgagaagcgg      2220
atcctggagg ctgtgggctg cacagggcac cctttcctgc tctccctcct tgcctgcttc      2280
cagacctcca gccatgcctg ctttgtgact gagtttgtgc ctggtggtga cctcatgatg      2340
cagatccacg aggatgtctt ccccgagccc caggcccgct tctacgtggc ttgtgttgtc      2400
ctggggctgc agttcttaca cgagaagaag atcatttaca gggacctgaa gttggataac      2460
cttctgctgg atgcccaggg attcctgaag atcgcagact ttggactctg caaggaaggg      2520
atcggcttcg gggaccggac tagcaccttc tgtggcaccc cggagttcct ggctcccgag      2580
gtgctgaccc aggaggcata cacacgggct gtggactggt gggggctggg tgtgctgctc      2640
tacgagatgc tggtgggtga gtgcccgttc ccaggggaca cagaggaaga ggtgtttgac      2700
tgcatcgtca acatggacgc ccctacccc ggctttctgt cggtgcaagg gcttgagttc      2760
attcagaagc tcctccagaa gtgcccggag aagcgcctcg gggcaggtga gcaggatgcc      2820
gaggagatca aggtccagcc attcttcagg accaccaact ggcaagccct gctcgcccgc      2880
accatccagc ccccccttcgt gcctaccctg tgtggccctg cggacctgcg ctactttgag      2940
ggcgagttca cagggctgcc gcctgccctg accccacctg caccccacag cctcctcact      3000
gcccgccaac aggccgcctt ccgggacttc gactttgtgt cagagcgatt cctggaaccc      3060
tgagggcatc tcctggcacc tctgtcccct tcccccacag actgttagag cctctgctcg      3120 ttcaccgtg cgcccctgcct ggaggtccag gccttgctgg gtacttctga gcccttggga     3180
ttcaaagtgg cagccatggg gccactgttg tgggctttgc tcagtgtcac tgggcaaagt      3240
gtgtcccttc cccctccagc tcgccctctt ctacctccca gcgagacctg cccagaaag      3300 ggtgccgcag caaggagtga tatggttttgt cttttttaaga ctggacttgc tttatattaa    3360
atttgtaaaa gtgtgcaaaa aaaaa                                           3385
```

<210> SEQ ID NO 2
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 2
agcugaagau caaggaggg                                                    19

<210> SEQ ID NO 3
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 3
cccuccuuga ucuucagcu                                                    19

```
<210> SEQ ID NO 4
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 4
cuugaggacu uccuggaca                                              19

<210> SEQ ID NO 5
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 5
uguccaggaa guccucaag                                              19

<210> SEQ ID NO 6
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 6
uugaggacuu ccuggacaa                                              19

<210> SEQ ID NO 7
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 7
uuguccagga aguccucaa                                              19

<210> SEQ ID NO 8
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 8
aggacuuccu ggacaaugc                                              19

<210> SEQ ID NO 9
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 9
gcauugucca ggaaguccu                                              19

<210> SEQ ID NO 10
<211> LENGTH: 19
```

```
<212> TYPE: RNA
<213> ORGANISM: Artificial
<220> FEATURE:
<221> NAME/KEY: misc_feature
<223> OTHER INFORMATION: synthetic

<400> SEQUENCE: 10
ccuggacaau gccugucac                                                   19

<210> SEQ ID NO 11
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 11
gugacaggca uuguccagg                                                   19

<210> SEQ ID NO 12
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 12
gggacacuuu gggaagguc                                                   19

<210> SEQ ID NO 13
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 13
gaccuuccca aaguguccc                                                   19

<210> SEQ ID NO 14
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 14
uugggaaggu ccuccuggu                                                   19

<210> SEQ ID NO 15
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 15
accaggagga ccuucccaa                                                   19

<210> SEQ ID NO 16
<211> LENGTH: 19
<212> TYPE: RNA
<213> ORGANISM: Artificial
```

```
<220> FEATURE:
<221> NAME/KEY: misc_feature
<223> OTHER INFORMATION: synthetic

<400> SEQUENCE: 16
cuccagccau gccugcuuu                                                     19

<210> SEQ ID NO 17
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 17
aaagcaggca uggcuggag                                                     19

<210> SEQ ID NO 18
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 18
auucagaagc uccuccaga                                                     19

<210> SEQ ID NO 19
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 19
ucuggaggag cuucugaau                                                     19

<210> SEQ ID NO 20
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 20
ucagaagcuc cuccagaag                                                     19

<210> SEQ ID NO 21
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 21
cuucuggagg agcuucuga                                                     19

<210> SEQ ID NO 22
<211> LENGTH: 19
<212> TYPE: RNA
<213> ORGANISM: Artificial
<220> FEATURE:
<221> NAME/KEY: misc_feature
```

<223> OTHER INFORMATION: synthetic

<400> SEQUENCE: 22
cagaagcucc uccagaagu                                                19

<210> SEQ ID NO 23
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 23
acuucuggag gagcuucug                                                19

<210> SEQ ID NO 24
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 24
ucuucaggac caccaacug                                                19

<210> SEQ ID NO 25
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 25
caguuggugg uccugaaga                                                19

<210> SEQ ID NO 26
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 26
cuucaggacc accaacugg                                                19

<210> SEQ ID NO 27
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 27 ccaguggug guccugaag                                                 19

<210> SEQ ID NO 28
<211> LENGTH: 19
<212> TYPE: RNA
<213> ORGANISM: Artificial
<220> FEATURE:
<221> NAME/KEY: misc_feature
<223> OTHER INFORMATION: synthetic -continued

```
<400> SEQUENCE: 28
ucaggaccac caacuggca                                                  19

<210> SEQ ID NO 29
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 29
ugccaguugg ugguccuga                                                  19

<210> SEQ ID NO 30
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 30
agacuugagg acuuccugga caa                                             23

<210> SEQ ID NO 31
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 31
uuguccagga aguccucaag ucu                                             23

<210> SEQ ID NO 32
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 32
uugaggacuu ccuggacaau gcc                                             23

<210> SEQ ID NO 33
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 33
ggcauugucc aggaaguccu caa                                             23

<210> SEQ ID NO 34
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 34
```

-continued gacuugagga cuuccuggac aau                                          23

<210> SEQ ID NO 35
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 35
auuguccagg aaguccucaa guc                                          23

<210> SEQ ID NO 36
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 36
acuugaggac uuccuggaca aug                                          23

<210> SEQ ID NO 37
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 37
cauuguccag gaaguccuca agu                                          23

<210> SEQ ID NO 38
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 38
cuugaggacu uccuggacaa ugc                                          23

<210> SEQ ID NO 39
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 39
gcauugucca ggaaguccuc aag                                          23

<210> SEQ ID NO 40
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 40
ccauucuuca ggaccaccaa cug                                          23

```
<210> SEQ ID NO 41
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 41
caguuggugg uccugaagaa ugg                                              23

<210> SEQ ID NO 42
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 42
uucuucagga ccaccaacug gca                                              23

<210> SEQ ID NO 43
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 43
ugccaguugg ugguccugaa gaa                                              23

<210> SEQ ID NO 44
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 44
ucauucagaa gcuccuccag aag                                              23

<210> SEQ ID NO 45
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 45
cuucuggagg agcuucugaa uga                                              23

<210> SEQ ID NO 46
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 46
cacuuuggga agguccuccu ggu                                              23

<210> SEQ ID NO 47
```

```
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 47
accaggagga ccuucccaaa gug                                              23

<210> SEQ ID NO 48
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 48
cauucagaag cuccuccaga agu                                              23

<210> SEQ ID NO 49
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 49
acuucuggag gagcuucuga aug                                              23

<210> SEQ ID NO 50
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 50
ggcaccccca aggagaggaa gcu                                              23

<210> SEQ ID NO 51
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 51
agcuuccucu ccuuggggu gcc                                               23

<210> SEQ ID NO 52
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 52
cggggacacu uugggaaggu ccu                                              23

<210> SEQ ID NO 53
<211> LENGTH: 23
<212> TYPE: RNA
```

-continued

```
<213> ORGANISM: Artificial
<220> FEATURE:
<221> NAME/KEY: misc_feature
<223> OTHER INFORMATION: synthetic

<400> SEQUENCE: 53
aggaccuucc caaagugucc ccg                                              23

<210> SEQ ID NO 54
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 54
uccaaccgcc gccuggagca gcu                                              23

<210> SEQ ID NO 55
<211> LENGTH: 23
<212> TYPE: RNA
<213> ORGANISM: Artificial
<220> FEATURE:
<221> NAME/KEY: misc_feature
<223> OTHER INFORMATION: synthetic

<400> SEQUENCE: 55
agcugcucca ggcggcgguu gga                                              23

<210> SEQ ID NO 56
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 56
cguacgcgga auacuucga                                                   19

<210> SEQ ID NO 57
<211> LENGTH: 19
<212> TYPE: RNA
<213> ORGANISM: Artificial
<220> FEATURE:
<221> NAME/KEY: misc_feature
<223> OTHER INFORMATION: synthetic

<400> SEQUENCE: 57
ucgaaguauu ccgcguacg                                                   19
```

MEANS FOR INHIBITING THE EXPRESSION OF PROTEIN KINASE 3

CROSS-REFERENCE TO RELATED APPLICATION

This application is the U.S. national stage application of International Patent Application No. PCT/EP2007/006492, filed Jul. 20, 2007, the disclosure of which is hereby incorporated by reference in its entirety, including all figures, tables and amino acid or nucleic acid sequences.

The present invention is related to a double-stranded nucleic acid suitable to inhibit the expression of protein kinase 3 (PKN 3) and use thereof Oncogenesis was described by Foulds (Foulds, 1958) as a multistep biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (Fearon and Vogelstein, 1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

Cancer is fundamentally a genetic disease in which damage to cellular DNA leads to disruption of the normal mechanisms that control cellular proliferation. Two of the mechanisms of action by which tumor suppressors maintain genomic integrity is by cell arrest, thereby allowing for repair of damaged DNA, or removal of the damaged DNA by apoptosis (Ellisen and Haber, 1998). Apoptosis, otherwise called "programmed cell death," is a carefully regulated network of biochemical events which act as a cellular suicide program aimed at removing irreversibly damaged cells. Apoptosis can be triggered in a number of ways including binding of tumor necrosis factor, DNA damage, withdrawal of growth factors, and antibody cross-linking of Fas receptors. Although several genes have been identified that play a role in the apoptotic process, the pathways leading to apoptosis have not been fully elucidated. Many investigators have attempted to identify novel apoptosis-promoting genes with the objective that such genes would afford a means to induce apoptosis selectively in neoplastic cells to treat lancer in a patient. An alternative approach to treating cancer involves the suppression of angiogenesis with an agent such as Endostatin™ or anti-VEGF antibodies. In this approach, the objective is to prevent further vascularization of the primary tumor and potentially to constrain the size of metastatic lesions to that which can support neoplastic cell survival without substantial vascular growth.

A particular group of cancer diseases are those cancer diseases which are aggressive in terms of growth rate of the tumor, invasion into normal tissue, resistance to chemotherapy or other conventional treatments and the formation of metastasis throughout the body. In the case of more aggressive cancer, the cancer tissue is more different from the normal tissue and the tumor is more likely to spread. Therefore one objective in current cancer research is to develop agents which are inhibiting tumor growth and/or reducing the spreading of cancer cells throughout the body.

Definitions for what is an aggressive cancer disease may be taken from the homepage of the National Cancer Institute which is http://www.cancer.gov/Templates/db_alpha.aspx?CdrID=46053. Also, for the description of the agressivity of a cancer disease, typically grading is used which is a system for classifying cancer cells in terms of how abnormal they appear when examined under a microscope. The objective of a grading system is to provide information about the probable growth rate of the tumor and its tendency to spread. The systems used to grade tumors vary with each type of cancer. Grading plays a role in treatment decisions.

Such grading systems are known to the ones skilled in the art. One of them is the Gleason score which is a system of grading prostate cancer tissue based on how it looks under a microscope. Gleason scores range from 2 to 10 and indicate how likely it is that a tumor will spread. A low Gleason score means the cancer tissue is similar to normal prostate tissue and the tumor is less likely to spread; a high Gleason score means the cancer tissue is very different from normal and the tumor is more likely to spread.

PKN3 which is also referred to as protein kinase N beta or PKN beta, is a valuable target in connection with cancer and tumours. As described in international patent application WO 2004/019973 protein kinase N beta is a downstream target of the PI-3 kinase/PTEN pathway which is linked to tumorigenesis and metastasis. Particularly the latter effect seems to be strongly related to the loss of suppressor function, more particularly PTEN tumour suppressor function. As is shown in WO 2004/019973, protein kinase N beta will be up-regulated under conditions where PTEN which is an inhibitor to the PI-3 kinase pathway, is not active. Due to the up-regulation of protein kinase N beta the cells where such up-regulation occurs, will show an increase in metastatic behaviour and migrational behaviour. This means that an inhibitor of protein kinase N beta is a suitable means for controlling metastatic and migrational behaviour of cells and this is a suitable means for the treatment of tumors and cancers, more particularly those tumors and cancers which are metastatic and the cells of which show a metastatic and/or migrational behaviour.

There is an ongoing need in the art for means for the treatment of neoplastic diseases. There is more specifically a need for a means suitable for those neoplastic diseases which are aggressive and which show invasive behavior.

There is also a need for a mean suitable to affect angiogenesis, more specifically angiogenesis involved in the pathological mechanism underlying a neoplastic disease. These needs define the problem underlying the present invention.

The problem underlying the present invention is solved by the subject matter of the attached independent claims. Preferred embodiments may be taken from the dependent claims.

The problem underlying the present invention is solved by a double-stranded nucleic acid molecule,
    whereby the double-stranded structure comprises a first strand and a second strand,
    whereby the first strand comprises a first stretch of contiguous nucleotides and said first stretch is at least partially complementary to a target nucleic acid, and
    whereby the second strand comprises a second stretch of contiguous nucleotides and said second stretch is at least partially complementary to the first stretch, and
whereby the target nucleic acid is an mRNA coding for PKN3.

More specifically, the problem underlying the present invention is solved in a first aspect by a nucleic acid molecule comprising a double-stranded structure,
    whereby the double-stranded structure comprises a first strand and a second strand, whereby the first strand comprises a first stretch of contiguous nucleotides and said first stretch is at least partially complementary to a target nucleic acid, and whereby the second strand comprises a second stretch of contiguous nucleotides and said second stretch is at least partially complementary to the first stretch, whereby the first stretch comprises a nucleic acid sequence which is at least partially complementary to a nucleotide core sequence of the nucleic acid sequence according to SEQ. ID. No. 1 (NM_013355) or part thereof, whereby the nucleotide core sequence comprises the nucleotide sequence from nucleotide positions 482 to 500 of SEQ. ID. No. 1 (SEQ. ID. No. 2);

from nucleotide positions 1555 to 1573 of SEQ. ID. No. 1 (SEQ. ID. No. 4);

from nucleotide positions 1556 to 1574 of SEQ. ID. No. 1 (SEQ. ID. No. 6);

from nucleotide positions 1559 to 1577 of SEQ. ID. No. 1 (SEQ. ID. No. 8);

from nucleotide positions 1566 to 1584 of SEQ. ID. No. 1 (SEQ. ID. No. 10);

from nucleotide positions 2094 to 2112 of SEQ. ID. No. 1 (SEQ. ID. No. 12);

from nucleotide positions 2102 to 2120 of SEQ. ID. No. 1 (SEQ. ID. No. 14);

from nucleotide positions 2286 to 2304 of SEQ. ID. No. 1 (SEQ. ID. No. 16);

from nucleotide positions 2761 to 2779 of SEQ. ID. No. 1 (SEQ. ID. No. 18);

from nucleotide positions 2763 to 2781 of SEQ. ID. No. 1 (SEQ. ID. No. 20);

from nucleotide positions 2764 to 2782 of SEQ. ID. No. 1 (SEQ. ID. No. 22);

from nucleotide positions 2843 to 2861 of SEQ. ID. No. 1 (SEQ. ID. No. 24);

from nucleotide positions 2844 to 2862 of SEQ. ID. No. 1 (SEQ. ID. No. 26); or from nucleotide positions 2846 to 2864 of SEQ. ID. No. 1 (SEQ. ID. No. 28), preferably the nucleotide core sequence comprises the nucleotide sequence from nucleotide positions 1555 to 1573 of SEQ. ID. No. 1 (SEQ. ID. No. 4);

from nucleotide positions 1556 to 1574 of SEQ. ID. No. 1 (SEQ. ID. No. 6);

from nucleotide positions 1559 to 1577 of SEQ. ID. No. 1 (SEQ. ID. No. 8);

from nucleotide positions 1566 to 1584 of SEQ. ID. No. 1 (SEQ. ID. No. 10);

from nucleotide positions 2094 to 2112 of SEQ. ID. No. 1 (SEQ. ID. No. 12); or from nucleotide positions 2286 to 2304 of SEQ. ID. No. 1 (SEQ. ID. No. 16), whereby preferably the first stretch is additionally at least partially complementary to a region preceding the 5' end of the nucleotide core sequence and/or to a region following the 3' end of the nucleotide core sequence.

In an embodiment of the first aspect of the present invention the first stretch of the nucleic acid is complementary to the nucleotide core sequence or a part thereof.

In an embodiment of the first aspect of the present invention the first stretch of the nucleic acid is additionally complementary to the region following the 3' end of the nucleotide core sequence and/or to the region preceding the 5' end of the nucleotide core sequence.

In an embodiment of the first aspect of the present invention the first stretch of the nucleic acid is complementary to the target nucleic acid over 18 to 29 nucleotides, preferably 19 to 25 nucleotides and more preferably 19 to 23 nucleotides.

In a preferred embodiment of the first aspect of the present invention the nucleotides of the nucleic acid are consecutive nucleotides.

In an embodiment of the first aspect of the present invention, the first stretch and/or the second stretch of the nucleic acid comprises from 18 to 29 consecutive nucleotides, preferably 19 to 25 consecutive nucleotides and more preferably 19 to 23 consecutive nucleotides.

In an embodiment of the first aspect of the present invention the first strand of the nucleic acid consists of the first stretch and/or the second strand of the nucleic acid consists of the second stretch.

The problem underlying the present invention is solved in a second aspect by a nucleic acid molecule, preferably a nucleic acid molecule according to the first aspect, comprising a double-stranded structure, whereby the double-stranded structure is formed by a first strand and a second strand, whereby the first strand comprises a first stretch of contiguous nucleotides and the second strand comprises a second stretch of contiguous nucleotides and whereby said first stretch is at least partially complementary to said second stretch, whereby the first stretch consists of a nucleotide sequence according to SEQ. ID. No. 3 and the second stretch consists of a nucleotide sequence according to SEQ. ID. No. 2;

the first stretch consists of a nucleotide sequence according to SEQ. ID. No. 5 and the second stretch consists of a nucleotide sequence according to SEQ. ID. No. 4;

the first stretch consists of a nucleotide sequence according to SEQ. ID. No. 7 and the second stretch consists of a nucleotide sequence according to SEQ. ID. No. 6;

the first stretch consists of a nucleotide sequence according to SEQ. ID. No. 9 and the second stretch consists of a nucleotide sequence according to SEQ. ID. No. 8;

the first stretch consists of a nucleotide sequence according to SEQ. ID. No. 11 and the second stretch consists of a nucleotide sequence according to SEQ. ID. No. 10;

the first stretch consists of a nucleotide sequence according to SEQ. ID. No. 13 and the second stretch consists of a nucleotide sequence according to SEQ. ID. No. 12;

the first stretch consists of a nucleotide sequence according to SEQ. ID. No. 15 and the second stretch consists of a nucleotide sequence according to SEQ. ID. No. 14;

the first stretch consists of a nucleotide sequence according to SEQ. ID. No. 17 and the second stretch consists of a nucleotide sequence according to SEQ. ID. No. 16;

the first stretch consists of a nucleotide sequence according to SEQ. ID. No. 19 and the second stretch consists of a nucleotide sequence according to SEQ. ID. No. 18;

the first stretch consists of a nucleotide sequence according to SEQ. ID. No. 21 and the second stretch consists of a nucleotide sequence according to SEQ. ID. No. 20;

the first stretch consists of a nucleotide sequence according to SEQ. ID. No. 23 and the second stretch consists of a nucleotide sequence according to SEQ. ID. No. 22;

the first stretch consists of a nucleotide sequence according to SEQ. ID. No. 25 and the second stretch consists of a nucleotide sequence according to SEQ. ID. No. 24;

the first stretch consists of a nucleotide sequence according to SEQ. ID. No. 27 and the second stretch consists of a nucleotide sequence according to SEQ. ID. No. 26; or the first stretch consists of a nucleotide sequence according to SEQ. ID. No. 29 and the second stretch consists of a nucleotide sequence according to SEQ. ID. No. 28;

the first stretch consists of a nucleotide sequence according to SEQ. ID. No. 31 and the second stretch consists of a nucleotide sequence according to SEQ. ID. No. 30;

the first stretch consists of a nucleotide sequence according to SEQ. ID. No. 33 and the second stretch consists of a nucleotide sequence according to SEQ. ID. No. 32;

the first stretch consists of a nucleotide sequence according to SEQ. ID. No. 35 and the second stretch consists of a nucleotide sequence according to SEQ. ID. No. 34;

the first stretch consists of a nucleotide sequence according to SEQ. ID. No. 37 and the second stretch consists of a nucleotide sequence according to SEQ. ID. No. 36;

the first stretch consists of a nucleotide sequence according to SEQ. ID. No. 39 and the second stretch consists of a nucleotide sequence according to SEQ. ID. No. 38;

preferably the first stretch consists of a nucleotide sequence according to SEQ. ID. No. 5 and the second stretch consists of a nucleotide sequence according to SEQ. ID. No. 4;

the first stretch consists of a nucleotide sequence according to SEQ. ID. No. 7 and the second stretch consists of a nucleotide sequence according to SEQ. ID. No. 6;

the first stretch consists of a nucleotide sequence according to SEQ. ID. No. 9 and the second stretch consists of a nucleotide sequence according to SEQ. ID. No. 8;

the first stretch consists of a nucleotide sequence according to SEQ. ID. No. 11 and the second stretch consists of a nucleotide sequence according to SEQ. ID. No. 10;

the first stretch consists of a nucleotide sequence according to SEQ. ID. No. 13 and the second stretch consists of a nucleotide sequence according to SEQ. ID. No. 12;

the first stretch consists of a nucleotide sequence according to SEQ. ID. No. 17 and the second stretch consists of a nucleotide sequence according to SEQ. ID. No. 16, or the first stretch consists of a nucleotide sequence according to SEQ. ID. No. 31 and the second stretch consists of a nucleotide sequence according to SEQ. ID. No. 30;

In an embodiment of the first and the second aspect of the present invention the first stretch and/or the second stretch of the nucleic acid molecule comprises a plurality of groups of modified nucleotides having a modification at the 2' position forming a regular, preferably alternating, positional pattern, whereby within the stretch each group of modified nucleotides is flanked on one or both sides by a flanking group of nucleotides, whereby the flanking nucleotide(s) forming the flanking group of nucleotides is/are either an unmodified nucleotide or a nucleotide having a modification different from the modification of the modified nucleotides.

In an embodiment of the first and the second aspect of the present invention the first stretch of the nucleic acid and/or the second stretch of the nucleic acid comprises a pattern of groups of modified nucleotides and/or a pattern of flanking groups of nucleotides.

In an embodiment of the first and the second aspect of the present invention the first stretch of the nucleic acid and/or the second stretch of the nucleic acid comprise at the 3' end a dinucleotide, whereby such dinucleotide is preferably TT.

In a preferred embodiment of the first and the second aspect of the present invention the length of the first stretch of the nucleic acid and/or of the second stretch of the nucleic acid consists of 19 to 21 nucleotides.

In an embodiment of the first and the second aspect of the present invention the first and/or the second stretch of the nucleic acid comprise an overhang of 1 to 5 nucleotides at the 3' end.

In a preferred embodiment of the first and the second aspect of the present invention the length of the double-stranded structure of the nucleic acid is from about 16 to 24 nucleotide pairs, preferably 20 to 22 nucleotide pairs.

In an embodiment of the first and the second aspect of the present invention the first strand of the nucleic acid and the second strand of the nucleic acid are covalently linked to each other, preferably the 3' end of the first strand is covalently linked to the 5' end of the second strand.

In an embodiment of the first and the second aspect of the present invention the molecule of the nucleic acid consists of each of the two following strands and whereby the underlined nucleotides are 2'-O-methyl:

```
PKN3 (1):
agcugaagaucaaggaggg      (SEQ. ID. No. 2)
cccuccuugaucuucagcu      (SEQ. ID. No. 3)

PKN3 (2):
cuugaggacuuccuggaca      (SEQ. ID. No. 4)
uguccaggaaguccucaag      (SEQ. ID. No. 5)

PKN3 (3):
uugaggacuuccuggacaa      (SEQ. ID. No. 6)
uuguccaggaaguccucaa      (SEQ. ID. No. 7)

PKN3 (4):
aggacuuccuggacaaugc      (SEQ. ID. No. 8)
gcauuguccaggaaguccu      (SEQ. ID. No. 9)

PKN3 (5):
ccuggacaaugccugucac      (SEQ. ID. No. 10)
gugacaggcauuguccagg      (SEQ. ID. No. 11)

PKN3 (6):
gggacacuuugggaagguc      (SEQ. ID. No. 12)
gaccuucccaaagugucc       (SEQ. ID. No. 13)

PKN3 (7):
uugggaagguccuccuggu      (SEQ. ID. No. 14)
accaggaggaccuucccaa      (SEQ. ID. No. 15)

PKN3 (8):
cuccagccaugccugcuuu      (SEQ. ID. No. 16)
aaagcaggcaugcuggag       (SEQ. ID. No. 17)

PKN3 (9):
auucagaagcuccuccaga      (SEQ. ID. No. 18)
ucuggaggagcuucugaau      (SEQ. ID. No. 19)

PKN3 (10):
ucagaagcuccuccagaag      (SEQ. ID. No. 20)
cuucuggaggagcuucuga      (SEQ. ID. No. 21)

PKN3 (11):
cagaagcuccuccagaagu      (SEQ. ID. No. 22)
acuucuggaggagcuucug      (SEQ. ID. No. 23)

PKN3 (12):
ucuucaggaccaccaacug      (SEQ. ID. No. 24)
caguuggugguccugaaga      (SEQ. ID. No. 25)

PKN3 (13):
cuucaggaccaccaacugg      (SEQ. ID. No. 26)
ccaguuggugguccugaag      (SEQ. ID. No. 27)

PKN3 (14):
ucaggaccaccaacuggca      (SEQ. ID. No. 28)
ugccaguuggugguccuga      (SEQ. ID. No. 29)

PKN3-23-v1:
uuguccaggaaguccucaagucu  (SEQ. ID. No. 31)
agacuugaggacuuccuggacaa  (SEQ. ID. No. 30)

PKN3-23-v2:
ggcauuguccaggaaguccucaa  (SEQ. ID. No. 33)
uugaggacuuccuggacaaugcc  (SEQ. ID. No. 32)

PKN3-23-v3:
auuguccaggaaguccucaaguc  (SEQ. ID. No. 35)
```

```
                    -continued
    gacuugaggacuuccuggacaau    (SEQ. ID. No. 34)

PKN3-23-v4:
    cauuguccaggaaguccucaagu    (SEQ. ID. No. 37)
    acuugaggacuuccuggacaaug    (SEQ. ID. No. 36)

PKN3-23-v5:
    gcauuguccaggaaguccucaag    (SEQ. ID. No. 39)
    cuugaggacuuccuggacaaugc    (SEQ. ID. No. 38)
    preferably PKN3 (2):
    cuugaggacuuccuggaca        (SEQ. ID. No. 4)
    uguccaggaaguccucaag        (SEQ. ID. No. 5)

PKN3 (3):
    uugaggacuuccuggacaa        (SEQ. ID. No. 6)
    uuguccaggaaguccucaa        (SEQ. ID. No. 7)

PKN3 (4):
    aggacuuccuggacaaugc        (SEQ. ID. No. 8)
    gcauuguccaggaaguccu        (SEQ. ID. No. 9)

PKN3 (5):
    ccuggacaaugccugucac        (SEQ. ID. No. 10)
    gugacaggcauuguccagg        (SEQ. ID. No. 11)

PKN3 (6):
    gggacacuuugggaagguc        (SEQ. ID. No. 12)
    gaccuuccaaaguguccc         (SEQ. ID. No. 13)

PKN3 (8):
    cuccagccaugccugcuuu        (SEQ. ID. No. 16)
    aaagcaggcauggcuggag        (SEQ. ID. No. 17)

PKN3-23-v1:
    uuguccaggaaguccucaagucu    (SEQ. ID. No. 31)
    agacuugaggacuuccuggacaa    (SEQ. ID. No. 30)
```

The problem underlying the present invention is solved in a third aspect by a liposomal formulation comprising a nucleic acid according to the first or the second aspect.

The problem underlying the present invention is solved in a fourth aspect by a lipoplex comprising a nucleic acid according to the first or the second aspect, and a liposome.

In a preferred embodiment of the fourth aspect of the present invention the liposome of the lipoplex consists of
a) about 50 mol % β-arginyl-2,3-diaminopropionic acid-N-palmityl-N-oleyl-amide trihydrochloride, preferably (β-(L-arginyl)-2,3-L-diaminopropionic acid-N-palmityl-N-oleyl-amide tri-hydrochloride);
b) about 48 to 49 mol % 1,2-diphytanoyl-sn-glycero-3-phosphoethanolamine (DPhyPE); and
c) about 1 to 2 mol % 1,2-distearoyl-sn-glycero-3-phosphoethanolamine-polyethylen-glycole, preferably N-(Carbonyl-methoxypolyethyleneglycol-2000)-1,2-distearoyl-sn-glycero-3-phosphoethanolamine sodium salt.

In a more preferred embodiment of the fourth aspect of the present invention the zeta-potential of the lipoplex is about 35 to 60 mV, preferably about 45 to 50 mV.

In an embodiment of the fourth aspect of the present invention the lipoplex has a size of about 50 to 400 nm, preferably of about 100 to 140 nm, and more preferably of about 110 nm to 130 nm, as determined by QELS.

The problem underlying the present invention is solved in a fifth aspect by a vector, preferably an expression vector, comprising or coding for a nucleic acid according to the first and the second aspect.

The problem underlying the present invention is solved in a sixth aspect by a cell comprising a nucleic acid according to any of the preceding aspects or vector according to any of the preceding aspects.

The problem underlying the present invention is solved in a seventh aspect by a composition, preferably a pharmaceutical composition, comprising a nucleic acid according to the first or the second aspect, a liposomal formulation according to the third aspect, a lipoplex according to the fourth aspect, a vector according to the fifth aspect and/or a cell according to the sixth aspect.

In a preferred embodiment of the seventh aspect of the present invention the composition is a pharmaceutical composition optionally further comprising a pharmaceutically acceptable vehicle.

In a more preferred embodiment of the seventh aspect of the present invention the composition is a pharmaceutical composition and said pharmaceutical composition is for the treatment of an angiogenesis-dependent disease, preferably a diseases characterized or caused by insufficient, abnormal or excessive angiogenesis.

In a most preferred embodiment of the seventh aspect of the present invention the angiogenesis of the composition is angiogenesis of adipose tissue, skin, heart, eye, lung, intestines, reproductive organs, bone and joints.

In an embodiment of the seventh aspect of the present invention the disease is selected from the group comprising infectious diseases, autoimmune disorders, vascular malformation, atherosclerosis, transplant arteriopathy, obesity, psoriasis, warts, allergic dermatitis, persistent hyperplastic vitreous syndrome, diabetic retinopathy, retinopathy of prematurity, age-related macular disease, choroidal neovascularization, primary pulmonary hypertension, asthma, nasal polyps, inflammatory bowel and periodontal disease, ascites, peritoneal adhesions, endometriosis, uterine bleeding, ovarian cysts, ovarian hyperstimulation, arthritis, synovitis, osteomyelitis, osteophyte formation.

In an embodiment of the seventh aspect of the present invention the pharmaceutical composition is for the treatment of a neoplastic disease, preferably a cancer disease, and more preferably a solid tumor.

In an embodiment of the seventh aspect of the present invention the pharmaceutical composition is for the treatment of a disease selected from the group comprising bone cancer, breast cancer, prostate cancer, cancer of the digestive system, colorectal cancer, liver cancer, lung cancer, kidney cancer, urogenital cancer, pancreatic cancer, pituitary cancer, testicular cancer, orbital cancer, head and neck cancer, cancer of the central nervous system and cancer of the respiratory system.

The problem underlying the present invention is solved in an eighth aspect by use of a nucleic acid according to the first or the second aspect, of a liposomal formulation according to the third aspect, of a lipoplex according to the fourth aspect, of a vector according to the fifth aspect and/or a cell according to the sixth aspect for the manufacture of a medicament.

In an embodiment of the eighth aspect of the present invention the medicament is used for the treatment of any of the diseases as defined in connection with the seventh aspect of the present invention.

In a preferred embodiment of the eighth aspect of the present invention the medicament is used in combination with one or several other therapies.

In a more preferred embodiment of the eighth aspect of the present invention the therapy is selected from the group comprising chemotherapy, cryotherapy, hyperthermia, antibody therapy, radiation therapy and anti-angiogenesis therapy.

In a most preferred embodiment of the eighth aspect of the present invention the therapy is antibody therapy and more preferably an antibody therapy using an anti-VEGF antibody (such as, e.g., the one provided by Genentech-Roche and marketed under the name of Avastin) or anti-angiopoetin antibody.

In an embodiment of the eighth aspect of the present invention the anti-angiogenesis therapy uses a kinase receptor inhibitor, preferably a tyrosine kinase receptor inhibitor, whereby such receptor is selected from the group comprising VEGF receptor, PDGF receptor, Tie-2, FGFR and EGFR. Examples for such kind of inhibitor are Sorafenib (Bayer) targeting VEGF-R and PDGF-R, and the antibody Erbitux (Merck/serono) targeting EGFR. Both medicaments are regarded as anti-angiogenic modalities.

In a preferred embodiment of the eighth aspect of the present invention the inhibitor is selected from the group comprising siRNA, antisense molecules, aptamers, spiegelmers, high affinity binding peptides, peptide aptamers, anticalines and antibodies.

In a preferred embodiment of the eighth aspect the medicament is used in combination with one or several other therapies, preferably anti-tumor or anti-cancer therapies.

In a more preferred embodiment of the eighth aspect the therapy is selected from the group comprising chemotherapy, cryotherapy, hyperthermia, antibody therapy and radiation therapy.

In an even more preferred embodiment of the eighth aspect the therapy is an antiagiogenic therapy and more preferably an antibody therapy using an anti-VEGF or anti-angiopoetin antibody.

In a further preferred embodiment of the various aspects of the present invention the mRNA is a human mRNA of PKN3. In an even more preferred embodiment the target nucleic acid is an mRNA having a nucleic acid sequence in accordance with SEQ. ID. No. 1.

As will be outlined in more detail herein, the nucleic acid molecules and the medicament and formulation, respectively, containing the same, are particularly suitable to inhibit, or prevent or treat invasive cancer, aggressive cancer and malignancies.

As preferably used herein, an invasive cancer is a cancer that has spread beyond the layer of tissue in which it developed and is growing into surrounding, healthy tissues. Also called infiltrating cancer.

As preferably used herein, an aggressive cancer is a quickly growing cancer.

As preferably used herein, a malignancy is a cancerous tumor that can invade and destroy nearby tissue and spread to other parts of the body.

It is to be acknowledged by the ones skilled in the art that there may be one or several single nucleotide changes in the mRNA in various individuals or groups of individuals, preferably in a population, compared to the mRNA having the nucleotide sequence of SEQ. ID. No. 1. Such mRNA having one or several single nucleotide changes compared to the mRNA having a nucleic acid sequence of SEQ. ID. No 1 shall also be comprised by the term target nucleic acid as preferably used herein. In a still further embodiment the nucleic acid molecule according to the various aspects of the invention is suitable to inhibit the expression of PKN3 and the mRNA coding thereof. More preferably such expression is inhibited by a mechanism which is referred to as RNA interference or post-transcriptional gene silencing. The siRNA molecule and RNAi molecule respectively, according to the present invention is thus suitable to trigger the RNA interference response resulting preferably in the knock-down of the mRNA for the target molecule. Insofar, this kind of nucleic acid molecule is suitable to decrease the expression of a target molecule by decreasing the expression at the level of mRNA.

It will be acknowledged by the one skilled in the art that there may be further mRNAs coding for PKN3 which shall also be encompassed by the present application. More specifically, the particular nucleotide positions identified herein by reference to SEQ. ID. No. 1 can be identified in such further mRNAs by the one skilled in the art based on the technical teaching provided herein.

It is also to be acknowledged that the double-stranded nucleic acid according to this aspect of the present invention may have any of the designs described herein for this kind of nucleic acid molecule. It is furthermore to be acknowledged that the mechanism described above is, in a preferred embodiment also applicable to the nucleic acids disclosed herein in connection with the various aspects and design principles also referred to herein as sub-aspects.

RNA interference refers to the process of sequence specific post-transcriptional gene silencing in animals mediated by short interfering RNAs (siRNAs) (Fire et al., 1998). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire, 1998 #263). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism which is also existing in animal cells and in particular also in mammalian cells, appears to be different from the interferon response that results from dsRNA-mediated activation of protein kinase PKR and 2',5'-oligoadenylate synthetase resulting in non-specific cleavage of mRNA by ribonuclease L.

The basic design of siRNA molecules or RNAi molecules, which mostly differ in the size, is basically such that the nucleic acid molecule comprises a double-stranded structure. The double-stranded structure comprises a first strand and a second strand. More preferably, the first strand comprises a first stretch of contiguous nucleotides and the second stretch comprises a second stretch of contiguous nucleotides. At least the first stretch and the second stretch are essentially complementary to each other. Such complementarity is typically based on Watson-Crick base pairing or other base-pairing mechanism known to the one skilled in the art, including but not limited to Hoogsteen base-pairing and others. It will be acknowledged by the one skilled in the art that depending on the length of such double-stranded structure a perfect match in terms of base complementarity is not necessarily required. However, such perfect complementarity is preferred in some embodiments. In a particularly preferred embodiment the complementarity and/or identity is at least 75%, 80%, 85%, 90% or 95%. In an alternative particularly preferred embodiment, the complementarity and/or identity is such that the complement and/or identical nucleic acid molecule hybridizes to one of the strands of the nucleic acid molecule according to the present invention, more preferably to one of the two stretches under the following conditions: is capable of hybridizing with a portion of the target gene transcript under the following conditions: 400 mM NaCl, 40 mM PIPES pH 6.4, 1 mM EDTA, 50° C. or 70° C. hybridisation for 12-16 hours, followed by washing. Respective reactions conditions are, among others described in European patent EP 1 230 375.

A mismatch is also tolerable, mostly under the proviso that the double-stranded structure is still suitable to trigger the RNA interference mechanism, and that preferably such double-stranded structure is still stably forming under physiological conditions as prevailing in a cell, tissue and organism, respectively, containing or in principle containing such cell, tissue and organ. More preferably, the double-stranded structure is stable at 37° C. in a physiological buffer. It will be acknowledged by the ones skilled in the art that this kind of mismatch can preferably be contained at a position within the nucleic acid molecule according to the present invention different from the core region.

As preferably used herein, the term that a nucleic acid molecule or a stretch or part thereof is partially complementary to a target nucleic acid molecule preferably means that if such target nucleic acid is either directly or indirectly targeted by a RNA interference (mediating) nucleic acid the complementarity between the target nucleic acid and said nucleic acid, stretch or part thereof, or the double-stranded structure formed because of such complementarity, is capable of triggering RNA interference. It will be understood that such complementarity requirement is not restricted to the RNA interference mechanism but any mechanism which results in the down-regulation or decrease in activity of a molecule such as a polypeptide encoded by the target nucleic acid. In one embodiment, the nucleic acid molecule which is partially complementary to another nucleic acid molecule comprises 1, 2, 3, 4 or 5 mismatches upon the base pairing of both nucleic acid molecules. More preferably the double-stranded nucleic acid molecule thus formed comprises 19 to 25 base pairs.

The first stretch is typically at least partially complementary or at least partially identical to a target nucleic acid and the second stretch is, particularly given the relationship between the first and second stretch, respectively, in terms of base complementarity, at least partially identical or at least partially complementary to the target nucleic acid. The target nucleic acid is preferably an mRNA, although other forms of RNA such as hnRNAs are also suitable for the purpose of the nucleic acid molecule as disclosed herein. As preferably used herein the target is PKN3 and the target nucleic acid is more preferably the DNA or RNA which codes for PKN3, or a part thereof provided that such part still has preferably at least the characteristic of the full-length PKN3 to act as a kinase.

Although RNA interference can be observed upon using long nucleic acid molecules comprising several dozens and sometimes even several hundreds of nucleotides and nucleotide pairs, respectively, shorter RNAi molecules are generally preferred. A more preferred range for the length of the first stretch and/or second stretch is from about 18 to 29 consecutive nucleotides, preferably 19 to 25 consecutive nucleotides and more preferably 19 to 23 consecutive nucleotides. More preferably, both the first stretch and the second stretch have the same length. In a further embodiment, the double-stranded structure comprises preferably between 16 and 29, preferably 18 to 25, more preferably 19 to 23 and most preferably 19 to 21 base pairs.

Although in accordance with the present invention, in principle, any part of the mRNA coding for PKN3 can be used for the design of such siRNA molecule and RNAi molecule, respectively, the present inventors have surprisingly found that the sequence starting with nucleotide positions 1555, 1556, 1559, 1566, 2094, 2286 of the mRNA of SEQ. ID. No. 1 having the nucleotide sequence of SEQ. ID. No. 1 are particularly suitable to be addressed by RNA interference mediating molecule(s).

More specifically, the present inventors have surprisingly found that although these sequences and starting points are particularly preferred target sequence for expression inhibition of PKN3, there is a core of nucleotides in the vicinity of these sequences which is particularly effective insofar. This core is in one embodiment a sequence consisting of the about 9 to 11 last nucleotides of the above specified nucleotide sequences. Starting therefrom, the core can be extended such that a functionally active double-stranded nucleic acid molecule is obtained, whereby preferably functionally active means suitable to affect expression inhibition of PKN3. For such purpose, the second stretch which is essentially identical to the corresponding part of the mRNA, i.e. the core sequence, is thus prolonged by one, preferably several nucleotides at the 5' end, whereby the thus added nucleotides are essentially identical to the nucleotides present in the target nucleic acid at the corresponding positions. Also for such purpose, the first strand which is essentially complementary to the target nucleic acid, is thus prolonged by one, preferably several nucleotides at the 3' end, whereby the thus added nucleotides are essentially complementary to the nucleotides present in the target nucleic acid at the corresponding positions, i.e. at the 5' end.

In accordance with this design principle, the core sequences according to the present invention can be summarized as follows:

```
PKN3 (2):  cuugaggacuuccuggaca    (SEQ. ID. No. 4)
           uguccaggaaguccucaag    (SEQ. ID. No. 5)

PKN3 (3):  uugaggacuuccuggacaa    (SEQ. ID. No. 6)
           uuguccaggaaguccucaa    (SEQ. ID. No. 7)

PKN3 (4):  aggacuuccuggacaaugc    (SEQ. ID. No. 8)
           gcauuguccaggaaguccu    (SEQ. ID. No. 9)

PKN3 (5):  ccuggacaaugccugucac    (SEQ. ID. No. 10)
           gugacaggcauuguccagg    (SEQ. ID. No. 11)

PKN3 (6):  gggacacuuugggaagguc    (SEQ. ID. No. 12)
           gaccuucccaaaguguccc    (SEQ. ID. No. 13)

PKN3 (8):  cuccagccaugccugcuuu    (SEQ. ID. No. 16)
           aaagcaggcaugcuggag     (SEQ. ID. No. 17)
```

More preferably, the above strand of each double-stranded molecule is, in this representation, the sense strand, whereas the lower strand is the antisense strand, both depicted in 5'->3' direction. Even more preferably, in the sense strand every second nucleotide starting with the second nucleotide is modified at the 2' position to preferably be a 2'-O-Me modified nucleotide and in the antisense strand every second nucleotide starting with the first nucleotide is modified at the 2' position to preferably be a 2'-O-Me modified nucleotide. This kind of modification or regular or spatial modification pattern can be realized in preferred embodiments on any nucleic acid molecule according to the present invention.

In a further embodiment thereof, the core sequence is identical to the nucleotide sequence of the second stretch of the double-stranded nucleic acid molecule according to the present invention and the first stretch essentially complementary thereto. In a still further preferred embodiment, the length of the double-stranded nucleic acid molecule according to the present invention is within the limits disclosed herein in connection with the various aspects and sub-aspects, respectively.

It will be acknowledged by the ones skilled in the art that the particular design of the siRNA molecules and the RNAi molecules, respectively, can vary in accordance with the current and future design principles. For the time being some design principles exist which shall be discussed and disclosed in more detail in the following and which shall be referred to as sub-aspects or sub-aspects of the first aspect of the nucleic acid molecule according to the present invention. It is within the present invention that all features and embodiments described for one particular sub-aspect, i.e. design of the nucleic acid, are also applicable to any other aspect and sub-aspect of the nucleic acid according to the present invention and thus form respective embodiments thereof.

The first sub-aspect is related to nucleic acid according to the present invention, whereby the first stretch comprises a plurality of groups of modified nucleotides having a modification at the 2' position, whereby within the stretch each group of modified nucleotides is flanked on one or both sides by a flanking group of nucleotides, whereby the flanking nucleotide(s) forming the flanking group(s) of nucleotides is either an unmodified nucleotide or a nucleotide having a modification different from the modification of the modified nucleotides. Such design is, among others described in international patent application WO 2004/015107. The nucleic acid according to this aspect is preferably a ribonucleic acid although, as will be outlined in some embodiments, the modification at the 2' position results in a nucleotide which as such is, from a pure chemical point of view, no longer a ribonucleotide. However, it is within the present invention that such modified ribonucleotide shall be regarded and addressed herein as a ribonucleotide and the molecule containing such modified ribonucleotide as a ribonucleic acid.

In an embodiment of the ribonucleic acid according to the first sub-aspect of the present invention the ribonucleic acid is blunt ended, either on one side or on both sides of the double-stranded structure. In a more preferred embodiment the double-stranded structure comprises or consists of 18 to 25, preferably 18 to 23 and more preferably 19, 21 or 23 base pairs, whereby such double-stranded structure is preferably blunt ended. In a still even more preferred embodiment, the nucleic acid consists of the first stretch and the second stretch only.

In a further embodiment of the ribonucleic acid according to the first sub-aspect of the present invention said first stretch and/or said second stretch comprise a plurality of groups of modified nucleotides. In a further preferred embodiment the first stretch also comprises a plurality of flanking groups of nucleotides. In a preferred embodiment a plurality of groups means at least two groups.

In another embodiment of the ribonucleic acid according to the first sub-aspect of the present invention said second stretch comprises a plurality of groups of modified nucleotides. In a further preferred embodiment the second stretch also comprises a plurality of flanking groups of nucleotides. In a preferred embodiment a plurality of groups means at least two groups.

In a further preferred embodiment both the first and the second stretch comprise a plurality of both groups of modified nucleotides and flanking groups of nucleotides. In a more preferred embodiment the plurality of both groups of modified nucleotides and flanking groups of nucleotides form a pattern, preferably a regular and/or a repeating pattern, on either the first stretch and/or the second stretch, whereby it is even more preferred that such pattern is formed on both the first and the second stretch.

In a preferred embodiment of the ribonucleic acid according to the first sub-aspect of the present invention the group of modified nucleotides and/or the group of flanking nucleotides comprises a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

In another embodiment of the ribonucleic acid according to the first sub-aspect of the present invention the pattern of modified nucleotides of said first stretch is the same as the pattern of modified nucleotides of said second stretch.

In a preferred embodiment of the ribonucleic acid according to the first sub-aspect of the present invention the pattern of said first stretch aligns with the pattern of said second stretch.

In an alternative embodiment of the ribonucleic acid according to the first sub-aspect of the present invention the pattern of said first stretch is shifted by one or more nucleotides relative to the pattern of the second stretch.

In an embodiment of the ribonucleic acid according to the first sub-aspect of the present invention the modification at the 2' position is selected from the group comprising amino, fluoro, methoxy, alkoxy and alkyl.

In another embodiment of the ribonucleic acid according to the first sub-aspect of the present invention the double stranded structure is blunt ended.

In a preferred embodiment of the ribonucleic acid according to the first sub-aspect of the present invention the double stranded structure is blunt ended on both sides of the double-stranded structure.

In another embodiment of the ribonucleic acid according to the first sub-aspect of the present invention the double stranded structure is blunt ended on the double stranded structure's side which is defined by the 5'-end of the first strand and the 3'-end of the second strand.

In still another embodiment of the ribonucleic acid according to the first sub-aspect of the present invention the double stranded structure is blunt ended on the double stranded structure's side which is defined by at the 3'-end of the first strand and the 5'-end of the second strand.

In another embodiment of the ribonucleic acid according to the first sub-aspect of the present invention at least one of the two strands has an overhang of at least one nucleotide at the 5'-end.

In a preferred embodiment of the ribonucleic acid according to the first sub-aspect of the present invention the overhang consists of at least one deoxyribonucleotide.

In a further embodiment of the ribonucleic acid according to the first sub-aspect of the present invention at least one of the strands has an overhang of at least one nucleotide at the 3'-end.

In an embodiment of the ribonucleic acid of the first sub-aspect the length of the double-stranded structure is from about 17 to 23 and more preferably 18 or 19 bases or base pairs.

In another embodiment of the ribonucleic acid of the first sub-aspect the length of said first strand and/or the length of said second strand is independently from each other selected from the group comprising the ranges of from about 15 to about 23 bases, 17 to 21 bases and 18 or 19 bases or base pairs and more preferably 19, 21 or 23 base pairs.

In a preferred embodiment of the ribonucleic acid according to the first sub-aspect the present invention the complementarity between said first strand and the target nucleic acid is perfect.

In an embodiment of the ribonucleic acid according to the first sub-aspect the duplex formed between the first strand and the target nucleic acid comprises at least 15 nucleotides wherein there is one mismatch or two mismatches between said first strand and the target nucleic acid forming said double-stranded structure.

In an embodiment of the ribonucleic acid according to the first sub-aspect both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides.

In a preferred embodiment of the ribonucleic acid according to of the first sub-aspect, each group of modified nucleotides consists of a single nucleotide and/or each flanking group of nucleotides consists of a single nucleotide.

In a further embodiment of the ribonucleic acid according to of the first sub-aspect, on the first strand the nucleotide forming the flanking group of nucleotides is an unmodified nucleotide which is arranged in a 3' direction relative to the nucleotide forming the group of modified nucleotides, and wherein on the second strand the nucleotide forming the group of modified nucleotides is a modified nucleotide which is arranged in 5' direction relative to the nucleotide forming the flanking group of nucleotides.

In a another embodiment of the ribonucleic acid according to the first sub-aspect, the first strand comprises eight to twelve, preferably nine to thirteen, groups of modified nucleotides, and wherein the second strand comprises seven to thirteen, preferably eight to ten, groups of modified nucleotides.

It is within the present invention that what has been specified above is also applicable to the first and second stretch, respectively. This is particular true for those embodiments where the strand consists of the stretch only.

The ribonucleic acid molecule according to such first sub-aspect may be designed is to have a free 5' hydroxyl group, also referred to herein as free 5' OH-group, at the first strand. A free 5' OH-group means that the most terminal nucleotide forming the first strand is present and is thus not modified, particularly not by an end modification. Typically, the terminal 5'-hydroxy group of the second strand, respectively, is also present in an unmodified manner. In a more preferred embodiment, also the 3'-end of the first strand and first stretch, respectively, is unmodified such as to present a free OH-group which is also referred to herein as free 3'OH-group, whereby the design of the 5' terminal nucleotide is the one of any of the afore-described embodiments. Preferably such free OH-group is also present at the 3'-end of the second strand and second stretch, respectively. In other embodiments of the ribonucleic acid molecules as described previously according to the present invention the 3'-end of the first strand and first stretch, respectively, and/or the 3'-end of the second strand and second stretch, respectively, may have an end modification at the 3' end.

As used herein the terms free 5'OH-group and 3'OH-group also indicate that the respective most terminal nucleotide at the 5' end and the 3' end of the polynucleotide, respectively, i.e. either the nucleic acid or the strands and stretches, respectively, forming the double-stranded structure present an OH-group. Such OH-group may stem from either the sugar moiety of the nucleotide, more preferably from the 5'position in case of the 5'OH-group and from the 3'position in case of the 3'OH-group, or from a phosphate group attached to the sugar moiety of the respective terminal nucleotide. The phosphate group may in principle be attached to any OH-group of the sugar moiety of the nucleotide. Preferably, the phosphate group is attached to the 5'OH-group of the sugar moiety in case of the free 5'OH-group and/or to the 3'OH-group of the sugar moiety in case of the free 3'OH-group still providing what is referred to herein as free 5' or 3' OH-group.

As used herein with any embodiment of the first sub-aspect, the term end modification means a chemical entity added to the most 5' or 3' nucleotide of the first and/or second strand. Examples for such end modifications include, but are not limited to, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

As used herein, alkyl or any term comprising "alkyl" means any carbon atom chain comprising 1 to 12, preferably 1 to 6 and more, preferably 1 to 2 C atoms.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications. The polypeptide or protein may confer further characteristics to the inventive nucleic acid molecules. Among others the polypeptide or protein may act as a ligand to another molecule. If said other molecule is a receptor the receptor's function and activity may be activated by the binding ligand. The receptor may show an internalization activity which allows an effective transfection of the ligand bound inventive nucleic acid molecules. An example for the ligand to be coupled to the inventive nucleic acid molecule is VEGF and the corresponding receptor is the VEGF receptor.

Various possible embodiments of the RNAi of the present invention having different kinds of end modification(s) are presented in the following table 1.

TABLE 1

Various embodiments of the interfering ribonucleic acid according to the present invention

| | | $1^{st}$ strand/$1^{st}$ stretch | $2^{nd}$ strand/2nd stretch |
|---|---|---|---|
| 1.) | 5'-end | free OH | free OH |
| | 3'-end | free OH | free OH |
| 2.) | 5'-end | free OH | free OH |
| | 3'-end | end modification | end modification |
| 3.) | 5'-end | free OH | free OH |
| | 3'-end | free OH | end modification |
| 4.) | 5'-end | free OH | free OH |
| | 3'-end | end modification | free OH |
| 5.) | 5'-end | free OH | end modification |
| | 3'-end | free OH | free OH |
| 6.) | 5'-end | free OH | end modification |
| | 3'-end | end modification | free OH |
| 7.) | 5'-end | free OH | end modification |
| | 3'-end | free OH | end modification |
| 8.) | 5'-end | free OH | end modification |
| | 3'-end | end modification | end modification |

The various end modifications as disclosed herein are preferably located at the ribose moiety of a nucleotide of the ribonucleic acid. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasics are nucleotides, either desoxyribonucleotides or ribonucleotides which do not have a nucleobase moiety. This kind of compound is, among others, described in (Sternberger et al., 2002).

Any of the aforementioned end modifications may be used in connection with the various embodiments of RNAi depicted in table 1. In connection therewith it is to be noted that any of the RNAi forms or embodiments disclosed herein with the sense strand being inactivated, preferably by having an end modification more preferably at the 5' end, are particularly advantageous. This arises from the inactivation of the sense strand which corresponds to the second strand of the ribonucleic acids described herein, which might otherwise interfere with an unrelated single-stranded RNA in the cell. Thus the expression and more particularly the translation pattern of the transcriptome of a cell is more specifically influenced. This effect is also referred to as off-target effect. Referring to table 1 those embodiments depicted as embodiments 7 and 8 are particularly advantageous in the above sense as the modification results in an inactivation of the—target unspecific—part of the RNAi (which is the second strand) thus reducing any unspecific interaction of the second strand with single-stranded RNA in a cellular or similar system where the RNAi according to the present invention is going to be used to knock down specific ribonucleic acids and proteins, respectively.

In a further embodiment, the nucleic acid according to the first sub-aspect has an overhang at the 5'-end of the ribonucleic acid. More particularly, such overhang may in principle be present at either or both the first strand and second strand of the ribonucleic acid according to the present invention. The length of said overhang may be as little as one nucleotide and as long as 2 to 8 nucleotides, preferably 2, 4, 6 or 8 nucleotides. It is within the present invention that the 5' overhang may be located on the first strand and/or the second strand of the ribonucleic acid according to the present application. The nucleotide(s) forming the overhang may be (a) desoxyribonucleotide(s), (a) ribonucleotide(s) or a continuation thereof.

The overhang preferably comprises at least one desoxyribonucleotide, whereby said one desoxyribonucleotide is preferably the most 5'-terminal one. It is within the present invention that the 3'-end of the respective counter-strand of the inventive ribonucleic acid does not have an overhang, more preferably not a desoxyribonucleotide overhang. Here again, any of the inventive ribonucleic acids may comprise an end modification scheme as outlined in connection with table 1 and/or and end modification as outlined herein.

Taken the stretch of contiguous nucleotides a pattern, preferably a regular and/or repeating pattern of modification(s) of the nucleotides forming the stretch may be realised in an embodiment such that a single nucleotide or group of nucleotides which are covalently linked to each other via standard phosphorodiester bonds or, at least partially, through phosphorothioate bonds, show such kind of modification. In case such nucleotide or group of nucleotides which is also referred to herein as group of modified nucleotides, is not forming the 5'-end or 3'-end of said stretch a nucleotide or group of nucleotides follows on both sides of the nucleotide which does not have the modification of the preceding nucleotide or group of nucleotides. It is to be noted that this kind of nucleotide or group of nucleotides, however, may have a different modification. This kind of nucleotide or group of nucleotides is also referred to herein as the flanking group of nucleotides. This sequence of modified nucleotide and group of modified nucleotides, respectively, and unmodified or differently modified nucleotide or group of unmodified or differently modified nucleotides may be repeated one or several times. Preferably, the sequence is repeated more than one time. For reason of clarity the pattern is discussed in more detail in the following, generally referring to a group of modified nucleotides or a group of unmodified nucleotides whereby each of said group may actually comprise as little as a single nucleotide. Unmodified nucleotide as used herein means either not having any of the afore-mentioned modifications at the nucleotide forming the respective nucleotide or group of nucleotides, or having a modification which is different from the one of the modified nucleotide and group of nucleotides, respectively.

It is also within the present invention that the modification of the unmodified nucleotide(s) wherein such unmodified nucleotide(s) is/are actually modified in a way different from the modification of the modified nucleotide(s), can be the same or even different for the various nucleotides forming said unmodified nucleotides or for the various flanking groups of nucleotides.

The pattern of modified and unmodified nucleotides may be such that the 5'-terminal nucleotide of the strand or of the stretch starts with a modified group of nucleotides or starts with an unmodified group of nucleotides. However, in an alternative embodiment it is also possible that the 5'-terminal nucleotide is formed by an unmodified group of nucleotides.

This kind of pattern may be realised either on the first stretch or the second stretch of the interfering RNA or on both. It has to be noted that a 5' phosphate on the target-complementary strand of the siRNA duplex is required for siRNA function, suggesting that cells check the authenticity of siRNAs through a free 5' OH (which can be phosphorylated) and allow only such bona fide siRNAs to direct target RNA destruction (Nykanen et al., 2001).

Preferably, the first stretch shows a kind of pattern of modified and unmodified groups of nucleotides, i.e. of group(s) of modified nucleotides and flanking group(s) of nucleotides, whereas the second stretch does not show this kind of pattern or does not show a pattern at all. This may be useful insofar as the first stretch is actually the more important one for the target-specific degradation process underlying the interference phenomenon of RNA so that for specificity reasons the second stretch can be chemically modified so it is not functional in mediating RNA interference.

However, it is also within the present invention that both the first stretch and the second stretch have this kind of pattern. Preferably, the pattern of modification and non-modification is the same for both the first stretch and the second stretch.

In a preferred embodiment the group of nucleotides forming the second stretch and corresponding to the modified group of nucleotides of the first stretch are also modified whereas the unmodified group of nucleotides of or forming the second stretch correspond to the unmodified group of nucleotides of or forming the first stretch. Another alternative is that there is a phase shift of the pattern of modification of the first stretch and first strand, respectively, relative to the pattern of modification of the second stretch and second strand, respectively. Preferably, the shift is such that the modified group of nucleotides of the first strand corresponds to the unmodified group of nucleotides of the second strand and vice versa. It is also within the present invention that the phase shift of the pattern of modification is not complete but overlapping.

In a preferred embodiment the second nucleotide at the terminus of the strand and stretch, respectively, is an unmodified nucleotide or the beginning of group of unmodified nucleotides. Preferably, this unmodified nucleotide or unmodified group of nucleotides is located at the 5'-end of the first and second strand, respectively, and even more preferably of the first strand. In a further preferred embodiment the unmodified nucleotide or unmodified group of nucleotide is located at the 5'-end of the first strand and first stretch, respectively. In a preferred embodiment the pattern consists of alternating single modified and unmodified nucleotides.

In a further preferred embodiment of this aspect of the present invention the interfering ribonucleic acid subject comprises two strands, whereby a 2'-O-methyl modified nucleotide and a non-modified nucleotide, preferably a nucleotide which is not 2'-O-methyl modified, are incorporated on both strands in an alternate manner which means that every second nucleotide is a 2'-O-methyl modified and a non-modified nucleotide, respectively. This means that on the first strand one 2'-O-methyl modified nucleotide is followed by a non-modified nucleotide which in turn is followed by 2'-O-methyl modified nucleotide and so on. The same sequence of 2'-O-methyl modification and non-modification exists on the second strand, whereby there is preferably a phase shift such that the 2'-O-methyl modified nucleotide on the first strand base pairs with a non-modified nucleotide(s) on the second strand and vice versa. This particular arrangement, i.e. base pairing of 2'-O-methyl modified and non-modified nucleotide(s) on both strands is particularly preferred in case of short interfering ribonucleic acids, i.e. short base paired double-stranded ribonucleic acids because it is assumed, although the present inventors do not wish to be bound by that theory, that a certain repulsion exists between two base-pairing 2'-O-methyl modified nucleotides which would destabilise such duplex, preferably short duplexes. About the particular arrangement, it is preferred if the antisense strand starts with a 2'-O-methyl modified nucleotide at the 5' end whereby consequently the second nucleotide is non-modified, the third, fifth, seventh and so on nucleotides are thus again 2'-O-methyl modified whereas the second, fourth, sixth, eighth and the like nucleotides are non-modified nucleotides. Again, not wishing to be bound by any theory, it seems that a particular importance may be ascribed to the second, and optionally fourth, sixth, eighth and/or similar position(s) at the 5' terminal end of the antisense strand which should not comprise any modification, whereas the most 5' terminal nucleotide, i.e. the first 5' terminal nucleotide of the antisense strand may exhibit such modification with any uneven positions such as the first, optionally third, fifth and similar position(s) at the antisense strand may be modified. In further embodiments the modification and non-modification, respectively, of the modified and non-modified nucleotide(s), respectively, may be anyone as described herein. In a more specific embodiment, the double-stranded nucleic acid molecule according to the present invention consists of a first strand of 19, 21 or 23 consecutive nucleotides and a second strand of 19, 21 or 23 consecutive nucleotides, whereby the first strand and the second strand are essentially complementary to each other. Furthermore, in said more specific embodiment the double-stranded structure is blunt-ended at both end. The first strand which is essentially complementary to the target nucleic acid, i.e. an mRNA coding for PKN3, starts at the 5' end with a nucleotide which is methylated at the 2'OH group forming a 2'O-Me group. Every second nucleotide of this first strand has the same modification, i.e. is methylated at the 2' OH group. Thus, the first, third, fifth and so on, i.e. any uneven nucleotide position of the first strand is modified in such a way. The nucleotides at the even positions of the first strand are either non-modified nucleotides or modified nucleotides, whereby the modification is different from the modification of the nucleotides at the uneven nucleotide positions of the first strand. The second strand also preferably comprising 19, 21 or 23 nucleotides, has a modified nucleotide at the second, fourth, sixth and so on, i.e. at any even nucleotide position. Any of the other nucleotides are non-modified nucleotides or modified nucleotides, whereby the modification is different from the modification of the nucleotides at the even nucleotide positions of the first strand. Therefore the second strand starts at the 5' end with a non-modified nucleotide in the above sense. In a more preferred embodiment, the modification of the modified nucleotides of the first and the second strand is the same and the modification of the non-modified nucleotides of the first and the second strand is also the same. In a preferred embodiment the 5' end of the antisense i.e. the first strand has a OH-group which preferably may be phosphorylated in a cell, preferably in a target cell, where the nucleic acid molecule of the present invention is to be active or functional, or has a phosphate group. The 5' end of the sense strand, i.e. the second strand, is preferably also modified, more preferably modified as disclosed herein. Any or both of the 3' ends have, in an embodiment a terminal phosphate.

It is within the present invention that the double-stranded structure is formed by two separate strands, i.e. the first and the second strand. However, it is also with in the present invention that the first strand and the second strand are covalently linked to each other. Such linkage may occur between any of the nucleotides forming the first strand and second strand, respectively. However, it is preferred that the linkage between both strands is made closer to one or both ends of the double-stranded structure. Such linkage can be formed by covalent or non-covalent linkages. Covalent linkage may be formed by linking both strands one or several times and at several positions, respectively, by a compound selected from the group comprising methylene blue and bifunctional groups. Such bifunctional groups are preferably selected from the group comprising bis(2-chloroethyl)amine, N-acetyl-N'-(p-glyoxylbenzoyl)cystamine, 4-thiouracil and psoralene.

In a further embodiment of the ribonucleic acid according to any of the first sub-aspects of the present invention the first strand and the second strand are linked by a loop structure.

In a preferred embodiment of the ribonucleic acid according to the first sub-aspects of the present invention the loop structure is comprised of a non-nucleic acid polymer.

In a preferred embodiment thereof the non-nucleic acid polymer is polyethylene glycol.

In an embodiment of the ribonucleic acid according to any of the first sub-aspects of the present invention the 5'-terminus of the first strand is linked to the 3'-terminus of the second strand.

In a further embodiment of the ribonucleic acid according to any of the aspects of the present invention the 3'-end of the first strand is linked to the 5'-terminus of the second strand.

In an embodiment the loop consists of a nucleic acid. As used herein, LNA as described in Elayadi and Corey (Elayadi et al., 2001); (Orum and Wengel, 2001); and PNA are regarded as nucleic acids and may also be used as loop forming polymers. Basically, the 5'-terminus of the first strand may be linked to the 3'-terminus of the second strand. As an alternative, the 3'-end of the first strand may be linked to the 5'-terminus of the second strand. The nucleotide sequence forming said loop structure is regarded as in general not being critical. However, the length of the nucleotide sequence forming such loop seems to be critical for sterical reasons. Accordingly, a minimum length of four nucleotides seems to be appropriate to form the required loop structure. In principle, the maximum number of nucleotides forming the hinge or the link between both stretches or strands to be hybridised is not limited. However, the longer a polynucleotide is, the more likely secondary and tertiary structures are formed and thus the required orientation of the stretches affected. Preferably, a maximum number of nucleotides forming the hinge is about 12 nucleotides. It is within the disclosure of this application that any of the designs described above may be combined with any of the other designs disclosed herein and known in the art, respectively, i.e. by linking the two strands covalently in a manner that a back folding can occur through a loop structure or similar structure.

The present inventors have surprisingly found that if the loop is placed 3' of the antisense strand, i.e. the first strand of the ribonucleic acid(s) according to the present invention, the activities of this kind of RNAi are higher compared to the placement of the loop 5' of the antisense strand. Accordingly, the particular arrangement of the loop relative to the antisense strand and sense strand, i.e. the first strand and the second strand, respectively, is crucial and is thus in contrast to the understanding as expressed in the prior art where the orientation is said to be of no relevance. However, this seems not true given the experimental results presented herein. The understanding as expressed in the prior art is based on the assumption that any RNAi is subject to a processing during which non-loop linked RNAi is generated. However, if this was the case, the clearly observed increased activity of those structures having the loop placed 3' of the antisense could not be explained. Insofar a preferred arrangement in 5'→3' direction of this kind of small interfering RNAi is second strand—loop—first strand. The respective constructs may be incorporated into suitable vector systems. Preferably the vector comprises a promoter for the expression of RNAi. Preferably the respective promoter is pol III and more preferably the promoters are the U6, H1, 7SK promoter as described in Good et al. (Good et al., 1997).

The second sub-aspect of the first aspect of the present invention is related to a nucleic acid according to the present invention, whereby first stretch and/or the second stretch comprise at the 3' end a dinucleotide, whereby such dinucleotide is preferably TT. In a preferred embodiment, the length of the first stretch and/or of the second stretch consists of either 19 or 21 or 23 nucleotides and more preferably the double-stranded structure comprises 18 to 22 and more preferably 19 to 21 base pairs. The design of the nucleic acid in accordance with this sub-aspect is described in more detail in e.g., in international patent application WO 01/75164.

The third sub-aspect of the first aspect of the present invention is related to a nucleic acid according to the present invention, whereby the first and/or the second stretch comprise an overhang of 1 to 5 nucleotides at the 3' end. The design of the nucleic acid in accordance with this sub-aspect is described in more detail in international patent application WO 02/44321. More preferably such overhang is a ribonucleic acid. In a preferred embodiment each of the strands and more preferably each of the stretches as defined herein has a length from 19 to 25 nucleotides, whereby more preferably the strand consists of the stretch. In a preferred embodiment, the double-stranded structure of the nucleic acid according to the present invention comprises 17 to 25 base pairs, preferably 19 to 23 base pairs more preferably 19, 21 or 23 base pairs.

The fourth sub-aspect of the first aspect of the present invention is related to a nucleic acid according to the present invention, whereby the first and/or the second stretch comprise an overhang of 1 to 5 nucleotides at the 3' end. The design of the nucleic acid in accordance with this sub-aspect is described in WO 02/44321.

In a fifth sub-aspect of the first aspect of the present invention the nucleic acid according to the present invention is a double-stranded nucleic acid which is a chemically synthesized double-stranded short interfering nucleic acid (siNA) molecule which directs cleavage of a CD31 mRNA, preferably via RNA interference, wherein each strand of said siNA molecule is 18 to 27 or 19 to 29 nucleotides in length and said siNa molecule comprises at least one chemically modified nucleotide non-nucleotide. The design of the nucleic acid in accordance with this sub-aspect is described in more detail in international patent application WO03/070910 and UK patent 2 397 062.

In one embodiment thereof the siNA molecule comprises no ribonucleotides. In another embodiment, the siNA molecule comprises one or more nucleotides. In another embodiment chemically modified nucleotide comprises a 2'-deoxy nucleotide. In another embodiment chemically modified nucleotide comprises a 2'-deoxy-2'-fluoro nucleotide. In another embodiment chemically modified nucleotide comprises a 2'-O-methyl nucleotide. In another embodiment chemically modified nucleotide comprises a phosphorothioate internucleotide linkage. In a further embodiment the non-nucleotide comprises an abasic moiety, whereby preferably the abasic moiety comprises an inverted deoxyabasic moiety. In another embodiment non-nucleotide comprises a glyceryl moiety.

In a further embodiment, the first strand and the second strand are connected via a linker molecule. Preferably, the linker molecule is polynucleotide linker. Alternatively, the linker molecule is a non-nucleotide linker.

In a further embodiment of the nucleic acid according to the fifth sub-aspect, the pyrimidine nucleotides in the second strand are 2'-O-methylpyrimidine nucleotides.

In a further embodiment of the nucleic acid according to the fifth sub-aspect, the purine nucleotides in the second strand are 2'-deoxy purine nucleotides.

In a further embodiment of the nucleic acid according to the fifth sub-aspect, the pyrimidine nucleotides in the second strand are 2'-deoxy-2'-fluoro pyrimidine nucleotides.

In a further embodiment of the nucleic acid according to the fifth sub-aspect, the second strand includes a terminal cap moiety at the 5' end, the 3' end or both the 5' end and the 3' end.

In a further embodiment of the nucleic acid according to the fifth sub-aspect, the pyrimidine nucleotides in the first strand are 2'-deoxy-2' fluoro pyrimidine nucleotides.

In a further embodiment of the nucleic acid according to the fifth sub-aspect, the purine nucleotides in the first strand are 2'-O-methyl purine nucleotides.

In a further embodiment of the nucleic acid according to the fifth sub-aspect, the purine nucleotides in the first strand are 2'-deoxy purine nucleotides.

In a further embodiment of the nucleic acid according to the fifth sub-aspect, the first strand comprises a glyceryl modification at the 3' end of the first strand.

In a further embodiment of the nucleic acid according to the fifth sub-aspect, the first strand comprises a glyceryl modification are the 3' end of the first strand.

In a further embodiment of the nucleic acid according to the fifth sub-aspect, about 19 to 23 nucleotides of both the first and the second strand are base-paired and wherein preferably at least two 3' terminal nucleotides of each strand of the siNA molecule are not base-paired to the nucleotides of the other strand. Preferably, each of the two 3' terminal nucleotides of each strand of the siNA molecule are 2'-deoxy-pyrimidines. More preferably, the 2'deoxy-pyrimidine is 2' deoxy-thymidine.

In a further aspect of the nucleic acid according to the fifth sub-aspect, the 5' end of the first strand comprises a phosphate group.

In one embodiment particularly of the fifth sub-aspect of the nucleic acid according to the present invention, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

In a non-limiting example, the introduction of chemically-modified nucleotides into nucleic acid molecules particularly of the fifth sub-aspect of the nucleic acid according to the present invention provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

Preferably in connection with the fifth sub-aspect of the nucleic acid according to the present invention, the antisense strand, i.e. the first strand, of a siNA molecule of the invention can comprise a phosphorothioate internucleotide linkage at the 3'-end of said antisens region. The antisense strand can comprise about one to about five phosphorothioate internucleotide linkages at the 5'-end of said antisense region. The 3'-terminal nucleotide overhangs of a siNA molecule of the invention can comprise ribonucleotides or deoxyribonucleotides that are chemically-modified at a nucleic acid sugar, base or backbone. The 3'-terminal nucleotide overhangs can comprise one or more universal base ribonucleotides. The 3'-terminal nucleotide overhangs can comprise one or more acyclic nucleotides.

It will be acknowledged by the ones skilled in the art that particularly the embodiment of the present invention which comprises a loop made of nucleotides is suitable to be used and expressed by a vector. Preferably, the vector is an expression vector. Such expression vector is particular useful in any gene therapeutic approach. Accordingly, such vector can be used for the manufacture of a medicament which is preferable to be used for the treatment of the diseases disclosed herein. It will, however, also be acknowledged by the ones skilled in the art that any embodiment of the nucleic acid according to the present invention which comprises any non-naturally occurring modification cannot immediately be used for expression in a vector and an expression system for such vector such as a cell, tissue, organ and organism. However, it is within the present invention that the modification may be added to or introduced into the vector derived or vector expressed nucleic acid according to the present invention, typically after the expression of the nucleic acid by the vector. A particularly preferred vector is a plasmid vector or a viral vector. The technical teaching on how to use siRNA molecules and RNAi molecules in an expression vector is, e.g., described in international patent application WO 01/70949. It will be acknowledged by the ones skilled in the art that such vector is preferably useful in any method either therapeutic or diagnostic where a sustained presence of the nucleic acid according to the present invention is desired and useful, respectively, whereas the non-vector nucleic acid according to the present invention and in particular the chemically modified or chemically synthesized nucleic acid according to the present invention is particularly useful where the transient presence of the molecule is desired or useful.

Methods for the synthesis of the nucleic acid molecule described herein are known to the ones skilled in the art. Such methods are, among others, described in (Caruthers et al., 1992), Thompson et al., International PCT Publication No. WO 99/54459, (Wincott et al., 1995), (Wincott and Usman, 1997), Brennan et al., 1998, *Biotechnol Bioeng.*, 61, 33-45, and Brennan, U.S. Pat. No. 6,001,311. All of these references are incorporated herein by reference.

In a further aspect, the present invention is related to a liposomal formulation comprising and more specifically containing one or several of the nucleic acid molecules according to the present invention. Preferably such liposomal formulation consists of lipid(s) defining an inner volume. Such inner volume preferably contains the nucleic acid molecules(s) of the present invention. More preferably such formulation comprises liposomes, whereby in a preferred embodiment the liposome comprises or contains one or several cationic lipids. In a most preferred embodiment the liposomal formulation contains one or several of the nucleic acid molecule(s) of the present invention such that the nucleic acid molecule(s) is/are not detectable or present at or on the outer surface of the liposome. As preferably used herein, the outer surface of the liposome is the surface of the liposome which is in contact with the environment surrounding the liposome, particularly in contrast to the surface of the liposome which is in contact with the fluid encompassed by the liposome. In a particularly preferred embodiment, the nucleic acid molecule(s) according to the present invention is/are packed or encapsulated by or in said liposome and liposomal formulation, respectively.

In a further aspect the present invention is related to lipoplexes comprising the nucleic acid according to the present invention, whereby such lipoplexes consists of one or several nucleic acid molecules and one or several liposomes. In a preferred embodiment of a lipoplex consists of one liposome and several nucleic acid molecules.

The lipoplex can be characterised as follows. The lipoplex according to the present invention has a zeta-potential of about 40 to 55 mV, preferably about 45 to 50 mV. The size of the lipoplex according to the present invention is about 80 to 200 nm, preferably of about 100 to 140 nm, and more preferably of about 110 nm to 130 nm, as determined by dynamic light scattering (QELS) such as, e.g., by using an N5 submicron particle size analyzer from Beckman Coulter according to the manufacturer's recommendation.

The liposome as forming part of the lipoplex according to the present invention is preferably a positively charged liposome consisting of a) about 50 mol % β-arginyl-2,3-diaminopropionic acid-N-palmityl-N-oleyl-amide trihydrochloride, preferably (β-(L-arginyl)-2,3-L-diaminopropionic acid-N-palmityl-N-oleyl-amide tri-hydrochloride), b) about 48 to 49 mol % 1,2-diphytanoyl-sn-glycero-3-phosphoethanolamine (DPhyPE), and c) about 1 to 2 mol % 1,2-distearoyl-sn-glycero-3-phosphoethanolamine-polyethylen-glycole, preferably N-(Carbonyl-methoxypolyethyleneglycol-2000)-1,2-distearoyl-sn-glycero-3-phosphoethanolamine sodium salt.

The lipoplex and lipid composition forming the liposomes are preferably contained in a carrier. However, the lipoplex can also be present in a lyophilised form. The lipid composition contained in a carrier usually forms a dispersion. More preferably, the carrier is an aqueous medium or aqueous solution as also further characterised herein. The lipid composition typically forms a liposome in the carrier, whereby such liposome preferably also contains the carrier inside.

The lipid composition contained in the carrier and the carrier, respectively, preferably has an osmolarity of about 50 to 600 mosmole/kg, preferably about 250-350 mosmole/kg, and more preferably about 280 to 320 mosmole/kg.

The liposomes preferably formed by the first lipid component and optionally also by the first helper lipid, preferably in combination with the first lipid component, preferably exhibit a particle size of about 20 to 200 nm, preferably about 30 to 100 nm, and more preferably about 40 to 80 nm.

Furthermore, it will be acknowledged that the size of the particle follows a certain statistical distribution.

A further optional feature of the lipid composition in accordance with the present invention is that the pH of the carrier is preferably from about 4.0 to 6.0. However, also other pH ranges such as from 4.5 to 8.0, preferably from about 5.5 to 7.5 and more preferably about 6.0 to 7.0 are within the present invention.

For realizing these particular features various measures may be taken. For adjusting the osmolarity, for example, a sugar or a combination of sugars is particularly useful. Insofar, the lipid composition of the present invention may comprise one or several of the following sugars: sucrose, trehalose, glucose, galactose, mannose, maltose, lactulose, inulin and raffinose, whereby sucrose, trehalose, inulin and raffinose are particularly preferred. In a particularly preferred embodiment the osmolarity mostly adjusted by the addition of sugar is about 300 mosmole/kg which corresponds to a sucrose solution of 270 mM or a glucose solution of 280 mM. Preferably the carrier is isotonic to the body fluid into which such lipid composition is to be administered. As used herein the term that the osmolarity is mostly adjusted by the addition of sugar means that at least about 80%, preferably at least about 90%, of the osmolarity is provided by said sugar or a combination of said sugars.

If the pH of the lipid composition of the present invention is adjusted, this is done by using buffer substances which, as such, are basically known to the one skilled in the art. Preferably, basic substances are used which are suitable to compensate for the basic characteristics of the cationic lipids and more specifically of the ammonium group of the cationic head group. When adding basic substances such as basic amino acids and weak bases, respectively, the above osmolarity is to be taken into consideration. The particle size of such lipid composition and the liposomes formed by such lipid composition is preferably determined by dynamic light scattering such as by using an N5 submicron particle size analyzer from Beckman Coulter according to the manufacturer's recommendation.

If the lipid composition contains one or several nucleic acid(s), such lipid composition usually forms a lipoplex complex, i.e. a complex consisting of a liposome and a nucleic acid. The more preferred concentration of the overall lipid content in the lipoplex in preferably isotonic 270 mM sucrose or 280 mM glucose is from about 0.01 to 100 mg/ml, preferably 0.01 to 40 mg/ml and more preferably 0.01 to 25 mg/ml. It is to be acknowledged that this concentration can be increased so as to prepare a reasonable stock, typically by a factor of 2 to 3. It is also within the present invention that based on this, a dilution is prepared, whereby such dilution is typically made such that the osmolarity is within the range specified above. More preferably, the dilution is prepared in a carrier which is identical or in terms of function and more specifically osmolarity similar to the carrier used in connection with the lipid composition or in which the lipid composition is contained. In the embodiment of the lipid composition of the present invention whereby the lipid composition also comprises a nucleic acid, preferably a functional nucleic acid such as, but not limited to, a siRNA, the concentration of the siRNA in the lipid composition is about 0.2 to 0.4 mg/ml, preferably 0.28 mg/ml, and the total lipid concentration is about 1.5 to 2.7 mg/ml, preferably 2.17 mg/ml. It is to be acknowledged that this mass ratio between the nucleic acid fraction and the lipid fraction is particularly preferred, also with regard to the charge ratio thus realized. In connection with any further concentration or dilution of the lipid composition of the present invention, it is preferred that the mass ratio and the charge ratio, respectively, realized in this particular embodiment is preferably maintained despite such concentration or dilution.

Such concentration as used in, for example, a pharmaceutical composition, can be either obtained by dispersing the lipid in a suitable amount of medium, preferably a physiologically acceptable buffer or any carrier described herein, or can be concentrated by appropriate means. Such appropriate means are, for example, ultra filtration methods including cross-flow ultra-filtration. The filter membrane may exhibit a pore width of 1,000 to 300,000 Da molecular weight cut-off (MWCO) or 5 nm to 1 μm. Particularly preferred is a pore width of about 10,000 to 100,000 Da MWCO. It will also be acknowledged by the one skilled in the art that the lipid composition more specifically the lipoplexes in accordance with the present invention may be present in a lyophilized form. Such lyophilized form is typically suitable to increase the shelve life of a lipoplex. The sugar added, among others, to provide for the appropriate osmolarity, is used in connection therewith as a cryoprotectant. In connection therewith it is to be acknowledged that the aforementioned characteristics of osmolarity, pH as well as lipoplex concentration refers to the dissolved, suspended or dispersed form of the lipid composition in a carrier, whereby such carrier is in principle any carrier described herein and typically an aqueous carrier such as water or a physiologically acceptable buffer, preferably an isotonic buffer or isotonic solution.

Apart from these particular formulation, the nucleic acid molecules according to the present invention may also be formulated in pharmaceutical compositions as is known in the art.

Accordingly, the nucleic acid molecules according to the present invention can preferably be adapted for use as medicaments and diagnostics, alone or in combination with other therapies. For example, a nucleic acid molecule according to the present invention can comprise a delivery vehicle, including liposomes, for administration to a subject, carriers and diluents and their salts, and/or can be present in pharmaceutically acceptable formulations. Methods for the delivery of nucleic acid molecules are described in (Agrawal and Akhtar, 1995; Akhtar and Juliano, 1992), (Maurer et al., 1999); (Holland and Huang, 1995); and Lee et al., 2000, ACS Symp. Ser., 752, 184-192 all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can also be administered to cells by a variety of methods known to those of skill in the art, including, but not limited to, encapsulation in liposomes, by iontophoresis, or by incorporation into other vehicles, such as hydrogels, cyclodextrins (see for example Gonzalez et al., 1999), biodegradable nanocapsules, and bioadhesive microspheres, or by proteinaceous vectors (O'Hare and Normand, International PCT Publication No. WO 00/53722). Alternatively, the nucleic acid/vesicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999 and Barry et al., international PCT Publication No. WO 99/31262. The molecules of the instant invention can be used as pharmaceutical agents. Preferably, pharmaceutical agents prevent, modulate the occurrence of, or treat (alleviate a symptom to some extent, preferably all of the symptoms) a disease state in a subject.

Thus, the present invention also provides a pharmaceutical composition comprising one or more nucleic acid(s) according to the present invention in an acceptable carrier, such as a stabilizer, buffer, and the like. The polynucleotides or nucleic acid (molecules) of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

There are further provided pharmaceutically acceptable formulations of the nucleic acid molecules according to the present invention. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is preferably meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the nucleic acids according to the present invention can potentially localize the drug, for example, in certain tissue types, such as neoplastic tissue(s). A liposome formulation that can facilitate the association of drug with the surface of cells, such as lymphocytes and macrophages is also useful. This approach can provide enhanced delivery of the drug to target cells by taking advantage of the specificity of macrophage and lymphocyte immune recognition of abnormal cells, such as cells forming the neoplastic tissue.

By "pharmaceutically acceptable formulation" is preferably meant, a composition or formulation that allows for the effective distribution of the nucleic acid molecules according to the present invention in the physical location most suitable for their desired activity. Non-limiting examples f or agents suitable for formulation with the nucleic acid molecules according to the present invention include: P-glycoprotein inhibitors (such as Pluronic P85), which can enhance entry of drugs into the CNS (Jolliet-Riant and Tillement, 1999); biodegradable polymers, such as poly (DL-lactide-coglycolide) microspheres for sustained release delivery after intracerebral implantation (Emerich et al., 1999) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies for the nucleic acid molecules of the instant invention include material described in (Boado et al., 1998); Tyler et al., 1999, FEBS Lett., 421, 280-284; pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

In accordance with the present invention there is also provided the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24780; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

There are moreover provided compositions prepared for storage of administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agent can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or threat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules according to the present invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules according to the present invention can be present in association with one or more non-toxic pharmaceutically acceptable carriers and/or diluents and/or adjuvants, and if desired other active ingredients. The pharmaceutical compositions containing nucleic acid molecules according to the present invention can be in a form suitable for oral use, for example, as tablets, troches, lozenges, aqueous or oily suspensions, dispersible powders or granules, emulsion, hard or soft capsules, or syrups or elixirs.

Compositions and in particular pharmaceutical compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxyoctanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and coloring agents, can also be present.

Pharmaceutical compositions of the invention can also be in the form of oil-in-water emulsions. The oily phase can be a vegetable oil or a mineral oil or mixture of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and coloring agents. The pharmaceutical compositions can be in the from of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels for the medicament and pharmaceutical composition, respectively, can be determined by those skilled in the art by routine experimentation.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration of the medicament according to the present invention to non-human animals such as dogs, cats, horses, cattle, pig, goat, sheep, mouse, rat, hamster and guinea pig, the composition can preferably also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In an embodiment, the nucleic acid molecules, in their various embodiments, forms and formulations, respectively, can be used with other therapies such as chemotherapy, cryotherapy, hyperthermia, antibody therapy, radiation therapy and anti-angiogenesis therapy. A particularly preferred therapy is anti-angiogenesis therapy. In connection with anti-angiogenesis therapy particularly preferred targets are the VEGF receptor and the PDGF receptor. Anti-angiogenesis therapy is typically effected by using inhibitors to angiogenesis related targets such as the VEGF receptor and the PDGF receptor. Apart from small molecules also other kinds of compounds can be generated or provided or used which act as inhibitors to such targets. The following classes of compounds may accordingly be used: siRNA as, among others, described in WO 00/44895 or WO 01/75164; antisense molecules as, among others, described in U.S. Pat. No. 5,849,902, U.S. Pat. No. 5,989,912 or known as gene blocks; aptamers as, among others, described in EP 0 533 838 B1; spiegelmers as, among others, described in WO 98/08856; high affinity binding peptides which can be identified from random sequence peptide libraries comprising $10^2$ to $10^{18}$ peptides differing in their amino acid sequence in a manner similar to aptamers and are, therefore, sometimes also referred to as peptide aptamers; anticalines as, among others, described in DE 197 42 706; and antibodies which are, among others described in "Antibodies: A Laboratory Manual", Cold Spring Harbor Laboratory (eds. Harlow, E. and Lane D.).

In one embodiment, there are provided compositions suitable for administering the nucleic acid molecules according to the present invention to specific cell types, whereby such compositions typically incorporate one or several of the following principles and molecules, respectively. For example, the asialoglycoprotein receptor (ASGPr) (Wu and Wu, 1987, *J. Biol. Chem.* 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligonsaccharide chain, for example, tria-tennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987. *Glycoconjugate J*, 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 60/362,016, filed Mar. 6, 2002.

The nucleic acid molecules, in their various embodiments, according to the present invention, the vector, cell, medicament, composition and in particular pharmaceutical composition containing the same, tissue and animal, respectively, according to the present invention containing such a nucleic acid molecule can be used in both for a therapeutic as well as in the diagnostic and research field.

Due to the distribution of PKN3 in various tissues and vascular endothelium involved in the following diseases, the nucleic acid molecule according to the present invention may be used for the treatment and/or prevention of said diseases, preferably diseases which are characterized by involving, preferably in the pathological mechanism or the diseased tissue, cells, preferably tumor cells which are PTEN-negative.

Accordingly, the nucleic acid molecules as disclosed herein and the medicaments and pharmaceutical compositions containing the same may be used for both pro- and anti-angiogenic therapies including diseases characterized or caused by insufficient, abnormal or excessive angiogenesis. Such diseases comprise infectious diseases, autoimmune disorders, vascular malformation, atherosclerosis, transplant arteriopathy, obesity, psoriasis, warts, allergic dermatitis, persistent hyperplastic vitreous syndrome, diabetic retinopathy, retinopathy of prematurity, age-related macular disease, choroidal neovascularization, primary pulmonary hypertension, asthma, nasal polyps, inflammatory bowel and periodontal disease, ascites, peritoneal adhesions, endometriosis, uterine bleeding, ovarian cysts, ovarian hyperstimulation, arthritis, synovitis, osteomyelitis, osteophyte formation and stroke, ulcers, atherosclerosis and rheumatoid arthritis.

Further diseases are those involving or characterized by a neoplastic tissue. As preferably used herein, the term neoplastic tissues refers to tissues which are generated by an organism, tissue or cells of such organism which are not intended to be generated and which are deemed as pathologic, i.e. not present in a subject not suffering from such a respective disease. Also, as preferably used herein, a neoplastic disease is any disease which, either directly or indirectly, arises from the presence of a neoplastic tissue, whereby preferably such neoplastic tissue rises from the dysregulated or uncontrolled, preferably autonomous growth of a/the tissue. The term neoplastic diseases preferably also comprises benign as well as malignant neoplastic diseases. More preferably, the neoplastic diseases are selected from the group comprising any cancer of, e.g., bone, breast, prostate, digestive system, colorectal, liver, lung, kidney, urogenital, pancreatic, pituitary, testicular, orbital, head and neck, central nervous system, respiratory.

Further specific diseases which, in principle, can be treated using the pharmaceutical composition and the medicament in accordance with the present invention, comprising such lipid composition and lipoplex, respectively, may be taken from the following list: Acute Lymphoblastic Leukemia, (Adult), Acute Lymphoblastic Leukemia, (Childhood), Acute Myeloid Leukemia, (Adult) Acute Myeloid Leukemia, (Childhood), Adrenocortical Carcinoma, Adrenocortical Carcinoma, (Childhood), AIDS-Related Cancers, AIDS-Related Lymphoma, Anal Cancer, Astrocytoma, (Childhood), Cerebellar Astrocytoma, (Childhood) Cerebral, Bile Duct Cancer, Extrahepatic, Bladder Cancer, Bladder Cancer, (Childhood), Bone Cancer, Osteosarcoma/Malignant Fibrous Histiocytoma, Brain Stem Glioma, (Childhood), Brain Tumor, (Adult), Brain Tumor, Brain Stem Glioma, (Childhood), Brain Tumor, Cerebellar Astrocytoma, (Childhood), Brain Tumor, Cerebral Astrocytoma/Malignant Glioma, (Childhood), Brain Tumor, Ependymoma, (Childhood), Brain Tumor, Medulloblastoma, (Childhood), Brain Tumor, Supratentorial Primitive Neuroectodermal Tumors, (Childhood), Brain Tumor, Visual Pathway and Hypothalamic Glioma, (Childhood), Brain Tumor, (Childhood), Breast Cancer, Breast Cancer, (Childhood), Breast Cancer, Male, Bronchial Adenomas/Carcinoids, (Childhood), Burkitt's Lymphoma, Carcinoid Tumor, (Childhood), Carcinoid Tumor, Gastrointestinal, Carcinoma of Unknown Primary, Central Nervous System Lymphoma, Primary, Cerebellar Astrocytoma, (Childhood), Cerebral Astrocytoma/Malignant Glioma, (Childhood), Cervical Cancer, Chronic Lymphocytic Leukemia, Chronic Myelogenous Leukemia, Chronic Myeloproliferative Disorders, Colon Cancer, Colorectal Cancer, (Childhood), Cutaneous T-Cell Lymphoma, Endometrial Cancer, Ependymoma, (Childhood), Esophageal Cancer, Esophageal Cancer, (Childhood), Ewing's Family of Tumors, Extracranial Germ Cell Tumor, (Childhood), Extragonadal Germ Cell Tumor, Extrahepatic Bile Duct Cancer, Eye Cancer, Intraocular Melanoma, Eye Cancer, Retinoblastoma, Gallbladder Cancer, Gastric (Stomach) Cancer, Gastric (Stomach) Cancer, (Childhood), Gastrointestinal Carcinoid Tumor, Germ Cell Tumor, Extracranial, (Childhood), Germ Cell Tumor, Extragonadal, Germ Cell Tumor, Ovarian, Gestational Trophoblastic Tumor, Glioma, (Adult), Glioma, (Childhood) Brain Stem, Glioma, (Childhood) Cerebral Astrocytoma, Glioma, (Childhood) Visual Pathway and Hypothalamic, Hairy Cell Leukemia, Head and Neck Cancer, Hepatocellular (Liver) Cancer, (Adult) (Primary), Hepatocellular (Liver) Cancer, (Childhood) (Primary), Hodgkin's Lymphoma, (Adult), Hodgkin's Lymphoma, (Childhood), Hypopharyngeal Cancer, Hypothalamic and Visual Pathway Glioma, (Childhood), Intraocular Melanoma, Islet Cell Carcinoma (Endocrine Pancreas), Kaposi's Sarcoma, Kidney (Renal Cell) Cancer, Kidney Cancer, (Childhood), Laryngeal Cancer, Laryngeal Cancer, (Childhood), Leukemia, Acute Lymphoblastic, (Adult), Leukemia, Acute Lymphoblastic, (Childhood), Leukemia, Acute Myeloid, (Adult), Leukemia, Acute Myeloid, (Childhood), Leukemia, Chronic Lymphocytic Leukemia, Chronic Myelogenous, Leukemia, Hairy Cell, Lip and Oral Cavity Cancer, Liver Cancer, (Adult) (Primary), Liver Cancer, (Childhood) (Primary), Lung Cancer, Non-Small Cell, Lung Cancer, Small Cell, Lymphoma, AIDS-Related, Lymphoma, Burkitt's, Lymphoma, Cutaneous T-Cell, Lymphoma, Hodgkin's, (Adult), Lymphoma, Hodgkin's, (Childhood), Lymphoma, Non-Hodgkin's, (Adult), Lymphoma, Non-Hodgkin's, (Childhood), Lymphoma, Primary Central Nervous System, Macroglobulinemia, Waldenström's Malignant Fibrous Histiocytoma of Bone/Osteosarcoma, Medulloblastoma, (Childhood), Melanoma, Melanoma, Intraocular (Eye), Merkel Cell Carcinoma, Mesothelioma, (Adult) Malignant, Mesothelioma, (Childhood), Metastatic Squamous Neck Cancer with Occult Primary, Multiple Endocrine Neoplasia Syndrome, (Childhood), Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, (Adult) Acute, Myeloid Leukemia, (Childhood) Acute, Myeloma, Multiple, Myeloproliferative Disorders, Chronic, Nasal Cavity and Paranasal Sinus Cancer, Nasopharyngeal Cancer, Nasopharyngeal Cancer, (Childhood), Neuroblastoma, Non-Hodgkin's Lymphoma, (Adult), Non-Hodgkin's Lymphoma, (Childhood), Non-Small Cell Lung Cancer, Oral Cancer, (Childhood), Oral Cavity Cancer, Lip and Oropharyngeal Cancer, Osteosarcoma/Malignant Fibrous Histiocytoma of Bone, Ovarian Cancer, (Childhood), Ovarian Epithelial Cancer, Ovarian Germ Cell Tumor, Ovarian Low Malignant Potential Tumor, Pancreatic Cancer, Pancreatic Cancer, (Childhood), Pancreatic Cancer, Islet Cell, Paranasal Sinus and Nasal Cavity Cancer, Parathyroid Cancer, Penile Cancer, Pheochromocytoma, Pineoblastoma and Supratentorial Primitive Neuroectodermal Tumors, (Childhood), Pituitary Tumor, Plasma Cell Neoplasm/Multiple Myeloma, Pleuropulmonary Blastoma, Pregnancy and Breast Cancer, Pregnancy and Hodgkin's Lymphoma, Pregnancy and Non-Hodgkin's Lymphoma, Primary Central Nervous System Lymphoma, Prostate Cancer, Rectal Cancer, Renal Cell (Kidney) Cancer, Renal Cell (Kidney) Cancer, (Childhood), Renal Pelvis and Ureter, Transitional Cell Cancer, Retinoblastoma, Rhabdomyosarcoma, (Childhood), Salivary Gland Cancer, Salivary Gland Cancer, (Childhood), Sarcoma, Ewing's, Sarcoma, Kaposi's, Sarcoma, Soft Tissue, (Adult), Sarcoma, Soft Tissue, (Childhood), Sarcoma, Uterine, Sezary Syndrome, Skin Cancer (non-Melanoma), Skin Cancer, (Childhood), Skin Cancer (Melanoma), Skin Carcinoma, Merkel Cell, Small Cell Lung Cancer, Small Intestine Cancer, Soft Tissue Sarcoma, (Adult), Soft Tissue Sarcoma, (Childhood), Squamous Cell Carcinoma, Squamous Neck Cancer with Occult Primary, Metastatic Stomach (Gastric) Cancer, Stomach (Gastric) Cancer, (Childhood), Supratentorial Primitive Neuroectodermal Tumors, (Childhood), T-Cell Lymphoma, Cutaneous, Testicular Cancer, Thymoma, (Childhood), Thymoma and Thymic Carcinoma, Thyroid Cancer Thyroid Cancer, (Childhood), Transitional Cell Cancer of the Renal Pelvis and Ureter, Trophoblastic Tumor, Gestational, Ureter and Renal Pelvis, Transitional Cell Cancer, Urethral Cancer, Uterine Cancer, Endometrial, Uterine Sarcoma, Vaginal Cancer, Visual Pathway and Hypothalamic Glioma, (Childhood), Vulvar Cancer, Waldenström's Macroglobulinemia, Wilms' Tumor.

Apart from PKN3 being involved in angiogenesis, more specifically in the inhibition of motility of endothelial cells contributing to tumor angiogenesis and migration of tumors, more specifically in case of prostate cancer (c.f. Leenders et al., 2004, EMBO J. 23 (16):3303-3313), PKN3 is part of the PI3-kinase pathway.

The PI 3-kinase pathway is characterized by a PI 3-kinase activity upon growth factor induction and a parallel signalling pathway. Growth factor stimulation of cells leads to activation of their cognate receptors at the cell membrane which in turn associate with and activate intracellular signalling molecules such as PI 3-kinase. Activation of PI 3-kinase (consisting of a regulatory p85 and a catalytic p110 subunit) results in activation of Akt by phosphorylation, thereby supporting cellular responses such as proliferation, survival or migration further downstream. PTEN is thus a tumor suppressor which is involved in the phosphatidylinositol (PI) 3-kinase pathway and which has been extensively studied in the past for its role in regulating cell growth and transformation (for reviews see, Stein, R. C. and Waterfield, M. D. (2000). PI3-kinase inhibition: a target for drug development? Mol Med Today 6, 347-357; Vazquez, F. and Sellers, W. R. (2000). The PTEN tumor suppressor protein: an antagonist of phosphoinositide 3-kinase signaling. Biochim Biophys Acta 1470, M21-35; Roymans, D. and Slegers, H. (2001). Phosphatidylinositol 3-kinases in tumor progression. Eur J Biochem 268, 487-498). The tumor suppressor PTEN functions as a negative regulator of PI 3-kinase by reversing the PI 3-kinase-catalyzed reaction and thereby ensures that activation of the pathway occurs in a transient and controlled manner. Chronic hyperactivation of PI 3-kinase signalling is caused by functional inactivation of PTEN. PI 3-kinase activity can be blocked by addition of the small molecule inhibitor LY294002. The activity and downstream responses of the signalling kinase MEK which acts in a parallel pathway, can, for example, be inhibited by the small molecule inhibitor PD98059.

A chronic activation of the PI 3-kinase pathway through loss of PTEN function is a major contributor to tumorigenesis and metastasis indicating that this tumor suppressor represents an important checkpoint for a controlled cell proliferation. PTEN knock out cells show similar characteristics as cells in which the PI 3-kinase pathway has been chronically induced via activated forms of PI 3-kinase (Di Cristofano, A., Pesce, B., Cordon-Cardo, C. and Pandolfi, P. P. (1998). PTEN is essential for embryonic development and tumour suppression. Nat Genet 19, 348-355. Klippel, A., Escobedo, M. A., Wachowicz, M. S., Apell, G., Brown, T. W., Giedlin, M. A., Kavanaugh, W. M. and Williams, L. T. (1998). Activation of phosphatidylinositol 3-kinase is sufficient for cell cycle entry and promotes cellular changes characteristic of oncogenic transformation. Mol Cell Biol 18, 5699-5711. Kobayashi, M., Nagata, S., Iwasaki, T., Yanagihara, K., Saitoh, I., Karouji, Y., Ihara, S, and Fukui, Y. (1999). Dedifferentiation of adenocarcinomas by activation of phosphatidylinositol 3-kinase. Proc Natl Acad Sci USA 96, 4874-4879).

PTEN is involved in several pathways which are also referred to as PTEN related pathways such as the PI3K/PTEN pathway, the Akt pathway, the EGF-related autocrine loop and the mTOR pathway. A PI3-kinase pathway is actually any pathway which involves PI 3-kinase, either directly or indirectly. PI 3-kinase may act either as an inhibitor or as an activator in such pathway, or it may as such be regulated by other elements of the pathway.

There is ample of prior art describing diseases and conditions involving the PI 3-kinase pathway. Any of these conditions and diseases may thus be addressed by the inventive methods and the drugs and diagnostic agents the design, screening or manufacture thereof is taught herein. For reasons of illustration but not limitation it is referred to the following: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., Journal of the National Cancer Institute, Vol. 92, no. 11, Jun. 7, 2000, page 861-863), Bannayan-Zonana syndrome, LDD (Lhermitte-Duklos' syndrome) (Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra).

In view of this, PKN3 is a valuable downstream drug target of the PI 3-kinase pathway which can be addressed by drugs which will have less side effects than other drugs directed to targets upstream of PKN3. By having control over this particular fraction of effector molecules, i.e. the protein PKN3 and any further downstream molecule involved in the pathway, only a very limited number of parallel branches thereof or further upstream targets in the signalling cascade are likely to cause unwanted effects. Therefore, the other activities of the PI-3 kinase/PTEN pathway related to cell cycle, DNA repair, apoptosis, glucose transport, translation will not be influenced. Also, the insulin signalling is not induced which means that the diabetic responses or other side effects observed in connection with the use of LY294002 are actually avoided. LY294002 (2-(4-morpholinyl)-8-phenylchromone) is one of several chromone derivatives small molecule inhibitor developed by Lilly Research Laboratories (Indianapolis) as an inhibitor for PI-3K (Vlahos et al. 1994, JBC 269, 5241-5248). It targets their catalytic subunit of the PI-3K molecule, p110 and functions by competing with ADP binding in the catalytic centre. However, LY294002 cannot distinguish between different isoforms of p110 (alpha, beta, gamma, delta) which are suggested to have different cellular functions.

PKN3 is also further downstream of mTOR which is addressed by rapamycin. mTOR (mammalian Target Of Rapamycin), also known as Raft or FRAP, is acting downstream of PI 3-kinase to regulate processes such as the pp70 S6 kinase dependent entry into the cell cycle. mTOR acts as a sensor for growth factor and nutrient availability to control translation through activating pp70 S6 kinase and initiation factor 4E. mTOR function is inhibited by the bacterial macrolide rapamycin which blocks growth of T-cells and certain tumor cells (Kuruvilla and Schreiber 1999, Chemistry & Biology 6, R129-R136).

The fact that rapamycin and its derivatives are suitable drugs currently being used in the clinic proves that a drug target is the more helpful and has the less side effects, the more specific it is for a particular molecular mechanism as, e.g., demonstrated by Yu et al. (Yu, K. et al (2001) Endrocrine-RelatCanc 8, 249).

PKN3 is a member of the protein kinase C family all of which are said to be protein-serine/threonine kinases. Typically, this kind of protein kinase comprises one regulatory and one catalytic subunit and uses calcium ions and phospholipids as co-factors. Diacyl glycerols act as activator of this kind of protein kinase family. Members of the protein kinase C family are involved in several signalling pathways linked to hormones or neurotransmitters. These protein kinases regulate the activity of their target proteins by phosphorylation. It is known in the art that unphysiological continued activating of protein kinase C results in the transformed cellular phenotype that might lead to the generation of cancer.

The complete sequence of PKN3 as mRNA is available in databanks, e.g., under accession numbers gi 7019488 or NM_013355. Using the genetic code, the particular amino acid sequence may be deduced from this mRNA. Also, the amino acid sequence of PKN3 is available in databanks under the accession number gi 7019489 or NP_037487.1.

Homologues to human PKN3 may be found, among others, in *M. musculus, R norvegicus, A. thaliana, C. elegans, D. melanogaster* and *S. cerevisiae*. The percent identity and length of the aligned region is 67% and 279 amino acids, 51% and 866 amino acids, 38% and 305 amino acids, 36% and 861 amino acids, 63% and 296 amino acids and 44% and 362 amino acids, respectively, for the various species mentioned before. It will be acknowledged by the ones skilled in the art that any of these or other homologues will in principle be suitable for the practice of the present invention unless the drug generated using such homologue may still interact with the human protein kinase N beta or any other intended protein kinase N beta.

The human amino acid sequence may also be taken from ProtEST, accession number pir: JC7083 where the respective protein kinase N beta is referred to as JC7083 protein kinase. The gene for human protein kinase N beta is located on human chromosome number 9. cDNA sources for protein kinase N beta are in general a number of cancers and various fetal or embryonic tissues, more particularly, among others, stomach, adenocarcinoma, brain, breast, burkitt, lymphoma, cervix, chondrosarcoma, colon, fetal eyes, fetal lens, fetal eye anterior segment, fetal optic nerve, fetal retina, fetal retina foveal, fetal macular fetal choroid, fibrotheoma, germ line, nead neck, heart, kidney, large cell carcinoma, leiomyosarcoma metastatic chondrosarcoma, ovary, parathyroid, retinoblastoma, rhabdomyosarcoma, small cell carcinoma, squamous cell carcinoma, testis, and uterus. From this list it is obvious that the drug which is also referred to herein as a medicament, may in addition to any of the other diseases as disclosed herein and the diseased conditions as disclosed herein also be used for the treatment and/or prevention, of any of these diseases or any disease involving the specific cells, tissues or organs. These diseases and diseased conditions shall also be comprised by the term "disease as described herein".

The disease(s) as described herein as well as the diseased condition(s) as described herein which can be treated and/or prevented by the nucleic acid molecules and medicaments containing the same, according to the present invention also comprise tumorigenesis and metastasis. This applies particularly to those diseases as described herein and those diseased conditions as described herein, where the cells involved in such diseases or diseased conditions are PTEN negative which means that the tumor suppressor PTEN is not active or has a reduced level of activity. The diseases also comprise those diseases in which the PI 3-kinase pathway is involved in general. Besides metastatic tumors in particular, diabetes belongs to this kind of diseases and diseased conditions, respectively. Therefore, cells, particularly those which are involved in the disease or diseased condition as described herein and which are PTEN negative, are susceptible to the treatment by a drug the mode of action is such as to reduce or eliminate the activity of PKN3 in the respective cells involved. Accordingly, patients whose tumors are characterized by a preferably hyperactivated PI 3-kinase pathway, including but not limits to, either through amplification or mutation of genes encoding components of the PI 3-kinase pathway (p110, Akt) or are PTEN negative or who have cells which are PTEN negative, particularly if these cells are involved in the disease as described herein or in the diseased condition as described herein, can advantageously be treated using said drugs. Such reduction in activity may either stem from a reduction at the transcription level or at the level of the translation, i.e. the enzymatic activity of PKN3. Without wishing to be bound by any theory, the latter aspect, i.e. modifying the activity of the PKN3 is also caused by the characteristics of PKN3, namely that the enzymatic activity of PKN3 can also be up- and down-regulated, more preferably down-regulated.

A further group of patients who can advantageously be treated using said drugs are those who suffer from cancers which have a high incidence for loss of PTEN function, especially in late stage tumors (Cantley and Neel, 1999). Loss of PTEN correlates with increased aggressive and invasive behavior of the respective tumor cells.

It is to be acknowledged that the various diseases described herein for the treatment and prevention of which the pharmaceutical composition according to the present invention may be used, are also those diseases for the prevention and/or treatment of which the medicament described herein can be used, and vice versa.

As used herein the term treatment of a disease shall also comprise prevention of such disease.

Further features, embodiments and advantages may be taken from the following figures.

FIG. 1 is a schematic diagram illustrating the involvement of PKN3 in the PI 3-pathway.

FIG. 2 shows the result of a Western Blot analysis of a knock-down experiment using PKN3 specific siRNAs in human cell lines (HeLa, HUVEC) and a mouse cell line (EOMA).

FIG. 3 shows the result of a knock down experiment using different concentrations of PKN3 specific siRNA molecule formulated as a lipoplex for determining the IC 50 of the siRNA molecules in both HeLa and HUVEC cells.

FIG. 4 shows the result of a Western Blot analysis of a knockdown experiment using a PKN3 specific siRNA molecule and a PKN3 specific antisense molecule as a control, whereby the efficacy of said molecules in terms of knock-down potency was assessed at different time points.

FIG. 5 shows the result of a Western Blot analysis of a knockdown experiment, whereby different concentrations of PKN3 specific siRNA lipoplexes were used which either exhibited a phosphate group at the 3' end or not.

FIG. 6 shows the result of a Western Blot analysis of a knockdown experiment using different PKN3 specific siRNA molecules (FIG. 6A) and photomicrographs illustrating the loss-of-PKN3 function on HUVEC growth on extracellular matrix (FIG. 6B).

FIG. 7 illustrates the experimental design for testing the in vivo efficacy of PKN3 specific siRNA molecules (FIG. 7A) and the impact of such molecules on tumor volume (FIG. 7B) and body weight (FIG. 7C) in a s. c. PC-3 xenograft tumor mouse model.

FIG. 8 illustrates the experimental design for testing the in vivo efficacy of a PKN3 specific siRNA molecule (FIG. 8A) and the impact of different doses of such siRNA molecule expressed as percentage of body weight or tumor volume (FIG. 8B), and the impact of different treatment schedules using such molecule expressed as percentage of body weight or tumor volume (FIG. 8C) in a s. c. PC-3 xenograft tumor mouse model.

FIG. 9 illustrates the experimental design for testing the in vivo efficacy of a PKN3 specific siRNA molecule (FIG. 9A), the impact of said molecule on prostate tumor volume and lymph node metastases (FIG. 9B) and the impact of said molecule on the reduction of PKN-3 and Tie2 mRNA in lung tissue in an intraprostatic PC-3 xenograft tumor mouse model (FIG. 9C).

FIG. 10 illustrates the experimental design for testing the in vivo efficacy of different treatment schemes using a specific siRNA molecule upon systemic administration (FIG. 10A) and the impact of such different treatment schemes on the volume of the prostate tumor (FIG. 10 B) and on the volume of lymph node metastases (FIG. 10C) in an intraprostatic PC-3 xenograft tumor mouse model.

FIG. 11 illustrates the experimental design for testing the in vivo efficacy of various doses of a PKN-3 specific siRNA molecule upon systemic administration (FIG. 11A) and the impact of said various doses on the volume of the prostate tumor (FIG. 11B) and on the volume of the lymph node metastases (FIG. 11C).

FIG. 12A shows the compounds forming the lipoplex.

FIG. 12B shows a schematic illustrating the structure of the lipoplexes in accordance with the present invention compared to liposomes.

FIG. 13 shows the result of a Western Blot analysis of a knock down experiment using a PKN3 specific siRNA molecule having either 19 base pairs or 23 base pairs.

FIG. 14 shows the result of a Western Blot Analysis of a knock down experiment using different PKN3 specific siRNA molecules.

FIG. 15 shows the result of a Western Blot Analysis of a knock down experiment using siRNA molecules having either 19 base pairs or 23 base pairs in three different cell lines, whereby the siRNA molecules are used at different concentrations.

FIG. 16 shows the experimental design for testing the in vivo efficacy of PKN3 specific siRNA molecules (FIG. 16A) and the impact of such PKN3 specific siRNA molecules having either 19 base pairs or 23 base pairs, on the reduction in prostate tumor volume (FIG. 16B), lymph node metastases volume (FIG. 16C) and lymph node metastatic spread (FIG. 16D) in an orthotopic prostate cancer mouse model.

FIG. 17 shows the experimental design for testing the in vivo efficacy of various doses of a PKN3 specific siRNA molecule comprising 23 base pairs (FIG. 17A) and the impact of such various doses on the reduction in prostate tumor volume (FIG. 17B), lymph node metastases volume (FIG. 17C) and lymph node metastatic spread (FIG. 17D) in an orthotopic prostate cancer mouse model.

EXAMPLE 1

Materials and Methods

In Vitro Transfection and Immunoblotting; Antibodies

Cell lines were transfected with siRNA using the cationic liposomes described above. Briefly, about 12 hours after cell seeding different amounts of siRNA-lipoplex solution diluted in 10% serum containing medium were added to the cells to achieve transfection concentrations in a range of 1-50 nM siRNA. After transfection (48 h) cells were lysed and subjected to immunoblotting as described (Klippel et al., 1998). Protein concentration was determined with a DC Protein Assay (BioRad) and equal amounts were loaded for immunoblot analysis using the following antibodies: Rabbit anti-PTEN (Ab-2, Neomarkers), Akt-1, rabbit anti-PKN3 (Leenders et al., 2004), Cell Lines PC-2, HeLa, HUVEC (human umbical vein endothelial cells), and EOMA cell lines were and cultivated according to the ATCC's recommendation Tumor Xenograft Male Hsd:NMRI-nu/nu mice (8 weeks old) were used in this study. For tumor therapy experiments on established tumor xenografts, a total of $5.0 \times 10^6$ tumor cells/100 µl PBS) were implanted subcutaneously. Tumor volume was determined using a caliper and calculated according to the formula volume=(length×width$^2$)/2. For tumor therapy experiments siRNA-lipoplex solution was administered i.v. by low pressure, low volume tail vein injection. In the orthotopic tumor model $2.0 \times 10^6$ PC-3 cells/30 µl PBS were injected into the left dorsolateral lobe of the prostate gland under total body anesthesia (Stephenson et al., 1992). Animals were killed 50 days post-operation and volumes of tumors (prostate gland) and regional metastases (caudal, lumbar and renal lymph node metastases) were determined as mentioned above.

For i. v. treatment, siRNA-lipoplexes were performed by administering siRNA lipoplexes intravenously through single tail vein injection of 200 µl solution at a final dose of 1.88 mg/kg siRNA and 14.5 mg/kg lipid or for different schedules variant doses thereof (as indicated).

Statistical Analysis

Data are expressed as means±s.e.m. Statistical significance of differences was determined by the Mann-Whitney U test. P values <0.05 were considered statistically significant.

Matrigel Assay

To assay cell growth on Matrigel matrix, HUVEC were transfected with siRNAs for 48 h. After trypsinization, the cells were seeded in duplicates on 24-well plates (110,000 cells per well) pre-coated with 250 µl Matrigel basement membrane matrix) and microscopic photographs were taken at ×1.25 or ×2.5 magnification with an Axiocam camera attached to an Axiovert S100 microscope 20 hours post replating.

EXAMPLE 2

PKN3 siRNA Molecules

The molecules in accordance with the present invention which are also referred to herein as siRNA molecules (AtuR- NAi, see Table 1a and 1b.) and which were used in this study are as such described in (Czauderna et al., 2003) and were synthesized by BioSpring (Frankfurt a. M., Germany).

The duplexes of said molecules are formed by the respective sense and antisense strands, which are each indicated in Table 1a and 1b in 5'->3' direction. Therefore, the double-stranded molecule is formed by combining the respective sense and antisense strand, e.g. PKN3-hm-1s and PKN3-hm-1as forming a molecule having a double-stranded structure, which is in the specific example also referred to herein as PKN3 (1). The molecules are blunt ended, however, each strand forming the double-stranded molecule has a phosphate attached to the 3'-end, more specifically to the terminal 3'OH end. The molecules are chemically stabilized by alternating 2'-O-methyl sugar modification on both strands, whereby unmodified nucleotides face modified on the opposite strand as also may be taken from Table 1a. These double-stranded molecules are particularly preferred embodiments of the nucleic acid molecules in accordance with the present invention.

TABLE 1a

```
PKN3 (1):
s         agcugaagaucaaggaggg   (SEQ. ID. No. 2)
as        ccuccuugaucuucagcu    (SEQ. ID. No. 3)

PKN3 (2):
s         cuugaggacuuccuggaca   (SEQ. ID. No. 4)
as        uguccaggaaguccucaag   (SEQ. ID. No. 5)

PKN3 (3):
s         uugaggacuuccuggacaa   (SEQ. ID. No. 6)
as        uuguccaggaaguccucaa   (SEQ. ID. No. 7)

PKN3 (4):
s         aggacuuccuggacaaugc   (SEQ. ID. No. 8)
as        gcauguccaggaaguccu    (SEQ. ID. No. 9)

PKN3 (5):
s         ccuggacaaugccugucac   (SEQ. ID. No. 10)
as        gugacaggcauuguccagg   (SEQ. ID. No. 11)

PKN3 (6):
s         gggacacuuugggaagguc   (SEQ. ID. No. 12)
as        gaccuucccaaagugucc    (SEQ. ID. No. 13)

PKN3 (7):
s         uugggaaggccucccuggu   (SEQ. ID. No. 14)
as        accaggaggaccuucccaa   (SEQ. ID. No. 15)

PKN3 (8):
s         cuccagccaugccugcuuu   (SEQ. ID. No. 16)
as        aaagcaggcauggcuggag   (SEQ. ID. No. 17)

PKN3 (9):
s         auucagaagcuccuccaga   (SEQ. ID. No. 18)
as        ucuggaggagcuucugaau   (SEQ. ID. No. 19)

PKN3 (10):
s         ucagaagcuccuccagaag   (SEQ. ID. No. 20)
as        cuucuggaggagcuucuga   (SEQ. ID. No. 21)

PKN3 (11):
s         cagaagcuccuccagaagu   (SEQ. ID. No. 22)
as        acuucuggaggagcuucug   (SEQ. ID. No. 23)

PKN3 (12):
s         ucuucaggaccaccaacug   (SEQ. ID. No. 24)
as        caguuggugguccugaaga   (SEQ. ID. No. 25)

PKN3 (13):
s         cuucaggaccaccaacugg   (SEQ. ID. No. 26)
as        ccaguuggugguccugaag   (SEQ. ID. No. 27)
```

TABLE 1a-continued

```
PKN3 (14):
s         ucaggaccaccaacuggca   (SEQ. ID. No. 28)
as        ugccaguuggugguccuga   (SEQ. ID. No. 29)
```

Nucleotides with 2'-O-methyl modifications are underlined; from such underlining it is evident that every second nucleotide has this kind of modification, whereby such modification starts with the first nucleotide on the antisense strand, and with the second nucleotide on the sense strand (under the proviso that both the sense strand and the antisense strand are depicted in 5'-3' direction from left to right).

s stands for the sense strand which is also referred to herein as the second strand; and as stands for the antisense strand which is also referred to herein as the first strand whereby the first strand comprises a first stretch of contiguous nucleotides and said first stretch is at least partially complementary to a target nucleic acid whereby the target nucleic is, as used herein, preferably the nucleic acid which is to be degraded or destilized.

These molecules are also referred to herein as PKN3 specific siRNAs and were screened in two human cell lines, namely HeLa, HUVEC, and one mouse cell line (EOMA). 20 nM of siRNAs were transfected and immunoblots were performed from whole cell lysates 48 h post transfection as described in example 1. The results are depicted in FIG. 2. As may be taken from FIG. 2, particularly preferred are nucleic acid molecules PKN3 (2), PKN3 (3), PKN3 (4), PKN3 (5), PKN3 (6), PKN3 (8).

An even more preferred molecule is PKN3 (3) which was made subject to further studies.

Based on PKN3 (3) further siRNA molecules were designed which are presented in the following table 1b and are annotated as PKN3-23-v1 for the molecule consisting of the PKN3-hm-3A23v1 and PKN3-hm-3B23v1 molecules, i.e. single strands, as PKN3-23-v2 for the molecule consisting of the PKN3-hm-3A23v2 and PKN3-hm-3B23v2 molecules, i.e. single strands, as PKN3-23-v3 for the molecule consisting of the PKN3-hm-3A23v3 and PKN3-hm-3B23v3 molecules, i.e. single strands, as PKN3-23-v4 for the molecule consisting of the PKN3-hm-3A23v4 and PKN3-hm-3B23v4 molecules, i.e. single strands, and as PKN3-23-v5 for the molecule consisting of the PKN3-hm-3A23v5 and PKN3-hm-3B23v5 molecules, i.e. single strands.

The way these siRNA molecules are presented and designed is the same as described in connection with the siRNA molecules contained in table 1a. As may be taken from table 1b, starting from PKN3 (3), referred to in table 1b as PKN3-hm-3A19/PKN3-hm-3B19, a total of four nucleotides was added at the 3' end of the sense strand and the 5' end of the antisense strand (PKN3-23-v1), a total of four nucleotides at the 5' end of the sense strand and a total of four nucleotides at the 3' end of the antisense strand (PKN3-23-v2), one nucleotide at the 5' end and three nucleotides at the 3' end of the sense strand and three nucleotides at the 5' end and one nucleotide at the 3' end of the antisense strand (PKN3-23-v3), two nucleotides at the 5' end and two nucleotides at the 3' end of the sense strand and two nucleotides at the 5' end and two nucleotides at the 3' end of the sense strand (PKN3-23-v4), and three nucleotides at the 5' end and one nucleotide at the 3' end of the sense strand and one nucleotide at the 5' end and three nucleotides at the 3' end of the antisense strand (PKN3-23-v5). The newly added nucleotides are shown in table 1b in italics.

TABLE 1b

```
PKN3 (3)
PKN3-hm-3B19      s    uugaggacuuccuggacaa        (SEQ. ID. No. 6)
PKN3-hm-3A19      as   uuguccaggaaguccucaa        (SEQ. ID. No. 7)

PKN3-23-v1
PKN3-hm-3A23v1    as   uuguccaggaaguccucaagucu    (SEQ. ID. No. 31)
PKN3-hm-3B23v1    s    agacuugaggacuuccuggacaa    (SEQ. ID. No. 30)

PKN3-23-v2
PKN3-hm-3A23v2    as   ggcauuguccaggaaguccucaa    (SEQ. ID. No. 33)
PKN3-hm-3B23v2    s    uugaggacuuccuggacaaugcc    (SEQ. ID. No. 32)

PKN3-23-v3
PKN3-hm-3A23v3    as   auuguccaggaaguccucaaguc    (SEQ. ID. No. 35)
PKN3-hm-3B23v3    s    gacuugaggacuuccuggacaau    (SEQ. ID. No. 34)

PKN3-23-v4
PKN3-hm-3A23v4    as   cauuguccaggaaguccucaagu    (SEQ. ID. No. 37)
PKN3-hm-3B23v4    s    acuugaggacuuccuggacaaug    (SEQ. ID. No. 36)

PKN3-23-v5
PKN3-hm-3A23v5    as   gcauuguccaggaaguccucaag    (SEQ. ID. No. 39)
PKN3-hm-3B23v5    s    cuugaggacuuccuggacaaugc    (SEQ. ID. No. 38)
```

The siRNA molecules of table 1b were tested for their knock-down efficacy and compared to the one of PKN3 specific siRNA having a length of 19 nucleotides, more specifically PKN3 (3). For such purpose, HeLa B cells were plated in 6 wells (40 k), transfected 16 h later with 20 nM and lysed for protein extraction 48 h after transfection. If not explicitly indicated to the contrary, the techniques and procedures used in connection with these siRNA molecules are those described herein in the example part and more specifically described in example 1.

A Western Blot of lysates probed with anti-PKN3 antibody and anti-PTEN antibody, with the latter acting as loading control, is depicted in FIG. 13. As may be taken from FIG. 13, PKN3-23-v1 is particularly effective, followed, in terms of efficacy, by PKN3-23-v4, PKN3-23-v5, PKN3-23-v2 and PKN3-23-v3. A luciferase specific siRNA molecule comprising as the sense strand Luc-siRNA-2B (cguacgcggaauacuucga, SEQ. ID. No 56) and as the antisense strand Luc-siRNA-2A (ucgaaguauuccgcguacg, SEQ. ID. No 57) was used as control (KO).

Further potential siRNA molecules were screened which are depicted in Table 2, whereby the way of presentation and modification is the same as described in connection siRNA molecules shown in Tables 1a and 1b above.

TABLE 2

```
Name                       Sequence

PKN3-23-19
PKN3-23-hmr-19A    as   caguuggugguccugaagaaugg    (SEQ. ID. No. 41)
PKN3-23-hmr-19B    s    ccauucuucaggaccaccaacug    (SEQ. ID. No. 40)

PKN3-23-20
PKN3-23-hmr-20A    as   ugccaguuggugguccugaagaa    (SEQ. ID. No. 43)
PKN3-23-hmr-20B    s    uucuucaggaccaccaacuggca    (SEQ. ID. No. 42)

PKN3-23-21
PKN3-23-hmr-21A    as   cuucuggaggagcuucugaauga    (SEQ. ID. No. 45)
PKN3-23-hmr-21B    s    ucauucagaagcuccuccagaag    (SEQ. ID. No. 44)

PKN3-23-22
PKN3-23-hmr-22A    as   accaggaggaccuucccaaagug    (SEQ. ID. No. 47)
PKN3-23-hmr-22B    s    cacuugggaagguccuccuggu     (SEQ. ID. No. 46)

PKN3-23-23
PKN3-23-hmr-23A    as   acuucuggaggagcuucugaaug    (SEQ. ID. No. 49)
PKN3-23-hmr-23B    s    cauucagaagcuccuccagaagu    (SEQ. ID. No. 48)

PKN3-23-24
PKN3-23-hmr-24A    as   agcuuccucuccuugggggugcc    (SEQ. ID. No. 51)
PKN3-23-hmr-24B    s    ggcaccccaaggagaggaagcu     (SEQ. ID. No. 50)

PKN3-23-25
PKN3-23-hmr-25A    as   aggaccuucccaaagugucccg     (SEQ. ID. No. 53)
PKN3-23-hmr-25B    s    cggggacacuugggaaggucu      (SEQ. ID. No. 52)

PKN3-23-26
PKN3-23-hmr-26A    as   agcugcuccagggggcgguugga    (SEQ. ID. No. 55)
PKN3-23-hmr-26B    s    uccaaccgcggccugagcagcu     (SEQ. ID. No. 54)
```

These siRNA molecules depicted in table 2 were screened in a primary screen in HUVEC cells as described above. Cells were plated in 6 wells (40 k), transfected 16 h later with 20 nM siRNA and 1 μg/ml AtuFECT01 and lysed for protein extraction 72 h after transfection. A Western Blot of lysates probed with anti-PKN3 and anti-PTEN, with the latter acting as loading control, are depicted in FIG. 14, whereby ut stands for untreated; Luci stands for Luciferase siRNA as defined above; and co3 is

```
PKN3-23-v1
PKN3-hm-3A23v1    as    uuguccaggaaguccucaagucu

PKN3-hm-3B23v1    s     agacuugaggacuuccuggacaa
```

If not explicitly indicated to the contrary, the techniques and procedures used in connection with these siRNA molecules are those described herein in the example part and more specifically described in example 1.

EXAMPLE 3

Lipoplex Formulation of PKN3 Specific siRNA Molecules

The lipoplex formulation was prepared as essentially described in Santel (Santel et al. 2006).

The cationic lipid AtuFECT01 (β-L-arginyl-2,3-L-diaminopropionic acid-N-palmityl-N-oleyl-amide trihydrochloride, Atugen AG), the neutral phospholipid 1,2-diphytanoyl-sn-glycero-3-phosphoethanolamine (DPhyPE) (Avanti Polar Lipids Inc., Alabaster, Ala.) and the PEGylated lipid N-(Carbonyl-methoxypolyethyleneglycol-2000)-1,2-distearoyl-sn-glycero-3-phospho-ethanolamine sodium salt (DSPE-PEG) (Lipoid GmbH, Ludwigshafen, Germany) were mixed in a molar ratio of 50/49/1 by lipid film re-hydration in 300 mM sterile RNase-free sucrose solution to a total lipid concentration of 4.34 mg/ml. If not indicated to the contrary, typically a single i. v. injection for a 30 g mouse was carried out at a standard dose of 1.88 mg/kg siRNA and 14.5 mg/kg lipid. Also, if not indicated to the contrary, the PKN3 specific siRNA molecule is the PKN3 (3) molecule as defined in example 2. The various compounds forming the lipoplexes in accordance with the present invention, including PKN3 (3), are depicted in FIG. 12A whereby it is to be understood that the specific siRNA molecule may, in principle, be any siRNA molecule as disclosed herein, preferably any siRNA molecule as shown in tables 1a and 1b.

FIG. 12B shows a schematic illustrating the siRNA lipoplex, i.e. the complex formed between or from the siRNA molecules together with the aforementioned lipids, i.e. the cationic lipid, the DPhyPE which is also referred to as helper lipid, and the PG-lipid, i.e. DSPE-PEG. The bold nucleotides of the PKN3-specific siRNA indicated a 2'-O-methyl modification of the individual nucleotide.

EXAMPLE 4

Determination of IC50

The IC50 of the lipoplex formed by PKN3 (3) molecules together with the lipids specified in example 3, which is also referred to as siRNA-PKN3(3)-lipoplex was determined after transfection in HeLa and HUVEC cells. Protein lysates were prepared 48 h post transfection and immunoblots with PKN3 and PTEN-specific antibodies.

The concentrations of the lipoplexed (formulated in a lipoplex) siRNA molecule ("siRNA-PKN3 (3)") were 1, 5, 10 and 20 nM.

The results are depicted in FIG. 3.

From FIG. 3 it may be taken that in HeLa cells already a concentration of 5 nM of siRNA-PKN3 (3) is suitable to significantly knockdown PKN3 at the protein level. The same is also true for HUVEC cells, whereby a slightly higher concentration is needed to reach the very same extent of knock down as in HeLa cells. PTEN was used as a loading control.

Additionally, lipoplexes formed by PKN3 molecules as depicted in table 1b herein, more specifically PKN3-23-v1, was subject to dose titration in comparison to PKN3 (3) being a 19mer, in cell lines HUVEC and EOMA, respectively. As described in the preceding examples, cells were plated in 6 wells (40 k), transfected 16 h later with the indicated concentration of siRNA and lysed for protein extraction 48 h after transfection. A Western Blot of lysates probed with anti-PKN3 antibody and anti-PTEN antibody, with the latter acting as loading control, is depicted in FIG. 15.

As may be taken from FIG. 15 the PKN3-23-v1 siRNA is comparable in efficacy to the one of PKN3 (3). The IC50 of the 19 mer and 23 mer molecule are assessed by cell culture transfection experiments followed by semiquantitative immunoblot and shows similar potency (IC50~5 nM) for three different cell lines. It is worth pointing out that EOMA is a mouse derived endothelial cell line indicating the activity for mouse and human.

EXAMPLE 5

Transient Effect of PKN3 Specific siRNA Molecules

To show the transient character of the knockdown effect of a PKN3 specific siRNA molecule, namely siRNA-PKN-3 (3), and of a PKN3 specific antisense molecule (GB control) (Leenders et al., 2004) these molecules were transfected into HeLa cells. Protein lysates where prepared at 48 h, 96 h, 144 h and 192 h. In each case, the cells were exposed to siRNA lipoplexes containing the PKN3 (3) molecules, as described in example 3 for 24 h and said siRNA lipoplexes were removed after said 24 hours.

The results are depicted in FIG. 4.

From FIG. 4 it may be taken, that an effect of the siRNA PKN3(3) on PKN3 at the protein level can be observed until 96 h, whereby after 144 h the efficacy of the particular siRNA molecule seems to be reduced and after 192 h essentially the knock down effect can no longer be observed. Compared to the GB control, the siRNA molecule according to the present invention shows thus a longer lasting activity compared to an antisense molecule the knock down of which is significantly diminishing already after 96 h.

EXAMPLE 6

Impact of a Phosphate Group Attached to the 3' End of an siRNA Molecule According to the Present Invention In this example, the impact of a 3'-phosphate modification at the 3'-end of both the sense and the antisense strand forming the double-stranded structure or molecule in accordance with the present invention was studied, whereby PKN3 (3) was used as the knockdown mediating nucleic acid molecule and said nucleic acid molecule was formulated so as to form the respective lipoplexes as described in example 3 prepared.

The thus obtained lipoplexes were tested in HeLa cells, whereby different amounts of said siRNA molecule and lipoplexes, respectively, were transfected and protein lysates were prepared 48 h post transfection. Immunoblots were analysed as described herein and the results are shown in FIG. 5.

As may be taken from FIG. 5, the phosphate modification factually has no impact on the efficacy of the siRNA molecule and the lipoplexes containing the same.

EXAMPLE 7

Loss of PKN3 Function on HUVEC Growth on Extracellular Matrix

To further show that there are also some physiological and morphological changes upon knockdown of PKN3 using the molecules according to the present invention, an extracellular matrix growth assay was used (Leenders et al., 2004).

More specifically, HUVECs were transfected with 4 different siRNA-PKN3 lipoplexes, individually and separately containing PKN3 (1), PKN3 (3), PKN3 (4) and PKN3 (5) as the siRNA molecule, and with siRNA Luc-lipoplex (20 nM) as a control. The cells were kept growing to confluency within the first 48 hours of transfection. After 48 hours cells were trypsinized, replated with equal cell numbers (110,000 cells) and were plated on matigel containing 24 wells.

Representative microscopic pictures were taken to monitor changes in HUVEC cell growth at 20 h post replating. The results are depicted in FIG. 6.

As expected, in the case of potent siRNA PKN3 lipoplexes, preferably PKN3 (3) lipoplexes and PKN3 (5) lipoplexes, a pronounced inhibition of growth was observed.

EXAMPLE 8

Inhibition of Subcutaneous s.c. PC-3 Xenograft Tumor Growth

A PC-3 xenograft tumor model was generated by subcutaneous injection of PC3 cells. The tumor thus generated was subsequently treated with the lipoplexes described in example 3. The siRNA molecule contained in such lipoplex was PKN3 (3). The basic experimental design is depicted in FIG. 7A. A total of three different treatment groups were established with each group consisting of six mice. The first group received sucrose only, the second group received lipoplexes containing siRNA against luciferase (siRNALuc-lipolex) and the third group received lipoplexes containing siRNA specific for PKN3 (siRNA PKN3-lipoplex).

After tumor cell inoculation the various agents were administered starting from 25 to day 35 on. The injections were performed eight times a day i. v. The siRNA lipoplex doses were 1.88 mg/kg siRNA and 14.5 mg/kg of the total lipid (Santel et al., 2006a; Santel et al., 2006b).

In parallel, the PKN3-23-v1 siRNA molecule was assessed in comparison to PKN3 (3). The respective basic experimental design is depicted in FIG. 16A, whereby after tumor cell inoculation the various agents, i.e. sucrose, PKN3 (3) and PKN3-23-v1, were administered starting from day 29 to day 47, whereby the administration was such that 10×i. v. injections were performed every second day (in a group of twelve mice). The siRNA lipoplex doses were 2.8 mg/kg siRNA and 21.7 mg/kg total lipid (Santel et al., 2006a, Santel et al., 2006b).

The result of such treatment scheme is depicted in FIG. 7B and FIG. 7C for PKN3 (3) and in FIGS. 16B to 16D for the PKN3-23-v1 siRNA molecule in comparison to PKN3 (3).

As may be taken from FIG. 7B the growth of established PC-3 xenografts was significantly inhibited with siRNA PKN3 lipoplexes (diamonds) in comparison with siRNA Luc-lipoplex (triangles) treated as indicated (standard dose 1.88 mg/kg/day siRNA; 14.5 mg/kg/day lipid; arrow) or isotonic sucrose (solid spheres). Changes in body weights were monitored during the treatment as shown in FIG. 7B. The individual data represents the mean of daily tumor volume s.e.m. Only a little decrease in body weight could be observed upon administration of the various lipoplexes confirming that there is only a minimum impact, if at all, of the lipid component of the lipoplexes on animal's health.

As may be taken from FIGS. 16B, 16C and 16D, both siRNA molecules tested, i.e. PKN3 (3), i.e. the "19mer", and PKN3-23-v1, i.e. the "23mer", show the same efficacy in this prostate tumor model as expressed in reduction of prostate tumor volume (FIG. 16B), reduction in lymph node metastases volume (FIG. 16C) and lymph node metastatic spread (FIG. 16D).

EXAMPLE 9

Inhibition of Subcutaneous PC-3 Xenograft Tumor Growth: Impact of Different Lipoplex Doses The underlying experiment was carried out in order to investigate the impact of different lipoplex doses on the inhibition of subcutaneous PC-3 xenograft tumor growth. More specifically, siRNA PKN3(3) lipoplexes were used. The lipoplexes were prepared as described in example 3. The experimental design can be taken from FIG. 8A. The treatment groups consisted of 6 mice, whereby one group of animals received sucrose as a negative control, whereas the other group received siRNA PKN3-lipoplexes, more specifically siRNA PKN3 (3) lipoplexes. After s. c. tumor cell inoculation the animals were administered from day 22 to 38 on eleven i.v. injections daily and the survival was assessed until day 67.

The formulation of the siRNA lipoplex formulation was as follows: 1.88 mg/kg siRNA+14.5 mg/kg atuFect01/1% PEG; the different lipoplex doses were as follows:
0.94 mg/kg siRNA daily d22-32
1.88 mg/kg siRNA daily d22-32
1.88 mg/kg siRNA bidaily 50% dose d22-28
1.88 mg/kg every 2nd day d22-38

The result is depicted in FIG. 8B. It may be taken from FIG. 8B that a dose of 1.88 mg/kg daily resulted in a significant decrease of the tumor volume, whereby the body weight changed only slightly and no negative effects could be observed for the lipoplex formulations as such.

EXAMPLE 10

Inhibition of Subcutaneous PC-3 Xenograft Tumor Growth: Impact of Different Treatment Regimen The experimental design was as described in connection with example 8.

The results are depicted in FIG. 8C. More specifically it may be taken from FIG. 8C that the effect of the treatment schedule investigated in this example, did not differ in terms of impact of tumor volume. However, the treatment schedule consisting of twice daily, daily and every second day showed the same tumor growth inhibition, indicating that a treatment with the PKN3-siRNA lipoplex every second day is sufficient for maintaining therapeutic effects. In addition a treatment twice daily resulted in a significant decrease in body weight suggesting a dose limiting dose without additional therapeutic benefit (Santel et al., 2006a).

EXAMPLE 11

Systemic Treatment of Mice with siRNA PKN3(3) Lipoplexes in an Orthotopic Xenograft Tumor Model This experiment was carried out in order to study the impact of systemic treatment of mice with siRNA PKN3 lipoplexes and more specifically siRNA-PKN3 (3) lipoplexes on tumor growth in an orthotopic xenograft tumor model, (for experimental details see (Santel et al., 2006a)).

The experimental design to analyze the efficacy of siRNA PKN3 lipoplex treatment in an orthotopic PC-3 prostate tumor and lymph node metastases model is depicted in FIG. 9A. A total of four treatment groups each consisting of 9 mice were defined, namely groups receiving sucrose, siRNA Luc-lipoplex, siRNA PKN3-lipoplex and siRNA Tie2-lipoplex. After intraprostatic tumor cell inoculation siRNA lipoplex doses consisting of 1.88 mg/kg siRNA and 14.5 mg/kg atuFect01/1% PEG were injected from day 35 to 49 on with eight i.v. injections every second day. On day 35 a pre-treatment control was performed.

From this experiment, a decrease in the volume of the prostate PC-3 tumor and lymph node metastases in mice after treatment with the indicated siRNA lipoplexes was observed compared to the groups treated with sucrose or luciferase specific siRNA molecules (siRNALuc) which is more specifically depicted in FIG. 9B (volume size of prostate tumor and volume of lymph node metastases).

The tumor metastases volume before the start of the treatment are indicated on the left (d35, control). Statistical significance is indicated by asterisk. As may be taken from said figures, the PKN3 specific siRNA molecule, more specifically the lipoplex containing the same, was highly effective with regard to reducing both the volume of the prostate tumor and the volume of the lymph node metastases.

To demonstrate in vivo RNA interference by i.v. administration of PKN3-siRNA lipoplex the mRNA knockdown in lung tissue was analyzed. More specifically, reduction of PKN-3 and Tie2 mRNA levels in lung tissue from mice treated with corresponding siRNA lipoplexes as revealed by quantitative TaqMan reverse transcription-polymerase chain reaction is depicted in FIG. 9C. The relative average amount of Tie2 or PKN3 mRNA levels in the lung normalized to CD34 mRNA is shown to demonstrate in vivo lipoplex mediated interference in vivo. A control TIE-2 receptor specific siRNA lipoplex was tested in parallel demonstrating as well a target specific mRNA reduction (FIG. 9, right panel) but did not reveal a significant inhibition of tumor growth or formation of lymph node metastasis, when compared to a negative Luciferase specific siRNA-lipoplex. These data indicate a target gene specific therapeutic effect with the PKN3-siRNA-lipoplex.

EXAMPLE 12

Systemic Treatment of Mice with siRNA-PKN3(3)-Lipoplexes in an Orthotopic Xenograft Tumor Model: Impact of Treatment Schedule This experiment was performed in order to test different treatment schedules in connection with systemic treatment of mice with siRNA-PKN3-lipoplexes and more specifically siRNA-PKN3 (3) lipoplexes in an orthotopic xenograft tumor model.

The experimental set up is depicted in FIG. 10A. There were two treatment groups with each group consisting of nine mice which were either administered sucrose or siRNA PKN3 lipoplex. After intraprostatic tumor cell inoculation, there were 10/7×i.v. injections every second or every third day from day 35 to 53 on. Two different siRNA lipoplex doses were employed, as follows: 1.88/2.8 mg/kg siRNA 14.5/21.7 mg/kg atuFect01/1% PEG, i.e. with 14.5/21.7 mg/kg total lipid.

The results are depicted as volume of prostate tumor (FIG. 10B) and as volume of lymph node metastases (FIG. 10C). For both parameter tumor volume and LN metastasis formation an inhibition was observed, however no significant increase in efficacy was observed with a treatment every second day when compared to a treatment every third day. However with the higher daily dose (2.8 mg/kg siRNA) a more pronounced inhibition of metastasis formation is observed. These data shows that the siRNA mediated inhibition is not restricted to a daily i.v. administration and the therapeutic effect can be achieved with treatments every second day.

EXAMPLE 13

Systemic Treatment of Mice with siRNA-PKN3(3)-Lipoplexes in an Orthotopic Xenograft Tumor Model: Impact of Different Doses This experiment was performed in order to test different doses of siRNA-PKN3 lipoplexes in connection with systemic treatment of mice with such lipoplexes and more specifically siRNA-PKN3 (3) lipoplexes (FIG. 11) and siRNA-PKN3-23-v1 (FIG. 17) in an orthotopic xenograft tumor model.

The experimental set up is depicted in FIG. 11A. There were three treatment groups with each group consisting of ten mice which were either administered sucrose, siRNA-PKN3 lipoplex or lipoplex only. After intraprostatic tumor cell inoculation, there were 10×i.v. injections every second day from day 28 to 46 on. The siRNA lipoplex doses were as follows: 0.7/1.4/2.8 mg/kg siRNA; 5.4/10.9/21.7 mg/kg of total lipid (in the lipoplex, all three together:atuFect01/helper lipid/1% PEG). The three dosage regimens were administered by i.v. injection every second day.

The results are depicted as volume of prostate tumor (FIG. 11B) and as volume of lymph node metastases (FIG. 11C). In both cases, a significant inhibition is observed with daily doses of 2.8 mg or 1.4 mg siRNA/kg indicating a therapeutic window for these siRNA molecules.

Also in case of the siRNA PKN3 lipoplex comprising PKN3-23-v1 as siRNA species rather than PKN3 (3), there were three different treatment groups with each group consisting of 7 to 8 mice to which either sucrose, siRNA-PKN3 lipoplex or lipoplex only was administered. After intraprostatic tumor cell inoculation, there were 15×i.v. injections every 4$^{th}$ day from day 7 to day 63 on. The siRNA lipoplex doses were 1.4 mg/kg siRNA (10.9 mg total lipid/kg)/and 0.7 mg/kg siRNA (5.4 mg total lipid/kg), respectively.

The results are depicted as prostate tumor volume (FIG. 17B) and as volume of lymph node metastases (FIG. 17C). In both cases, a significant inhibition is observed with doses of 1.4 mg/kg and 0.7 mg/kg siRNA, respectively, indicating a therapeutic window for these siRNA molecule doses.

Additionally, the body weight of the mice post cell challenge has been recorded and is depicted in FIG. 17D. From this figure, it may be taken that under such treatment regimen the body weight of the mice is not decreasing which indicates no overall toxic effects with bodyweight being a general indicator of animal health.

REFERENCES

To the extent it is referred herein to various documents of the prior art, such documents the complete bibliographic data of which read as follows, are incorporated herein in their entirety by reference.

Agrawal, S. and Akhtar, S. (1995) Advances in antisense efficacy and delivery. *Trends Biotechnol,* 13, 197-199.

Akhtar, S. and Juliano, R. L. (1992) Cellular uptake and intracellular fate of antisense oligonucleotides. *Trends Cell Biol,* 2, 139-144.

Boado, R. J., Tsukamoto, H. and Pardridge, W. M. (1998) Drug delivery of antisense molecules to the brain for treatment of Alzheimer's disease and cerebral AIDS. *J Pharm Sci,* 87, 1308-1315.

Cantley, L. C. and Neel, B. G. (1999) New insights into tumor suppression: PTEN suppresses tumor formation by restraining the phosphoinositide 3-kinase/AKT pathway. *Proc Natl Acad Sci USA,* 96, 4240-4245.

Caruthers, M. H., Beaton, G., Wu, J. V. and Wiesler, W. (1992) Chemical synthesis of deoxyoligonucleotides and deoxyoligonucleotide analogs. *Methods Enzymol,* 211, 3-20.

Conry, R. M., Khazaeli, M. B., Saleh, M. N., Allen, K. O., Barlow, D. L., Moore, S. E., Craig, D., Arani, R. B., Schlom, J. and LoBuglio, A. F. (1999) Phase I trial of a recombinant vaccinia virus encoding carcinoembryonic antigen in metastatic adenocarcinoma: comparison of intradermal versus subcutaneous administration. *Clin Cancer Res,* 5, 2330-2337.

Czauderna, F., Fechtner, M., Dames, S., Aygun, H., Klippel, A., Pronk, G. J., Giese, K. and Kaufmann, J. (2003) Structural variations and stabilising modifications of synthetic siRNAs in mammalian cells. *Nucleic Acids Res,* 31, 2705-2716.

Elayadi, A. N., Demieville, A., Wancewicz, E. V., Monia, B. P. and Corey, D. R. (2001) Inhibition of telomerase by 2'-O-(2-methoxyethyl) RNA oligomers: effect of length, phosphorothioate substitution and time inside cells. *Nucleic Acids Res,* 29, 1683-1689.

Ellisen, L. W. and Haber, D. A. (1998) Hereditary breast cancer. *Annu Rev Med,* 49, 425-436.

Emerich, D. F., Tracy, M. A., Ward, K. L., Figueiredo, M., Qian, R., Henschel, C. and Bartus, R. T. (1999) Biocompatibility of poly (DL-lactide-co-glycolide) microspheres implanted into the brain. *Cell Transplant,* 8, 47-58.

Fearon, E. R. and Vogelstein, B. (1990) A genetic model for colorectal tumorigenesis. *Cell,* 61, 759-767.

Fire, A., Xu, S., Montgomery, M. K., Kostas, S. A., Driver, S. E. and Mello, C. C. (1998) Potent and specific genetic interference by double-stranded RNA in *Caenorhabditis elegans. Nature,* 391, 806-811.

Foulds, L. (1958) The natural history of cancer. *J Chronic Dis,* 8, 2-37.

Gonzalez, H., Hwang, S. J. and Davis, M. E. (1999) New class of polymers for the delivery of macromolecular therapeutics. *Bioconjug Chem,* 10, 1068-1074.

Good, P. D., Krikos, A. J., Li, S. X., Bertrand, E., Lee, N. S., Giver, L., Ellington, A., Zaia, J. A., Rossi, J. J. and Engelke, D. R. (1997) Expression of small, therapeutic RNAs in human cell nuclei. *Gene Ther,* 4, 45-54.

Hofland, H. and Huang, L. (1995) Inhibition of human ovarian carcinoma cell proliferation by liposome-plasmid DNA complex. *Biochem Biophys Res Commun,* 207, 492-496.

Jolliet-Riant, P. and Tillement, J. P. (1999) Drug transfer across the blood-brain barrier and improvement of brain delivery. *Fundam Clin Pharmacol,* 13, 16-26.

Klippel, A., Escobedo, M. A., Wachowicz, M. S., Apell, G., Brown, T. W., Giedlin, M. A., Kavanaugh, W. M. and Williams, L. T. (1998) Activation of phosphatidylinositol 3-kinase is sufficient for cell cycle entry and promotes cellular changes characteristic of oncogenic transformation. *Mol Cell Biol,* 18, 5699-5711.

Lee, W. H., Bookstein, R., Hong, F., Young, L. J., Shew, J. Y. and Lee, E. Y. (1987) Human retinoblastoma susceptibility gene: cloning, identification, and sequence. *Science,* 235, 1394-1399.

Leenders, F., Mopert, K., Schmiedeknecht, A., Santel, A., Czauderna, F., Aleku, M., Penschuck, S., Dames, S., Sternberger, M., Rohl, T., Wellmann, A., Arnold, W., Giese, K., Kaufmann, J. and Klippel, A. (2004) PKN3 is required for malignant prostate cell growth downstream of activated PI 3-kinase. *Embo J,* 23, 3303-3313.

Maurer, N., Mori, A., Palmer, L., Monck, M. A., Mok, K. W., Mui, B., Akhong, Q. F. and Cullis, P. R. (1999) Lipid-based systems for the intracellular delivery of genetic drugs. *Mol Membr Biol,* 16, 129-140.

Nykanen, A., Haley, B. and Zamore, P. D. (2001) ATP requirements and small interfering RNA structure in the RNA interference pathway. *Cell,* 107, 309-321.

Orum, H. and Wengel, J. (2001) Locked nucleic acids: a promising molecular family for gene-function analysis and antisense drug development. *Curr Opin Mol Ther,* 3, 239-243.

Santel, A., Aleku, M., Keil, O., Endruschat, J., Esche, V., Durieux, B., Loffler, K., Fechtner, M., Rohl, T., Fisch, G., Dames, S., Arnold, W., Giese, K., Klippel, A. and Kaufmann, J. (2006a) RNA interference in the mouse vascular endothelium by systemic administration of siRNA-lipoplexes for cancer therapy. *Gene Ther.*

Santel, A., Aleku, M., Keil, O., Endruschat, J., Esche, V., Fisch, G., Dames, S., Loffler, K., Fechtner, M., Arnold, W., Giese, K., Klippel, A. and Kaufmann, J. (2006b) A novel siRNA-lipoplex technology for RNA interference in the mouse vascular endothelium. *Gene Ther.*

Stephenson, R. A., Dinney, C. P., Gohji, K., Ordonez, N. G., Killion, J. J. and Fidler, I. J. (1992) Metastatic model for human prostate cancer using orthotopic implantation in nude mice. *J Natl Cancer Inst,* 84, 951-957.

Sternberger, M., Schmiedeknecht, A., Kretschmer, A., Gebhardt, F., Leenders, F., Czauderna, F., Von Carlowitz, I., Engle, M., Giese, K., Beigelman, L. and Klippel, A. (2002) GeneBlocs are powerful tools to study and delineate signal transduction processes that regulate cell growth and transformation. *Antisense Nucleic Acid Drug Dev,* 12, 131-143.

Weinberg, R. A. (1989) Oncogenes, antioncogenes, and the molecular bases of multistep carcinogenesis. *Cancer Res,* 49, 3713-3721.

Wincott, F., DiRenzo, A., Shaffer, C., Grimm, S., Tracz, D., Workman, C., Sweedler, D., Gonzalez, C., Scaringe, S, and Usman, N. (1995) Synthesis, deprotection, analysis and purification of RNA and ribozymes. *Nucleic Acids Res,* 23, 2677-2684.

Wincott, F. E. and Usman, N. (1997) A practical method for the production of RNA and ribozymes. *Methods Mol Biol,* 74, 59-68.

The features of the present invention disclosed in the specification, the claims, the sequence listing and/or the drawings may both separately and in any combination thereof be material for realizing the invention in various forms thereof.

The invention claimed is:

1. An isolated nucleic acid molecule comprising a double-stranded structure,
   whereby the double-stranded structure comprises a first strand and a second strand,
   whereby the first strand comprises a first stretch of contiguous nucleotides and said first stretch is at least partially complementary to a target nucleic acid,
   whereby the second strand comprises a second stretch of contiguous nucleotides and said second stretch is at least partially complementary to the first stretch,
   whereby the first stretch comprises a nucleic acid sequence which is at least partially complementary to a nucleotide core sequence of the nucleic acid sequence according to SEQ ID NO:1 (NM_013355) or part thereof,
   whereby the nucleotide core sequence comprises the nucleotide sequence from nucleotide positions 1556 to 1574 of SEQ ID NO:1 (SEQ ID NO:6);
   and
   whereby the first stretch is additionally at least partially complementary to a region preceding the 5' end of the nucleotide core sequence and/or to a region following the 3' end of the nucleotide core sequence.

2. The isolated nucleic acid molecule according to claim 1, whereby the first stretch is complementary to the nucleotide core sequence or a part thereof.

3. The isolated nucleic acid molecule according to claim 1, whereby the first stretch is additionally complementary to the region following the 3' end of the nucleotide core sequence and/or to the region preceding the 5' end of the nucleotide core sequence.

4. The isolated nucleic acid molecule according to claim 1, whereby the first stretch and/or the second stretch comprises from 18 to 29 consecutive nucleotides, 19 to 25 consecutive nucleotides or 19 to 23 consecutive nucleotides.

5. The isolated nucleic acid molecule according to claim 4, whereby the first strand consists of the first stretch and/or the second strand consists of the second stretch.

6. The isolated nucleic acid molecule according to claim 1, whereby the double-stranded structure is formed by a first strand and a second strand, whereby the first strand comprises a first stretch of contiguous nucleotides and the second strand comprises a second stretch of contiguous nucleotides and whereby said first stretch is at least partially complementary to said second stretch, whereby
the first stretch consists of a nucleotide sequence according to SEQ ID NO:31 and the second stretch consists of a nucleotide sequence according to SEQ ID NO:30.

7. The isolated nucleic acid molecule according to claim 1, whereby the first stretch and/or the second stretch comprises a plurality of groups of modified nucleotides having a modification at the 2' position forming a regular or alternating positional pattern, whereby within the stretch each group of modified nucleotides is flanked on one or both sides by a flanking group of nucleotides, whereby the flanking nucleotide(s) forming the flanking group of nucleotides is/are either an unmodified nucleotide or a nucleotide having a modification different from the modification of the modified nucleotides.

8. The isolated nucleic acid molecule according to claim 1, whereby the first stretch and/or the second stretch comprises a pattern of groups of modified nucleotides and/or a pattern of flanking groups of nucleotides.

9. The isolated nucleic acid molecule according to claim 1, whereby the first stretch and/or the second stretch comprise at the 3' end a dinucleotide.

10. The isolated nucleic acid molecule according to claim 9, whereby the length of the first stretch and/or of the second stretch consists of 19 to 21 nucleotides.

11. The isolated nucleic acid molecule according to claim 1, whereby the first and/or the second stretch comprise an overhang of 1 to 5 nucleotides at the 3' end.

12. The isolated nucleic acid molecule according to claim 11, whereby the length of the double-stranded structure is from about 16 to 24 nucleotide pairs or 20 to 22 nucleotide pairs.

13. The isolated nucleic acid molecule according to claim 1, whereby the first strand and the second strand are covalently linked to each other.

14. The isolated nucleic acid molecule according claim 1, whereby the nucleic acid molecule consists of each of the two following strands and whereby the underlined nucleotides are 2'-O-methyl:

```
                           (SEQ ID NO: 31)
PKN3-23-v1:   uuguccaggaaguccucaagucu (SEQ ID NO: 30)
              agacuugaggacuuccuggacaa;
```

15. A liposomal formulation comprising a nucleic acid molecule according to claim 1.

16. A lipoplex comprising a nucleic acid molecule according to claim 1 and a liposome.

17. The lipoplex according to claim 16, wherein the liposome consists of:
a) about 50 mol % β-arginyl-2,3-diaminopropionic acid-N-palmityl-N-oleyl-amide trihydrochloride;
b) about 48 to 49 mol % 1,2-diphytanoyl-sn-glycero-3-phosphoethanolamine (DPhyPE); and
c) about 1 to 2 mol % 1,2-distearoyl-sn-glycero-3-phosphoethanolamine-polyethylen-glycole or N-(Carbonyl-methoxypolyethyleneglycol-2000)-1,2-distearoyl-sn-glycero-3-phosphoethanolamine sodium salt.

18. The lipoplex according to claim 17, wherein the zeta-potential of the lipoplex is about 35 to 60 mV or about 45 to 50 mV.

19. The lipoplex according to claim 17, wherein the lipoplex has a size of about 50 to 400 nm, about 100 to 140 nm, or about 110 nm to 130 nm, as determined by QELS.

20. A vector comprising or coding for a nucleic acid molecule according to claim 1.

21. An isolated host cell comprising a nucleic acid molecule according to claim 1.

22. A method of treating an angiogenesis-dependent disease comprising the administration of a nucleic acid molecule according to claim 1 to a subject having said angiogenesis-dependent disease in an amount sufficient to treat said disease, wherein said disease is characterized or caused by insufficient, abnormal or excessive angiogenesis.

23. The method according to claim 22, wherein the angiogenesis is angiogenesis of adipose tissue, skin, heart, eye, lung, intestines, reproductive organs, bone and joints.

24. The method according to claim 22, wherein the disease is selected from the group consisting of infectious diseases, autoimmune disorders, vascular malformation, atherosclerosis, transplant arteriopathy, obesity, psoriasis, warts, allergic dermatitis, persistent hyperplastic vitreous syndrome, diabetic retinopathy, retinopathy of prematurity, age-related macular disease, choroidal neovascularization, primary pulmonary hypertension, asthma, nasal polyps, inflammatory bowel and periodontal disease, ascites, peritoneal adhesions, endometriosis, uterine bleeding, ovarian cysts, ovarian hyperstimulation, arthritis, synovitis, osteomyelitis, and osteophyte formation.

25. The method according to claim 22, wherein the disease is a neoplastic disease.

26. The method according to claim 25, wherein said neoplastic disease is selected from the group comprising bone cancer, breast cancer, prostate cancer, cancer of the digestive system, colorectal cancer, liver cancer, lung cancer, kidney cancer, urogenital cancer, pancreatic cancer, pituitary cancer, testicular cancer, orbital cancer, head and neck cancer, cancer of the central nervous system and cancer of the respiratory system.

27. The method according to claim 22, wherein said method further comprises the administration of a second therapy selected from the group comprising chemotherapy, cryotherapy, hyperthermia, antibody therapy, radiation therapy and anti-angiogenesis therapy.

28. The method according to claim 27, wherein the second therapy is antibody therapy.

29. The method according to claim 27, wherein the second therapy comprises an anti-angiogenesis therapy using a kinase receptor inhibitor or a tyrosine kinase receptor inhibitor, wherein the receptor is selected from a VEGF receptor, PDGF receptor, Tie-2, FGFR or EGFR.

30. The method according to claim 29, whereby the inhibitor is selected from the group comprising siRNA, antisense molecules, aptamers, spiegelmers, high affinity binding peptides, peptide aptamers, anticalines and antibodies.

31. The isolated host cell according to claim 21, wherein said nucleic acid molecule has a first stretch that consists of a nucleotide sequence according to SEQ ID NO:31 and a second stretch that consists of a nucleotide sequence according to SEQ ID NO:30.

32. The liposomal formulation according to claim 15, wherein the nucleic acid molecule consists of each of the two following strands and the underlined nucleotides are 2'-O-methyl:

```
                              (SEQ ID NO: 31)
PKN3-23-v1:    uuguccaggaaguccucaagucu (SEQ ID NO: 30)
               agacuugaggacuuccuggacaa.
```

33. The nucleic acid molecule according to claim 4, wherein the first stretch and the second stretch are each from 18 to 29 consecutive nucleotides.

34. The nucleic acid molecule according to claim 33, wherein said nucleic acid molecule is blunt ended on one end of said molecule.

35. The nucleic acid molecule according to claim 33, wherein said nucleic acid molecule is blunt ended on both ends of said molecule.

36. The nucleic acid molecule according to claim 33, wherein said nucleic acid molecule has an overhang of 1 to 8 nucleotides at the 5' end of said molecule.

37. The nucleic acid molecule according to claim 33, wherein said nucleic acid molecule has an overhang of 1 to 8 nucleotides at the 3' end of said molecule.

38. The nucleic acid molecule according to claim 33, wherein said nucleic acid molecule has an overhang of 1 to 8 nucleotides at both the 5' and 3' ends of said molecule.

39. The nucleic acid molecule according to claim 33, wherein said nucleic acid molecule has an overhang of 1 to 8 nucleotides.

40. A lipoplex comprising a nucleic acid molecule and a liposome, wherein the liposome consists of:
 a) about 50 mol % β-arginyl-2,3-diaminopropionic acid-N-palmityl-N-oleyl-amide trihydrochloride;
 b) about 48 to 49 mol % 1,2-diphytanoyl-sn-glycero-3-phosphoethanolamine (DPhyPE); and
 c) about 1 to 2 mol % 1,2-distearoyl-sn-glycero-3-phosphoethanolamine-polyethylen-glycol; and
the nucleic acid molecule consists of each of the two following strands and the underlined nucleotides are 2'-O-methyl:

```
                              (SEQ ID NO: 31)
PKN3-23-v1:    uuguccaggaaguccucaagucu (SEQ ID NO: 30)
               agacuugaggacuuccuggacaa
```

41. The lipoplex according to claim 40, wherein the nucleic acid molecule consists of each of the two following strands and the underlined nucleotides are 2'-O-methyl:

```
                              (SEQ ID NO: 31)
PKN3-23-v1:    uuguccaggaaguccucaagucu (SEQ ID NO: 30)
               agacuugaggacuuccuggacaa.
```

42. The lipoplex according to claim 40, wherein said β-arginyl-2,3-diaminopropionic acid-N-palmityl-N-oleyl-amide trihydrochloride is (β-(L-arginyl)-2,3-L-diaminopropionic acid-N-palmityl-N-oleyl-amide tri-hydrochloride).

43. The lipoplex according to claim 17, wherein said β-arginyl-2,3-diaminopropionic acid-N-palmityl-N-oleyl-amide trihydrochloride is (β-(L-arginyl)-2,3-L-diaminopropionic acid-N-palmityl-N-oleyl-amide tri-hydrochloride).

44. The lipoplex according to claim 17, wherein said nucleic acid molecule has a first stretch that consists of a nucleotide sequence according to SEQ ID NO:31 and the second stretch that consists of a nucleotide sequence according to SEQ ID NO:30.

45. The liposomal formulation according to claim 15, wherein the first stretch and the second stretch of the nucleic acid molecule each consist of 18 to 29 consecutive nucleotides.

46. The liposomal formulation according to claim 45, wherein said nucleic acid molecule is blunt ended on one end of said molecule.

47. The liposomal formulation according to claim 45, wherein said nucleic acid molecule is blunt ended on both ends of said molecule.

48. The liposomal formulation according to claim 45, wherein said nucleic acid molecule has an overhang of 1 to 8 nucleotides at the 5' end of said molecule.

49. The liposomal formulation according to claim 45, wherein said nucleic acid molecule has an overhang of 1 to 8 nucleotides at the 3' end of said molecule.

50. The liposomal formulation according to claim 45, wherein said nucleic acid molecule has an overhang of 1 to 8 nucleotides at both the 5' and 3' ends of said molecule.

51. The liposomal formulation according to claim 45, wherein said nucleic acid molecule has an overhang of 1 to 8 nucleotides.

52. The isolated host cell according to claim 31, wherein the nucleic acid molecule consists of each of the two following strands and the underlined nucleotides are 2'-O-methyl:

```
                              (SEQ ID NO: 31)
PKN3-23-v1:    uuguccaggaaguccucaagucu (SEQ ID NO: 30)
               agacuugaggacuuccuggacaa.
```

53. The vector according to claim 20, wherein said vector comprises or codes for a nucleic acid molecule that has a first stretch that consists of a nucleotide sequence according to SEQ ID NO:31 and a second stretch that consists of a nucleotide sequence according to SEQ ID NO:30.

* * * * *

UNITED STATES PATENT AND TRADEMARK OFFICE
CERTIFICATE OF CORRECTION

PATENT NO.         : 8,232,256 B2
APPLICATION NO.    : 12/307052
DATED              : July 31, 2012
INVENTOR(S)        : Jorg Kaufmann, Oliver Keil and Ansgar Santel It is certified that error appears in the above-identified patent and that said Letters Patent is hereby corrected as shown below:

Column 7,
Line 5, "acuugaggacuuccuggacaaug (SEQ. ID. No. 36)" should read
   --acuugaggacuuccuggacaaug (SEQ. ID. No. 36)--.
Line 21, "ccuggacaaugccugucac (SEQ. ID. No. 10)" should read
   --ccuggacaaugccugucac (SEQ. ID. No. 10)--.

Column 8,
Lines 16-17, "a diseases" should read --a disease--.

Column 12,
Line 37, "ccuggacaaugccugucac (SEQ. ID. No. 10)" should read
   --ccuggacaaugccugucac (SEQ. ID. No. 10)--.

Column 15,
Line 39, "particular" should read --particularly--.

Column 17,
Line 51, "and end" should read --an end--.

Column 19,
Line 8, "of nucleotide" should read --of nucleotides--.
Line 60, "both end" should read --both ends--.

Column 22,
Lines 57-58, "a glyceryl modification at the 3' end" should read
      --a phosphorothioate internucleotide linkage at the 3' end--.
Line 61, "modification are the 3' end" should read
   --modification at the 3' end--.

Signed and Sealed this
Ninth Day of April, 2013

Teresa Stanek Rea
*Acting Director of the United States Patent and Trademark Office*

Column 23,
Line 56, "said antisens" should read --said antisense--.

Column 24,
Line 61, "consists of" should read --consist of--.

Column 26,
Line 54, "shelve life" should read --shelf life--.

Column 27,
Lines 10-11, "(Holland" should read --(Hofland--.

Column 28,
Line 28, "examples f or" should read --examples for--.

Column 30,
Line 67, "from of" should read --form of--.

Column 37,
Line 49, "nead neck" should read --head, neck--.

Column 41,
Line 40, "ccuggacaaugccugucac (SEQ. ID. No. 10)" should read
    --ccuggacaaugccugucac (SEQ. ID. No. 10)--.

Column 43, Table 1b,
Line 17, "*ac*uugagga*c*uu*cc*uggacaa*ug* (SEQ. ID. No. 36)" should read
    --*ac*uugagga*c*uu*cc*uggacaa*ug* (SEQ. ID. No. 36)--.

Column 44, Table 2,
Line 66, "agcugcuccaggggcgguugga (SEQ. ID. No. 55)" should read
    --agcugcuccaggcggcgguugga(SEQ. ID. No. 55)--.
Line 67, "uccaaccgcggccuggagcagcu (SEQ. ID. No. 54)" should read
    --uccaaccgccgccuggagcagcu (SEQ. ID. No. 54)--.

Column 47,
Line 54, "from 25 to day 35" should read --from day 25 to day 35--.

Column 50,
Line 22, "shows" should read --show--.

UNITED STATES PATENT AND TRADEMARK OFFICE
CERTIFICATE OF CORRECTION

Page 1 of 3

PATENT NO. : 8,232,256 B2
APPLICATION NO. : 12/307052
DATED : July 31, 2012
INVENTOR(S) : Jorg Kaufmann, Oliver Keil and Ansgar Santel It is certified that error appears in the above-identified patent and that said Letters Patent is hereby corrected as shown below:

In the Specification

Column 7,
Line 5, " acuugaggacuuccuggacaaug (SEQ. ID. No. 36) " should read
-- acuugaggacuuccuggacaaug (SEQ. ID. No. 36) --.
Line 21, " ccuggacaaugccugucac (SEQ. ID. No. 10) " should read
-- ccuggacaaugccugucac (SEQ. ID. No. 10) --.

Column 8,
Lines 16-17, "a diseases" should read --a disease--.

Column 12,
Line 37, " ccuggacaaugccugucac (SEQ. ID. No. 10) " should read
-- ccuggacaaugccugucac (SEQ. ID. No. 10) --.

Column 15,
Line 39, "particular" should read --particularly--.

Column 17,
Line 51, "and end" should read --an end--.

Column 19,
Line 8, "of nucleotide" should read --of nucleotides--.
Line 60, "both end" should read --both ends--.

This certificate supersedes the Certificate of Correction issued April 9, 2013.

Signed and Sealed this
Seventeenth Day of September, 2013

Teresa Stanek Rea
*Deputy Director of the United States Patent and Trademark Office*

Column 22,
Lines 57-58, "a glyceryl modification at the 3' end" should read --a phosphorothioate internucleotide linkage at the 3' end--.
Line 61, "modification are the 3' end" should read --modification at the 3' end--.

Column 23,
Line 56, "said antisens" should read --said antisense--.

Column 24,
Line 61, "consists of" should read --consist of--.

Column 26,
Line 54, "shelve life" should read --shelf life--.

Column 27,
Lines 10-11, "(Holland" should read --(Hofland--.

Column 28,
Line 28, "examples f or" should read --examples for--.

Column 30,
Line 67, "from of" should read --form of--.

Column 37,
Line 49, "nead neck" should read --head, neck--.

Column 41,
Line 40, " ccuggacaaugccugucac (SEQ. ID. No. 10) " should read
    -- ccuggacaaugccugucac (SEQ. ID. No. 10) --.

Column 43, Table 1b,
Line 17, "acuugaggacuuccuggacaaug (SEQ. ID. No. 36)" should read
    -- acuugaggacuuccuggacaaug (SEQ. ID. No. 36) --.

Column 44, Table 2,
Line 66, " agcugcuccaggggcgguugga (SEQ. ID. No. 55) " should read
    -- agcugcuccaggcggcgguugga(SEQ. ID. No. 55) --.
Line 67, "uccaaccgcggccuggagcagcu (SEQ. ID. No. 54)" should read
    -- uccaaccgccgccuggagcagcu (SEQ. ID. No. 54) --.

Column 47,
Line 54, "from 25 to day 35" should read --from day 25 to day 35--.

Column 50,
Line 22, "shows" should read --show--.